United States Patent
Su et al.

(10) Patent No.: US 9,193,687 B2
(45) Date of Patent: Nov. 24, 2015

(54) PHENYL N-MUSTARD LINKED TO DNA-AFFINIC MOLECULES OR WATER-SOLUBLE ARYL RINGS, METHOD AND THEIR USE AS CANCER THERAPEUTIC AGENTS

(75) Inventors: Tsann-Long Su, New Taipei (TW); Ting-Chao Chou, Paramus, NJ (US); Te-Chuang Lee, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/539,221

(22) Filed: Jun. 29, 2012

(65) Prior Publication Data

US 2013/0178494 A1 Jul. 11, 2013

Related U.S. Application Data

(63) Continuation-in-part of application No. 12/008,512, filed on Jan. 11, 2008, now Pat. No. 8,222,297.

(60) Provisional application No. 60/879,853, filed on Jan. 11, 2007.

(51) Int. Cl.
| | |
|---|---|
| *C07D 215/42* | (2006.01) |
| *C07D 215/233* | (2006.01) |
| *C07D 207/09* | (2006.01) |
| *C07D 211/06* | (2006.01) |
| *C07D 491/056* | (2006.01) |
| *C07D 219/10* | (2006.01) |
| *C07C 275/40* | (2006.01) |
| *C07C 275/42* | (2006.01) |

(52) U.S. Cl.
CPC .......... *C07D 215/42* (2013.01); *C07C 275/40* (2013.01); *C07C 275/42* (2013.01); *C07D 207/09* (2013.01); *C07D 211/06* (2013.01); *C07D 215/233* (2013.01); *C07D 219/10* (2013.01); *C07D 491/056* (2013.01)

(58) Field of Classification Search
CPC .......... C07D 214/42; C07D 214/233; C07D 207/09; C07D 211/06; C07D 219/10; C07D 491/056
USPC ............................................. 514/597; 564/60
See application file for complete search history.

(56) References Cited

U.S. PATENT DOCUMENTS

2008/0171765 A1* 7/2008 Su et al. ................... 514/291

OTHER PUBLICATIONS

Kakadiya et al., Bioorganic & Medicinal Chemistry, 18 (2010), 2285-2299.*
Kapuriya et al., Bioorganic & Medicinal Chemistry 16 (2008) 5413-5423.*

* cited by examiner

*Primary Examiner* — Rebecca Anderson
(74) *Attorney, Agent, or Firm* — VLP Law Group LLP; Kent H. Cheng

(57) ABSTRACT

The present disclosure relates to new DNA-directed alkylating agents and water-soluble N-mustard agents with improved chemical stability and anti-tumor therapeutic efficacy.

13 Claims, 6 Drawing Sheets

PHENYL N-MUSTARD LINKED TO DNA-AFFINIC MOLECULES OR WATER-SOLUBLE ARYL RINGS, METHOD AND THEIR USE AS CANCER THERAPEUTIC AGENTS

RELATED APPLICATIONS

This application is a continuation-in-part application of and claims priority from U.S. patent application Ser. No. 12/008,512, filed Jan. 11, 2008, which claims priority from U.S. Provisional Patent Application Ser. No. 60/879,853 which was filed on Jan. 11, 2007. The contents of U.S. patent application Ser. No. 12/008,512 and U.S. Provisional Patent Application Ser. No. 60/879,853 are entirely incorporated herein by reference.

BACKGROUND OF THE INVENTION

1. Field of the Invention

The present application pertains to N-mustard compounds, methods for their preparation, pharmaceutical compositions comprising such compounds, and the use of such compounds and compositions in therapy and treatment, for example, of cancer.

2. Description of the Related Art

Gene-targeting agents, such as N-mustards, have played an important part in anticancer drug development.[1] Drawbacks of using DNA-alkylating agents include their high reactivity resulting in loss of therapeutic activity against malignancy by reacting with other cellular components such as proteins, thiols or genes,[2] lacking of intrinsic DNA binding affinity of the core N,N-bis(2-chloroethyl)amine pharmacophore and a requirement for bifunctional crosslinking of DNA to be fully cytotoxic resulting in lower their potency and producing high ratio of genotoxic monoadducts to crosslinkers (up 20:1).[3] It has demonstrated that the targeting mustards to DNA by attaching to DNA-affinic carriers facilitates in finding compounds of higher cytotoxicity and potency than the corresponding untargeted N-mustard moiety. There is renewed interest in these general class of drugs, following recent demonstrations that both their sequence and regioselectivity of DNA alkylation can be altered by attaching them to a variety of DNA-affinic carriers (such as DNA-intercalators or DNA minor groove binders) and that can result in a modified spectrum of biological activity.[4-14]

Among DNA-targeting mustards using 9-anilinoacridines as a DNA-affinic carrier, compound 1 and 2, were less cytotoxic than amsacrine (3) and the 4-linked analogues (1) showed slightly higher in vivo antileukemic activity than their corresponding 1'-linked analogues (2), indicating that the N-mustard residue would prefer to be linked to the acridone chromophore to have better cytotoxicity.[10] In contrast, our recent research on development of gene-targeting N-mustards demonstrated that alkyl N-mustard linked to the anilino ring or acridine chromophore of 9-anilinoacridines, such as (3-(acridin-9-ylamino)-5-{2-[bis-(2-chloroethyl)amino]-ethoxy}phenylmethanol (4, BO-0742)[15,16] and N1-(4-{2-[bis(2-chloroethyl)-amino]-ethoxy}acridin-9-yl)-5-methoxybenzene-1,3-diamine hydrochloride (5, BO-0940),[17] respectively, were significantly more cytotoxic (>100-time) than 3-(9-acridinyl-amino)-5-hydroxymethylaniline (AHMA, 6)[18,19] in inhibiting various human leukemia and solid tumor in vitro and in vivo. Formulae of the compounds discussed in this paragraph is shown in FIG. 1.

N-mustard derivatives, in general, have a short half-life in mice and human plasma. To overcome the chemical instability of N-mustards, a number of aziridinylnitrobenzamides[20,21] (i.e., 7, CB 1954, Scheme 1) and 5-[N,N-bis(2-haloethyl)amino]-2,4-dinitrobenzamides (9)[20] or aniline and benzoic acid mustards linked to L-glutamic acid moiety through a urea or carbamic acid ester linkage (11, Scheme 2)[22] or carboxamide (13, CMDA)[22] have been synthesized as candidate prodrugs for gene-directed enzyme prodrug therapy (GDEPT).[23] The electron-withdrawing aromatic nitro function of the aziridinylnitrobenzamides can be reduced efficiently to the active electron-donating hydroxyamino by *E. coli* nitro-reductase (NR) (Scheme 1). The activation of the glutamic acid containing mustards requires carboxypeptidase G2 (CPG2). It has demonstrated that these prodrugs were effective substrates for the enzyme and showed to have improved therapeutic activity in CPG2-expressing xenografts.[24-32]

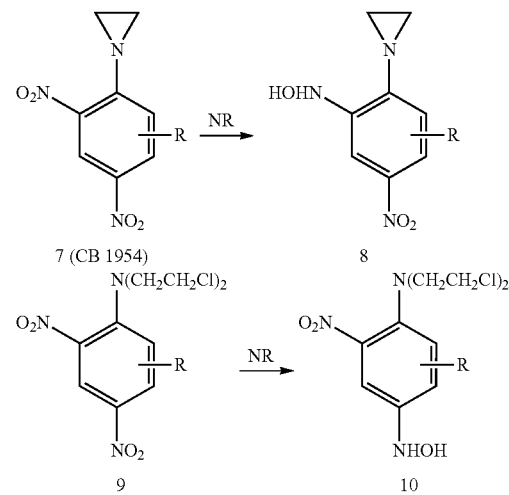

Scheme 1

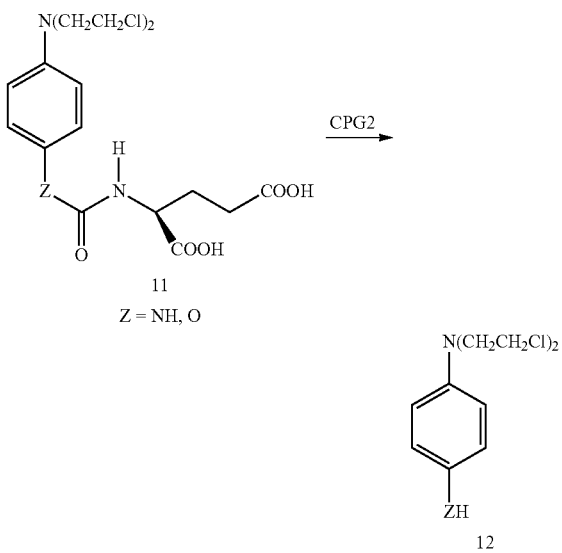

Scheme 2

-continued

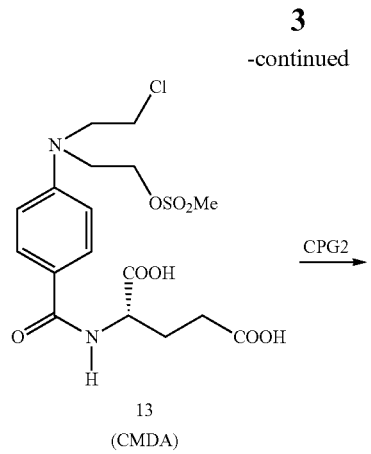

13
(CMDA)

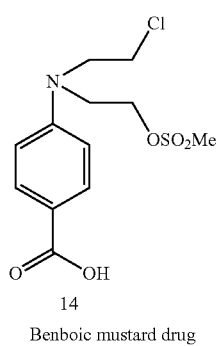

14
Benboic mustard drug

In view of this, it is of great interest to develop new N-mustard compounds with improved chemical stability and antitumor therapeutic efficacy.

SUMMARY OF THE INVENTION

One aspect of the present disclosure pertains to a compound of Formula (I):

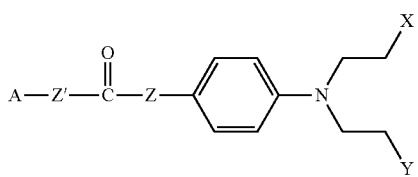

Or a salt thereof, wherein X and Y are independently selected from the group consisting of Cl, Br, I, and OSO$_2$Me X; Z is —NH or —O—; Z' is —NH, —NHNH, —OCH$_2$—, or —O—; A is an aromatic moiety of Formula (A), (B) or (C):

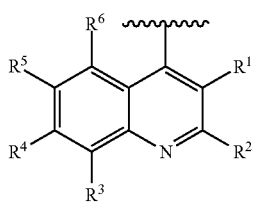

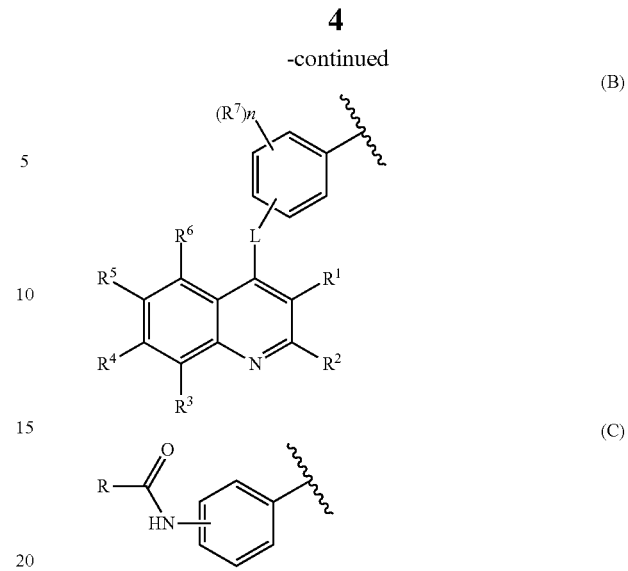

wherein R, $R^1$, $R^2$, $R^3$, $R^4$, $R^5$, $R^6$, $R^7$ and n are as described herein.

Another aspect of the present disclosure pertains to a composition comprising a compound of Formula (I) as described above and a pharmaceutically acceptable carrier.

Yet another aspect of the present disclosure pertains to use of an effective amount of a compound of Formula (I) a pharmaceutically acceptable salt thereof, or pharmaceutical composition thereof in treating cancer, such as brain tumor, breast cancer, colon cancer, leukemia, and neuroblastoma.

Still another aspect of the present disclosure pertains to process of making a compound of Formula (I), as described herein.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DEFINITIONS

Figure 1:
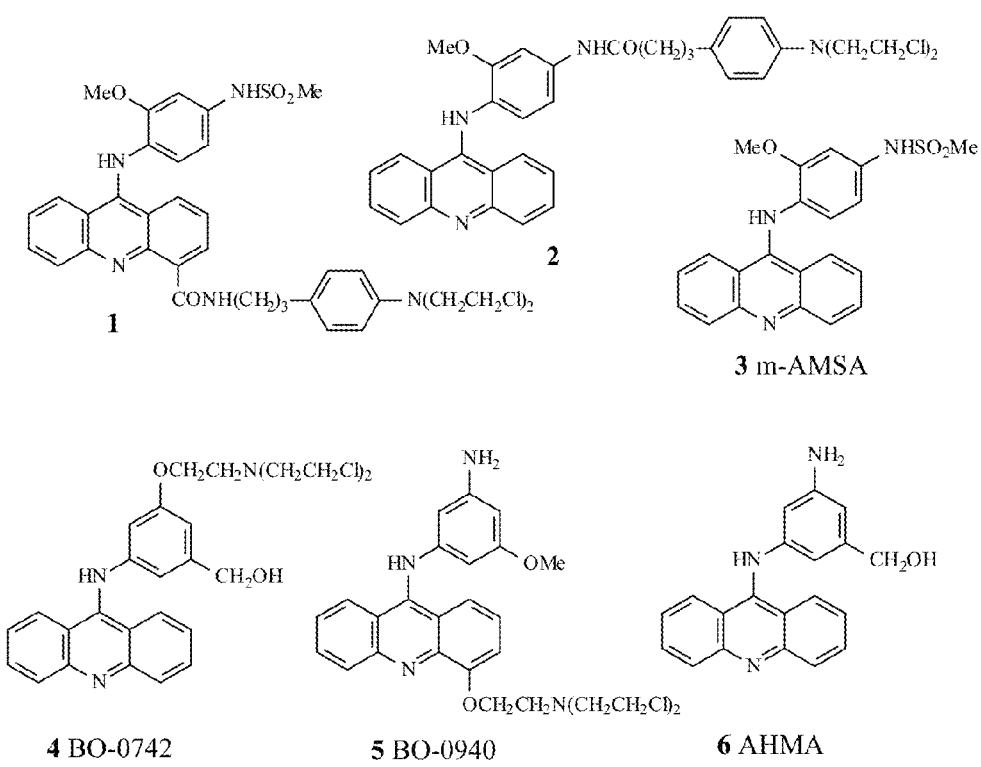
FIG. 1 shows the formulae of compounds 1-6 discussed above in Section "Description of the Related Art."

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

When a range of values is listed, it is intended to encompass each value and sub-range within the range. For example, an "alkyl group having from 1 to 6 carbons" (also referred to herein as "$C_{1-6}$ alkyl") is intended to encompass 1 ($C_1$ alkyl), 2 ($C_2$ alkyl), 3 ($C_3$ alkyl), 4 ($C_4$ alkyl), 5 ($C_5$ alkyl) and 6 ($C_6$ alkyl) carbons, and a range of 1 to 6 ($C_{1-6}$ alkyl), 1 to 5 ($C_{1-5}$ alkyl), 1 to 4 ($C_{1-4}$ alkyl), 1 to 3 ($C_{1-3}$ alkyl), 1 to 2 ($C_{1-2}$ alkyl), 2 to 6 ($C_{2-6}$ alkyl), 2 to 5 ($C_{2-5}$ alkyl), 2 to 4 ($C_{2-4}$ alkyl), 2 to 3 ($C_{2-3}$ alkyl), 3 to 6 ($C_{3-6}$ alkyl), 3 to 5 ($C_{3-5}$ alkyl), 3 to 4 ($C_{3-4}$ alkyl), 4 to 6 ($C_{4-6}$ alkyl), 4 to 5 ($C_{4-5}$ alkyl), and 5 to 6 ($C_{5-6}$ alkyl) carbons.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups.

The terms "alkenyl" and "alkynyl" are given their ordinary meaning in the art and refer to unsaturated aliphatic groups analogous in length and possible substitution to the alkyls described above, but that contain at least one double or triple bond respectively.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted.

"Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. It will be appreciated that an aryl group may be attached via an alkyl moiety to form an "alkylaryl" group.

Alkyl, alkenyl, alkynyl, heterocyclyl and aryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heterocyclyl, "substituted" or "unsubstituted" aryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound.

In certain embodiments, a compound of the present invention is provided as a salt. Salts are well known in the art. For example, Berge et al., describe pharmaceutically acceptable salts in detail in *J. Pharmaceutical Sciences*, 1977, 66, 1-19, incorporated herein by reference. Salts of the compounds of this invention include those derived from suitable inorganic and organic acids and bases. Examples include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include, when appropriate, ammonium, quaternary ammonium, and amine cations formed using counterions such as halide, hydroxide, carboxylate, sulfate, phosphate, nitrate, loweralkyl sulfonate and aryl sulfonate.

Any of the compounds described herein may be in a variety of forms, such as, but not limited to, salts, solvates, hydrates, tautomers, and isomers.

In certain embodiments, the compound described herein may exist in various tautomeric forms. The term "tautomer" as used herein includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diasteromers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

It must be noted that as used herein and in the appended claims, the singular forms "a," "and," and "the" include plural referents unless the context clearly dictates otherwise. Thus, for example, reference to "a biomarker" includes a plurality of such biomarkers and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PRESENTLY PREFERRED EMBODIMENTS

To develop new antitumor agents, we have designed and synthesized various types of new N-mustard conjugates by linking phenyl N-mustard pharmacophore to a DNA-affinic carrier such as 9-anilinoacridines (DNA intercalating agents) or quinolines (DNA minor groove binder) via suitable linkers such as urea, carbamic acid, carbonic acid ester, hydrazinecarboxamide, oxypneylurea, or oxyphenylcarbamic acid ester linkage. The reactivity of the N-mustard can be reduced by these linkers to form stable N-mustard derivatives. Thus, the new compounds are chemically stable with good pharmacokinetic (PK) profile.

In addition, to improve the chemical stability and water-solubility of lipohilic N-mustards for clinical application, we have synthesized a series of new water-soluble N-mustard derivatives by linking phenyl N-mustard pharmacophore is linked to a benzene moiety via suitable. The benzene moiety bears an amide side chain at the para- or meta-position corresponding to the linker.

The present disclosure relates to new DNA-directed alkylating agents and water-soluble N-mustard agents, and the use of the compounds for cancer treatment. The present disclosure also provides synthetic routes to the novel compounds.

I. Novel N-Mustard Conjugates

The present disclosure provides novel N-mustard conjugates having the structure of Formula (I):

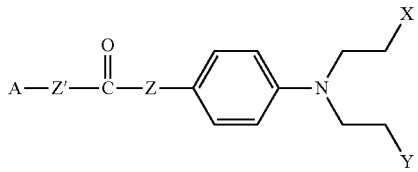

(I)

or a salt thereof;
wherein:
X and Y are independently selected from the group consisting of Cl, Br, I, and $OSO_2Me$;
Z is NH or O;
Z' is —NH, —NHNH, —$OCH_2$—, or —O—;
A is an aromatic moiety of Formula (A), (B) or (C):

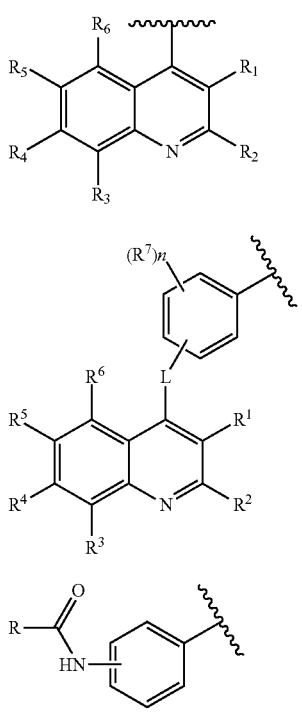

wherein:
each of $R^1$ and $R^2$ is independently selected from hydrogen, halogen, optionally substituted $C_1$-$C_6$ alkyl, optionally substituted alkenyl, optionally substituted alkynyl, optionally substituted heterocyclyl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^1$ and $R^2$ are taken together with their intervening atoms to form a carbocycle or heterocycle;
$R^3$, $R^4$, $R^5$ and $R^6$ are each independently selected from hydrogen, halogen, optionally substituted $C_1$-$C_6$ alkyl, optionally substituted alkenyl, optionally substituted alkynyl, optionally substituted heterocyclyl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^4$ and $R^5$ taken together with their intervening atoms form a carbocycle or heterocycle;
each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl;
each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle.
each $R^7$ is independently selected from halogen, optionally substituted $C_1$-$C_6$ alkyl, optionally substituted alkenyl, optionally substituted alkynyl, optionally substituted heterocyclyl, and optionally substituted aryl, —$OR^a$, —$CH_2OH$, —$NHCOR^a$, —$NHC(O)OR^a$, wherein $R^a$ is $C_1$-$C_6$ alkyl, phenyl, or benzyl;
n is 0-4;
R is selected from optionally substituted $C_1$-$C_6$ alkyl, optionally substituted alkenyl, optionally substituted alkynyl, optionally substituted heterocyclyl, optionally substituted aryl.

In one example, the N-mustard conjugate is of the Formula (I-A):

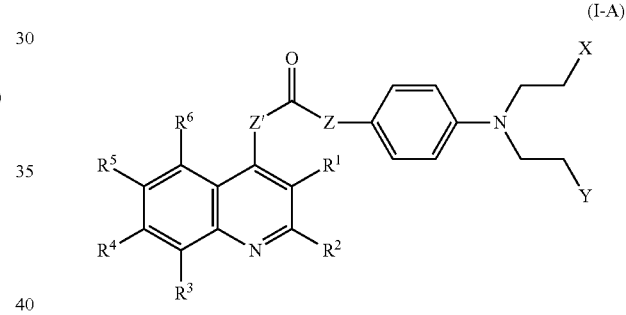

(I-A)

or a salt thereof;
wherein:
X and Y are independently selected from the group consisting of Cl, Br, I, and $OSO_2Me$;
Z is —NH or —O—;
Z' is —NH, —NHNH, —$OCH_2$—, or —O—;
each of $R^1$ and $R^2$ is independently selected from hydrogen, halogen, optionally substituted $C_1$-$C_6$ alkyl, optionally substituted alkenyl, optionally substituted alkynyl, optionally substituted heterocyclyl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^1$ and $R^2$ are taken together with their intervening atoms to form a carbocycle or heterocycle;
$R^3$, $R^4$, $R^5$ and $R^6$ are each independently selected from hydrogen, halogen, optionally substituted $C_1$-$C_6$ alkyl, optionally substituted alkenyl, optionally substituted alkynyl, optionally substituted heterocyclyl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^4$ and $R^5$ are taken together with their intervening atoms to form a carbocycle or heterocycle;
each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl;

each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle.

In some embodiments, X and Y are the same. In a preferred embodiment, X and Y are Cl.

In some embodiments, Z is —NH. In some embodiments, Z is —O—.

In some embodiments, Z' is —NH. In some embodiments, Z' is —NHNH. In some embodiments, Z' is —(CH$_2$)O—. In some embodiments, Z' is —O—.

Each of $R^1$, $R^2$, $R^3$, $R^4$, $R^5$ and $R^6$ can be independently hydrogen, halogen, alkyl, alkenyl, alkynyl, heterocyclyl, aryl, —OR$^A$, —OC(O)R$^A$, —SR$^A$, —N(R$^B$)$_2$, —N(R$^A$)C(O)R$^A$, —C(O)N(R$^B$)$_2$, —CN, —NO$_2$, —C(O)R$^A$, —C(O)OR$^A$, —S(O)R$^A$, —SO$_2$R$^A$, —SO$_2$N(R$^B$)$_2$, or —NHSO$_2$R$^B$.

In certain embodiments, each of $R^1$, $R^2$, $R^3$, $R^4$, $R^5$ and $R^6$ is independently selected from —H, —OH, —Cl, —Br, —F, $C_{1-6}$ alkyl, $C_{1-6}$ alkoxy, alkynyl, aryl, —NO$_2$, —N(R$^B$)$_2$, —C(O)CH$_3$, —CO$_2$H, —C(O)OR$^A$, —C(O)N(R$^B$)$_2$, —CN, heterocyclyl, —SO$_2$-alkyl, and —SO$_2$-aryl.

In certain embodiments, each of $R^1$, $R^2$, $R^3$, $R^4$, $R^5$ and $R^6$ is independently selected from —H, —OH, —Cl, —Br, —F, methyl, ethyl, methoxy, ethoxy, —C≡C-aryl, phenyl, naphthyl, —NO$_2$, —NH—$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl.

In certain embodiments, $R^4$ and $R^5$ are taken together with their intervening atoms to form a heterocycle.

In some embodiments, $R^1$ and $R^2$ are taken together with their intervening atoms to form a 6-membered aromatic ring, wherein the ring is unsubstituted or substituted by one or more R' groups; and R' is hydrogen, halogen, $C_1$-$C_6$ alkyl, alkenyl, alkynyl, heterocyclyl, aryl, —OR$^A$, —OC(O)R$^A$, —SR$^A$, —N(R$^B$)$_2$, —N(R$^A$)C(O)R$^A$, —C(O)N(R$^B$)$_2$, —CN, —NO$_2$, —C(O)R$^A$, —C(O)OR$^A$, —S(O)R$^A$, —SO$_2$R$^A$, —SO$_2$N(R$^B$)$_2$, and —NHSO$_2$R$^B$. In certain embodiments, the R' group is selected from hydrogen, methyl, methoxy, CONHR$^b$, and CONH(CH$_2$)$_n$N(R$^b$)$_2$, wherein $R^b$ is $C_1$-$C_6$ alkyl, and n is 1 to 6.

Examples of such compounds of Formula (I-A) include, but are not limited to, the following:

BO-1038

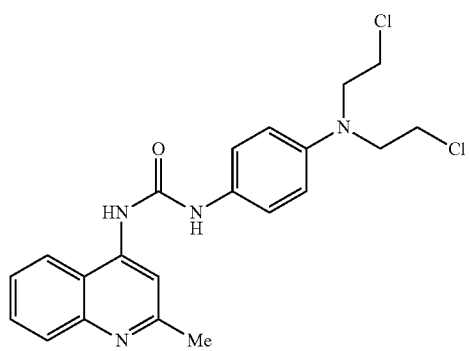

BO-1231

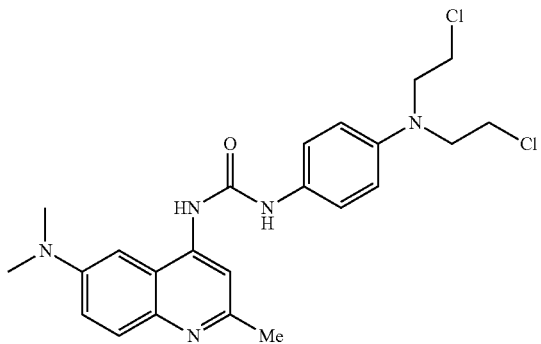

BO-1049

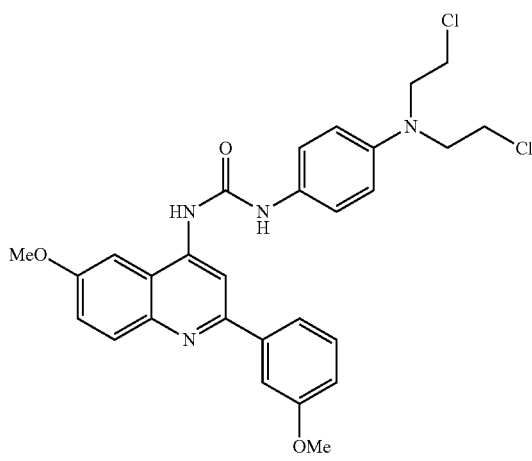

BO-1233

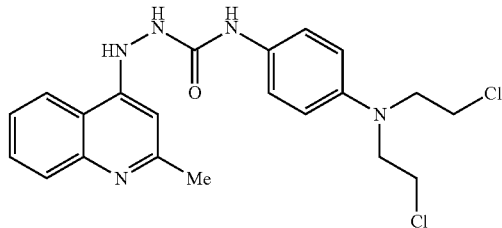

BO-1242

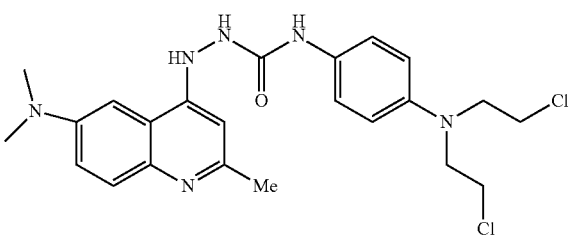

BO-1393

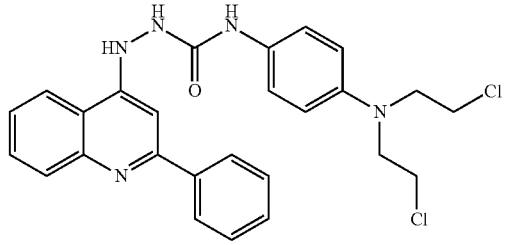

-continued

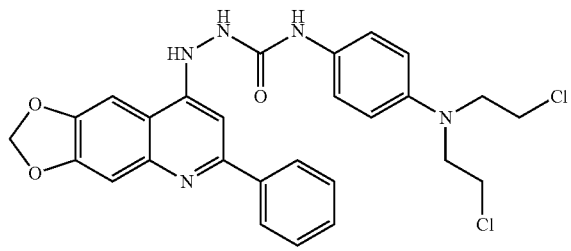
BO-1391

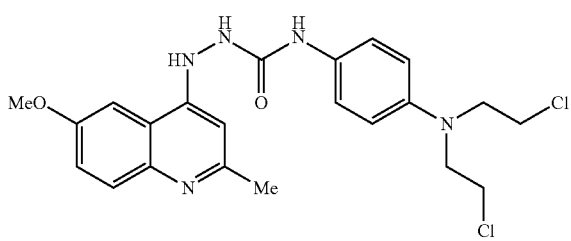
BO-1228

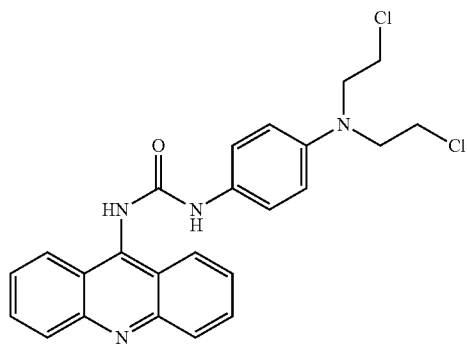
BO-1034

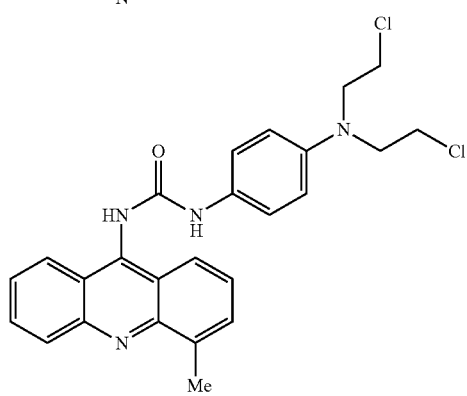

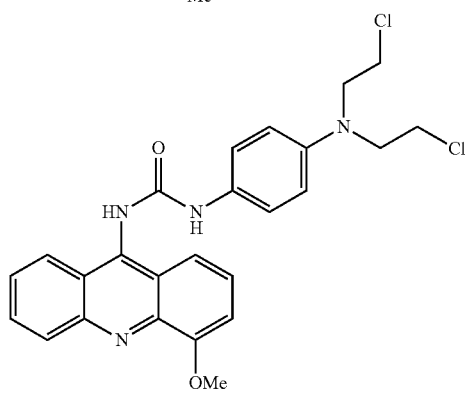

-continued

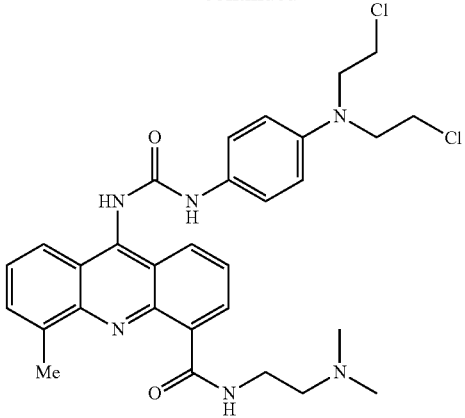

In another example, the N-mustard conjugate is of Formula (I-B):

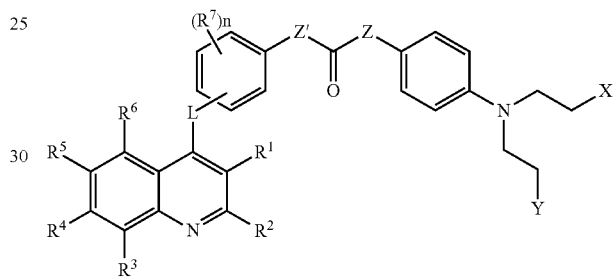

(I-B)

or a salt thereof;
wherein:
X and Y are independently selected from the group consisting of Cl, Br, I, and $OSO_2Me$;
Z is —NH or —O—;
Z' is —NH, —NHNH, —OCH$_2$—, or —O—;
L is —NH or —O—;
L is at the meta or para position corresponding to Z'.
each of $R^1$ and $R^2$ is independently selected from hydrogen, halogen, optionally substituted $C_1$-$C_6$ alkyl, optionally substituted alkenyl, optionally substituted alkynyl, optionally substituted heterocyclyl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^1$ and $R^2$ are taken together with their intervening atoms to form a carbocycle or heterocycle;
$R^3$, $R^4$, $R^5$ and $R^6$ are each independently selected from hydrogen, halogen, optionally substituted $C_1$-$C_6$ alkyl, optionally substituted alkenyl, optionally substituted alkynyl, optionally substituted heterocyclyl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^4$ and $R^5$ are taken together with their intervening atoms to form a carbocycle or heterocycle;
each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl;

each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle;

each $R^7$ is independently selected from halogen, optionally substituted $C_1$-$C_6$ alkyl, optionally substituted alkenyl, optionally substituted alkynyl, optionally substituted heterocyclyl, and optionally substituted aryl, —$OR^a$, —$CH_2OH$, —$NHCOR^a$, —$NHC(O)OR^a$, wherein $R^a$ is $C_1$-$C_6$ alkyl, phenyl, or benzyl;

n is 0-4.

In some embodiments, L is —NH. In some embodiments, L is —O—.

In some embodiments, L is at the meta position corresponding to Z'. In some embodiments, L is at the para position corresponding to Z'.

In some embodiments, X and Y are the same. In a preferred embodiment, X and Y are Cl.

In some embodiments, Z is —NH. In some embodiments, Z is —O—.

In some embodiments, Z' is —NH. In some embodiments, Z' is —NHNH. In some embodiments, Z' is —$OCH_2$—. In some embodiments, Z' is —O—.

Each of $R^1$, $R^2$, $R^3$, $R^4$, $R^5$ and $R^6$ is independently hydrogen, halogen, alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, or —$NHSO_2R^B$.

In certain embodiments, each of $R^1$, $R^2$, $R^3$, $R^4$, $R^5$ and $R^6$ is independently selected from —H, —OH, —Cl, —Br, —F, $C_{1-6}$ alkyl, $C_{1-6}$ alkoxy, alkynyl, aryl, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl.

In certain embodiments, each of $R^1$, $R^2$, $R^3$, $R^4$, $R^5$ and $R^6$ is independently selected from —H, —OH, —Cl, —Br, —F, methyl, ethyl, methoxy, ethoxy, —C≡C-aryl, phenyl, naphthyl, —$NO_2$, —NH—$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl.

In certain embodiments, each $R^7$ is independently selected from $C_1$-$C_6$ alkyl, —$OR^a$, —$CH_2OH$, —$NHCOR^a$, —$NHC(O)OR^a$, wherein $R^a$ is $C_1$-$C_6$ alkyl, phenyl, or benzyl;

In some embodiments, $R^4$ and $R^5$ are taken together with their intervening atoms to form a carbocycle. In certain embodiments, $R^4$ and $R^5$ are taken together with their intervening atoms to form a heterocycle.

In some embodiments, $R^1$ and $R^2$ are taken together with their intervening atoms to form a 6-membered aromatic ring, wherein the ring is unsubstituted or substituted by one or more R' groups; and R' is hydrogen, halogen, $C_1$-$C_6$ alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, the R' group is selected from hydrogen, methyl, methoxy, $CONHR^b$, and $CONH(CH_2)_nN(R^b)_2$, wherein each of $R^b$ is independently $C_1$-$C_6$ alkyl, and n is 1 to 6.

Examples of such compounds of Formula (I-B) include, but are not limited to, the following:

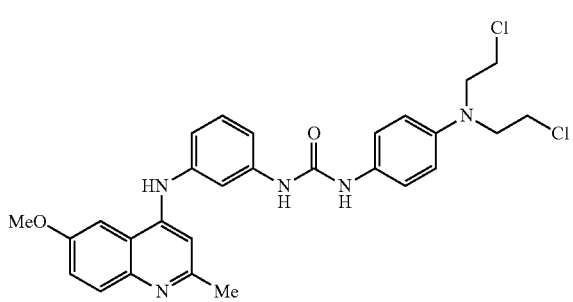

BO-1547

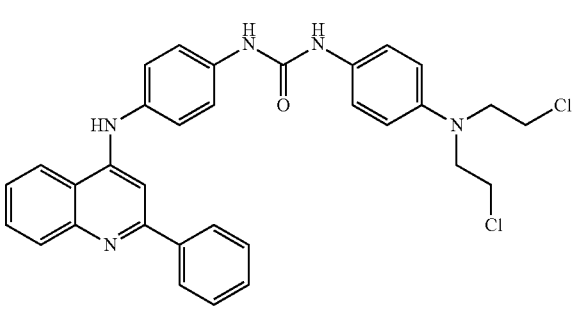

BO-2294

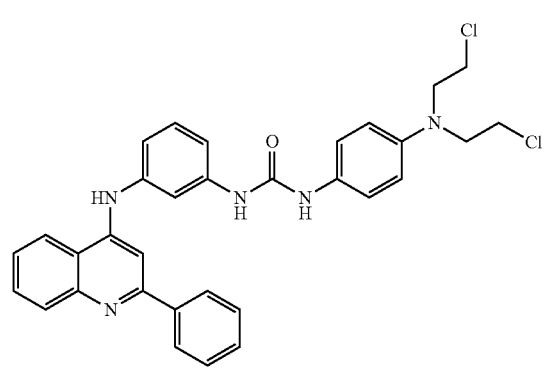

BO-2295

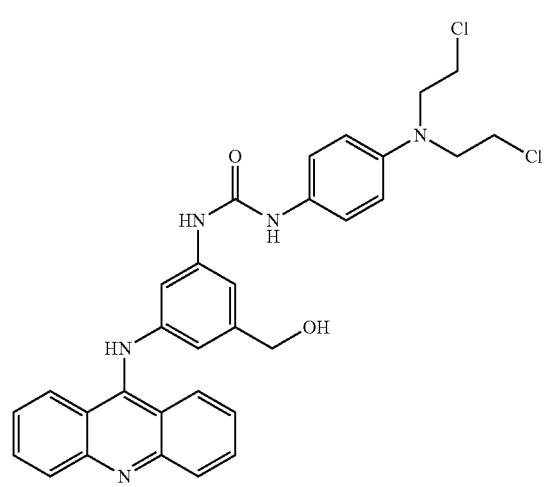

BO-1037

-continued
BO-1050
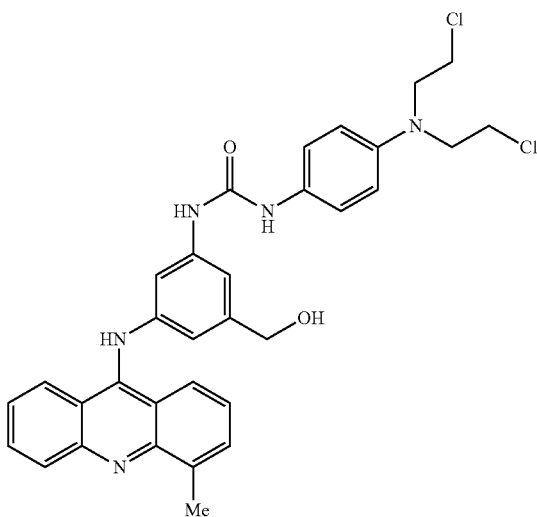
BO-1051
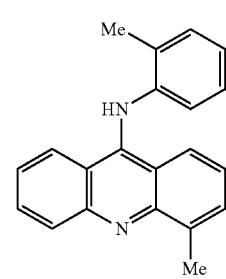
BO-1079
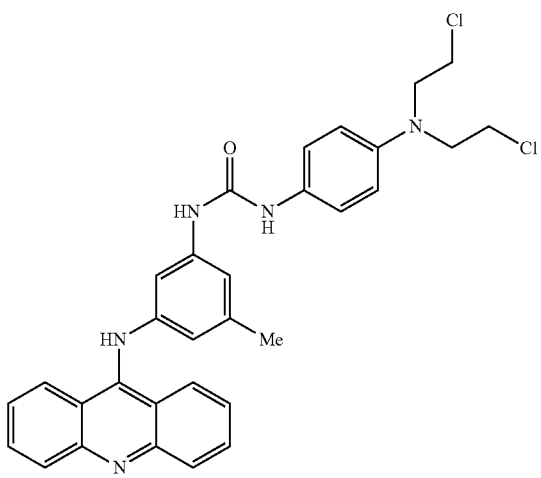
-continued
BO-1149
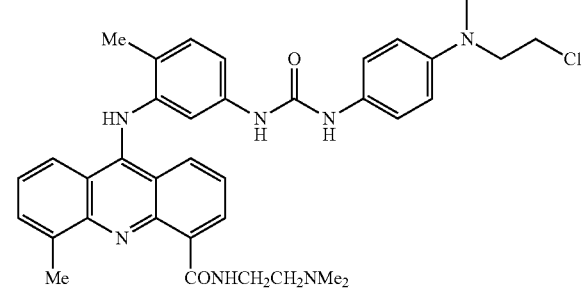
BO-1053
BO-1150
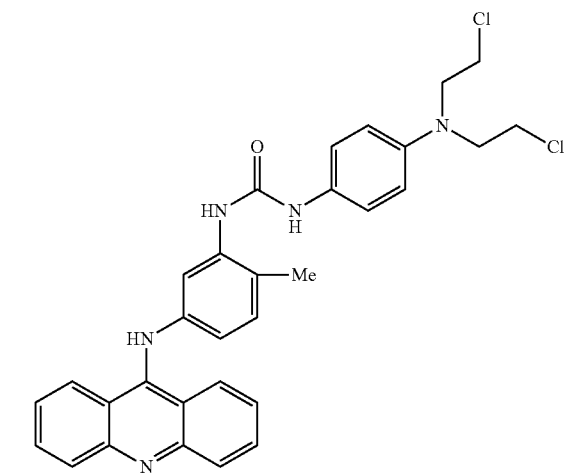

-continued
BO-1148
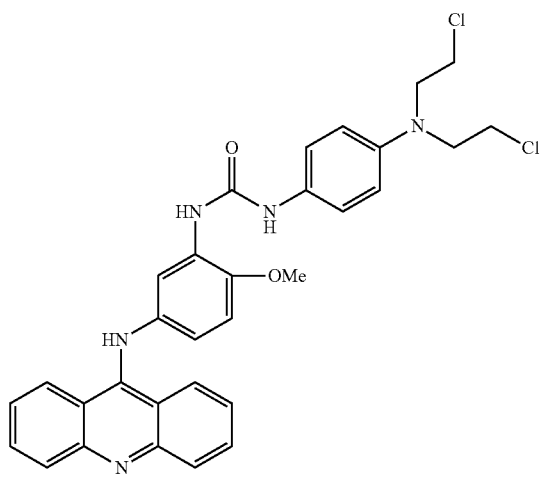
BO-1154
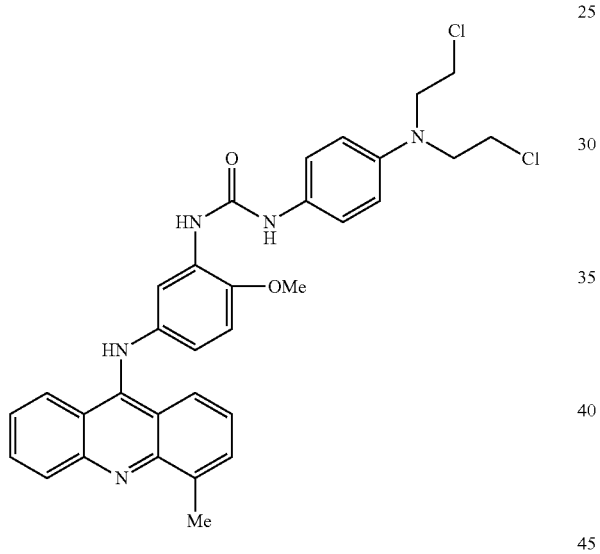
BO-1062
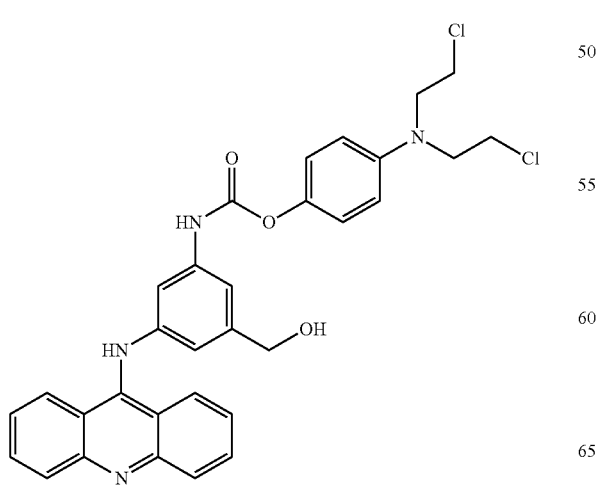
-continued
BO-1063
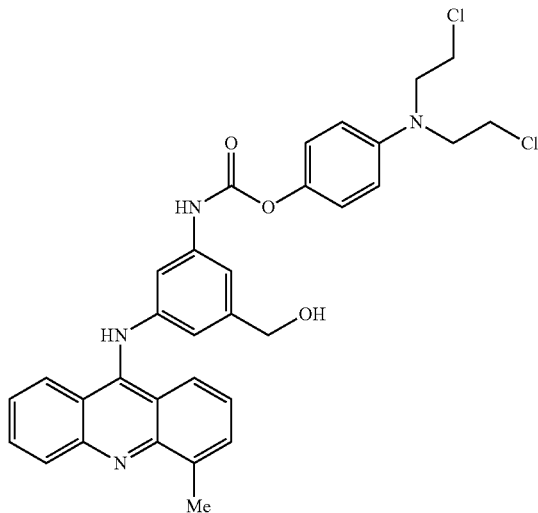
BO-1171
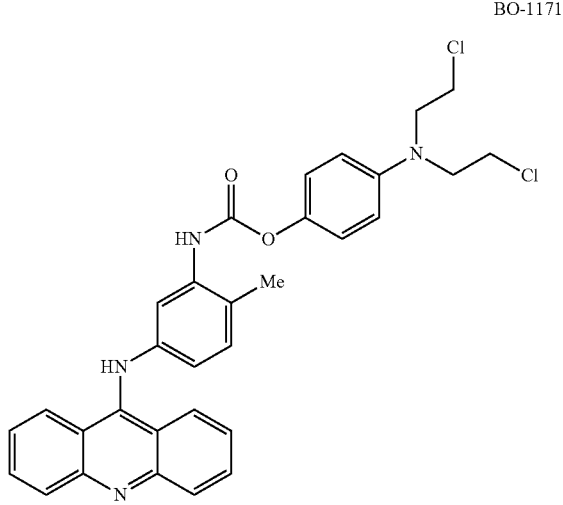
BO-1064
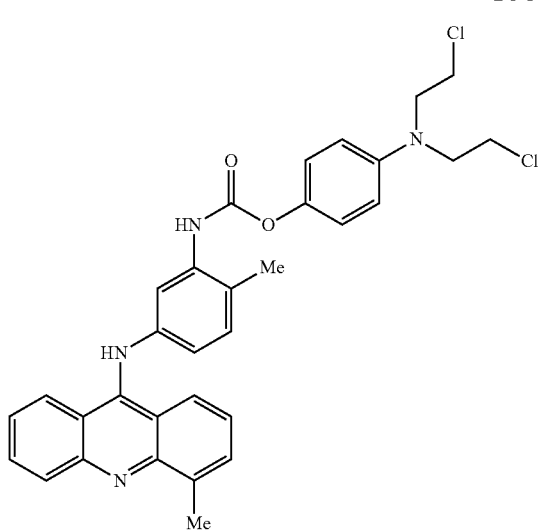

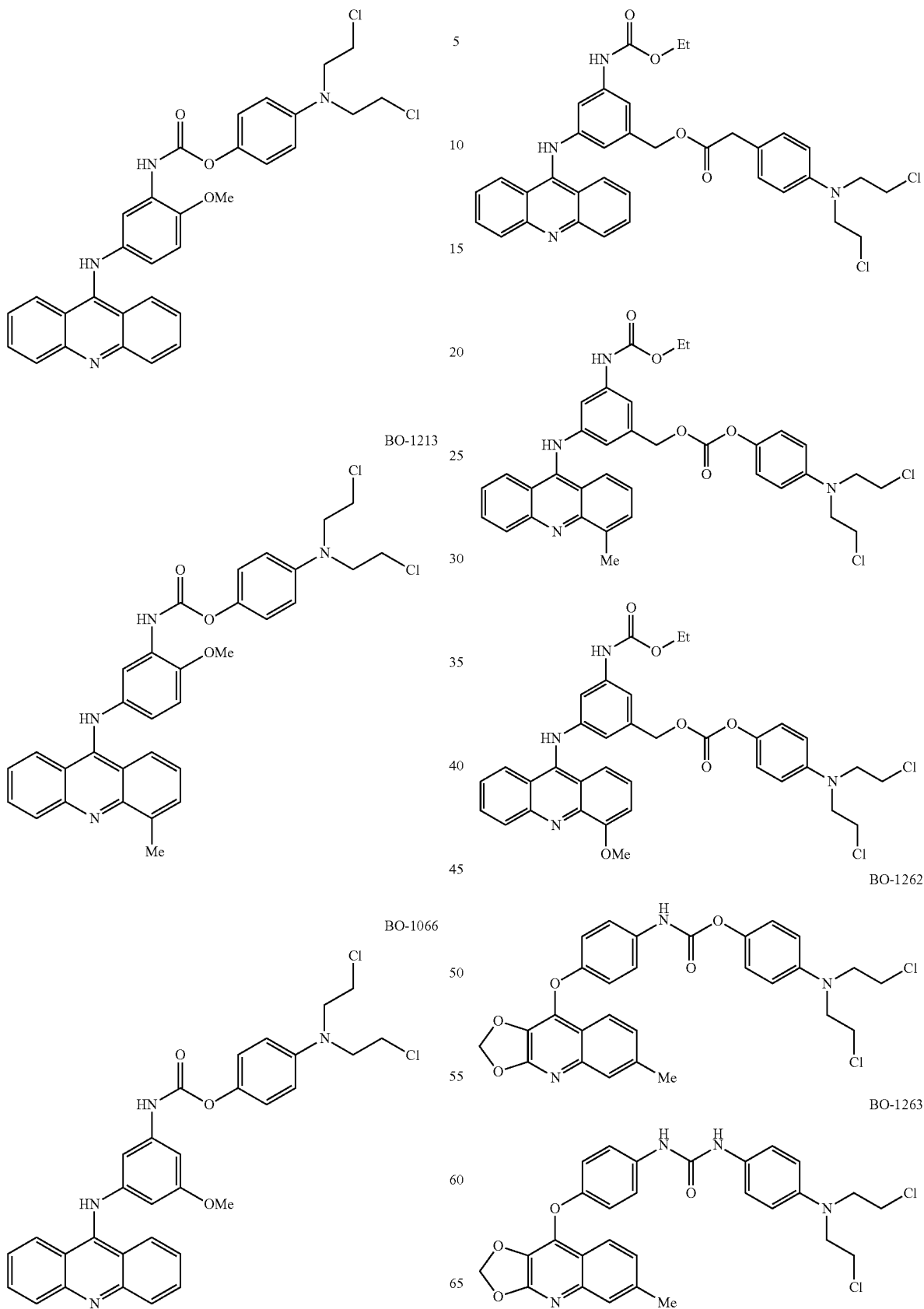

-continued

BO-1054

BO-1244

BO-1245

In yet another example, the N-mustard conjugate is of Formula (I-C):

(I-C)

or a salt thereof;

wherein:

X and Y are independently selected from the group consisting of Cl, Br, I, and $OSO_2Me$;

Z is —NH or —O—;

Z' is —NH, —NHNH, —$OCH_2$—, or —O—;

—NHC(O)R is at the meta or para position corresponding to Z'.

R is selected from optionally substituted $C_1$-$C_6$ alkyl, optionally substituted alkenyl, optionally substituted alkynyl, optionally substituted heterocyclyl, optionally substituted aryl.

In some embodiments, X and Y are the same. In a preferred embodiment, X and Y are Cl.

In some embodiment, Z is —NH.

In some embodiment, Z' is —NH.

In some embodiments, —NHC(O)R is at the meta position corresponding to Z'. In some embodiments, —NHC(O)R is at the para position corresponding to Z'.

In some embodiments, R is —$(CH_2)_n NR^1R^2$, wherein n is 1-6. In some embodiments, $R^1$ and $R^2$ are the same or independently, $C_1$-$C_6$ alkyl. In some embodiments, $NR^1R^2$ is a cyclic amine. In some embodiments, $NR^1R^2$ is selected from the group of morpholine, pyrrolidine, piperidine, 1-methylpiperazine and 4-piperidinopiperidine.

The —$(CH_2)_n NR^1R^2$ can be formed acid salts with various inorganic acids such as HCl, HBr, HI, $H_2SO_4$, or organic acid such as HCOOH, $CH_3COOH$, citric acid, oxalic acid, tartaric acid, methanesulfonic acid, phenylsulfonic acid, toluenesulfonic acid.

Examples of such compounds of Formula (I-C) include, but are not limited to, the following:

BO-2189

BO-2183

BO-2091
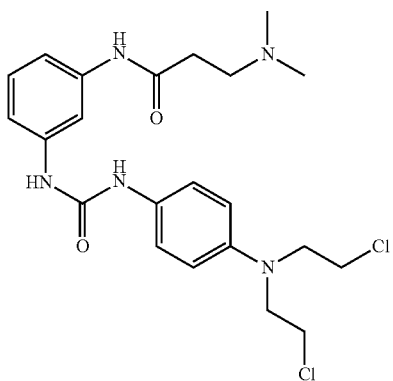
BO-2151
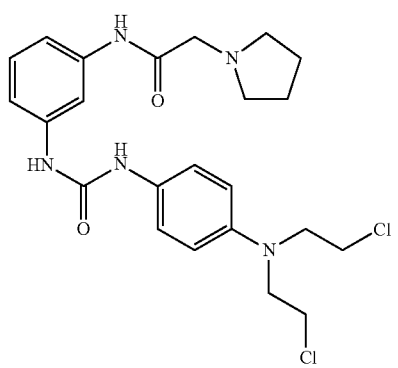
BO-2120
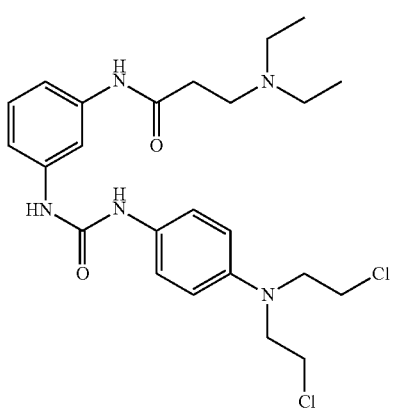
BO-2121
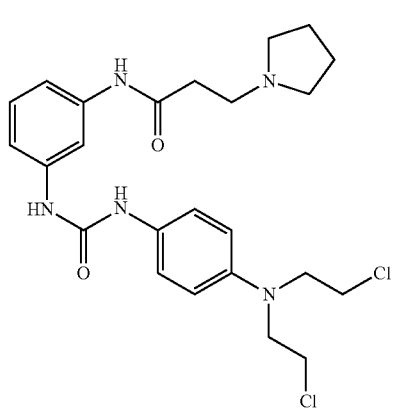
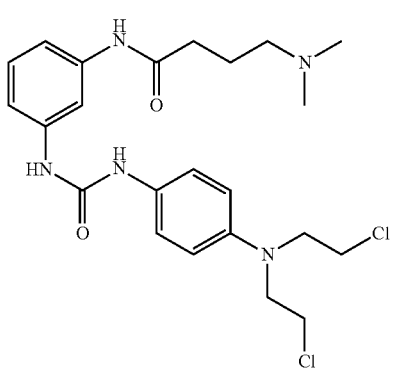
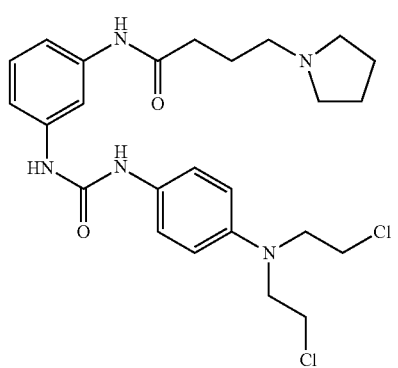
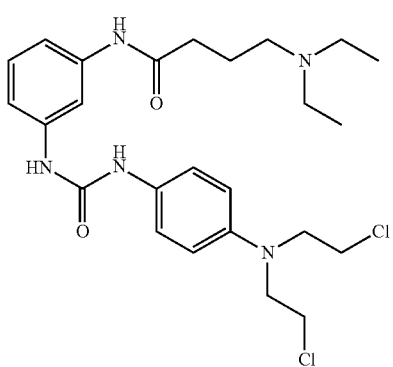
BO-2184
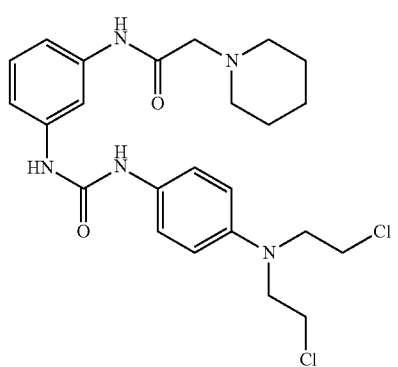

27
-continued
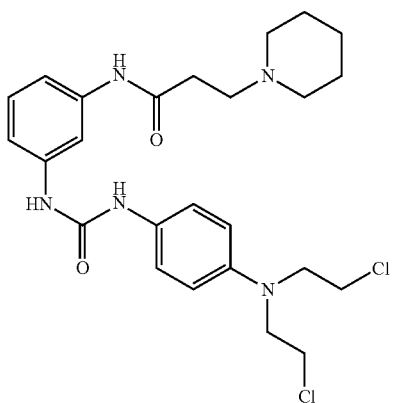
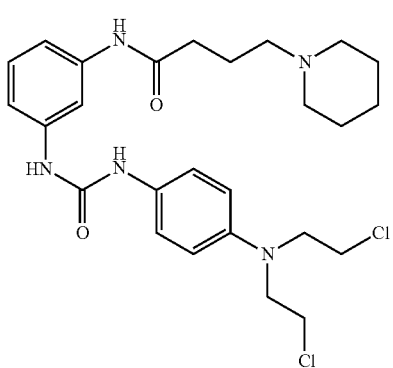
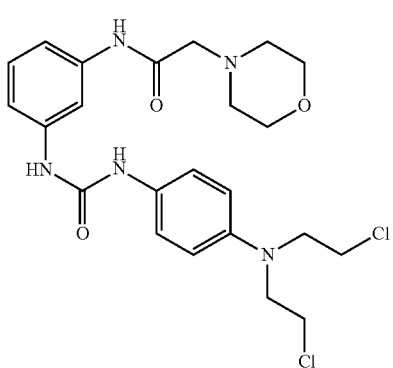
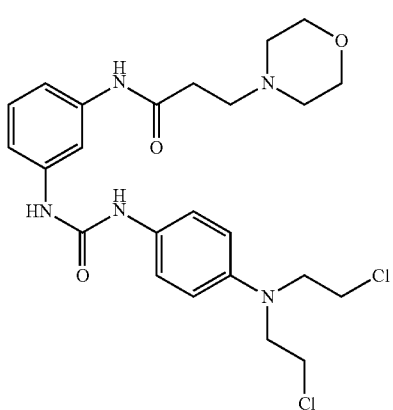
28
-continued
BO-2147
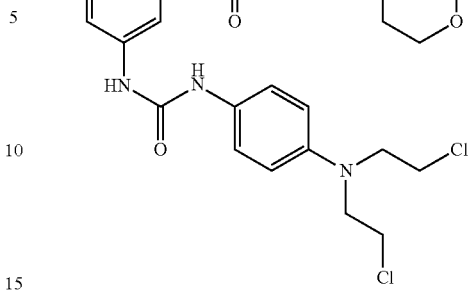
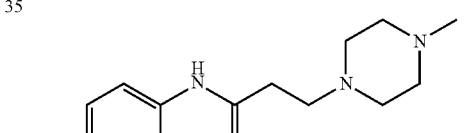
BO-2182
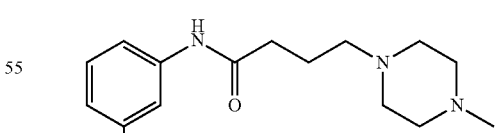
BO-2148

BO-2188
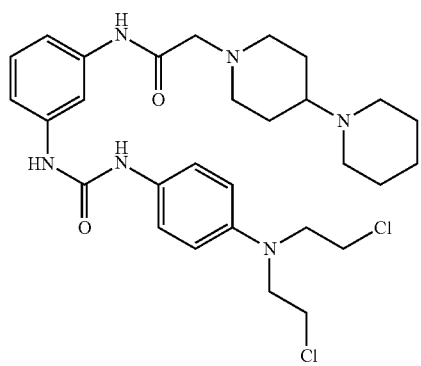
BO-2191
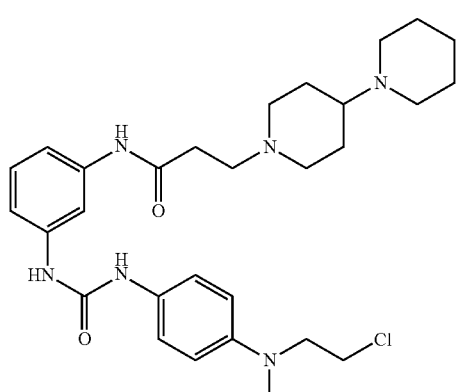
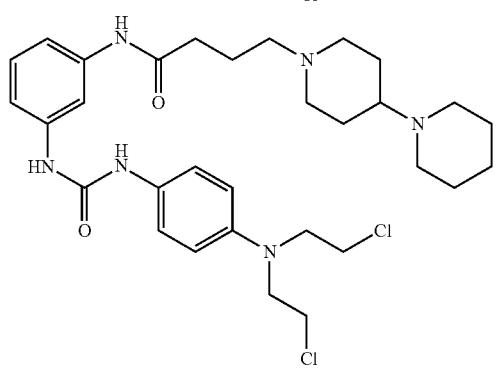
BO-2095
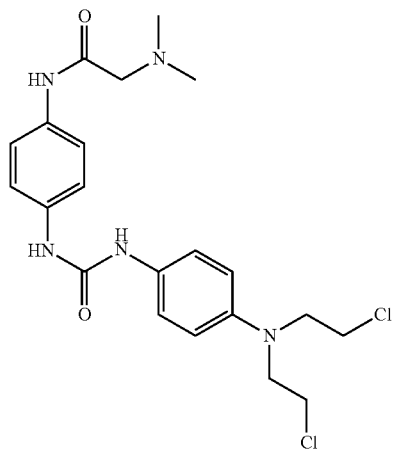
BO-2094
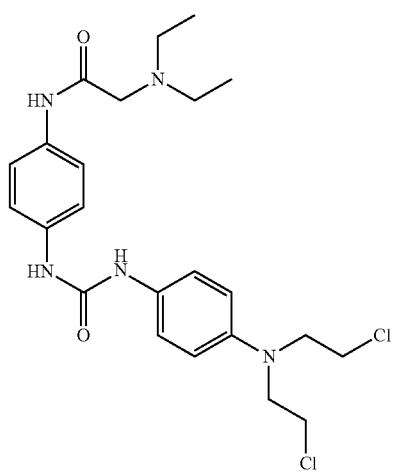
BO-2060
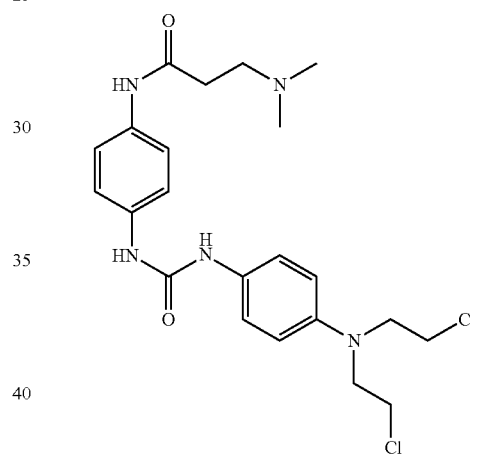
BO-2073
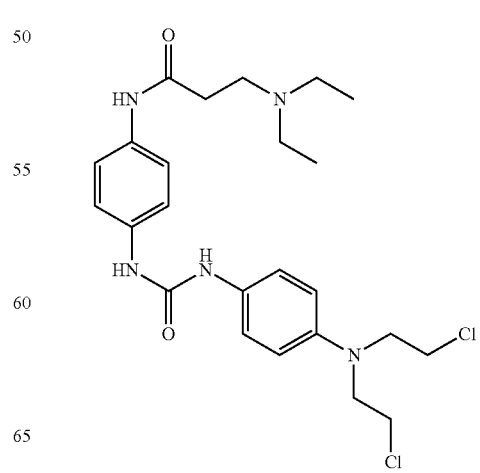

31
-continued
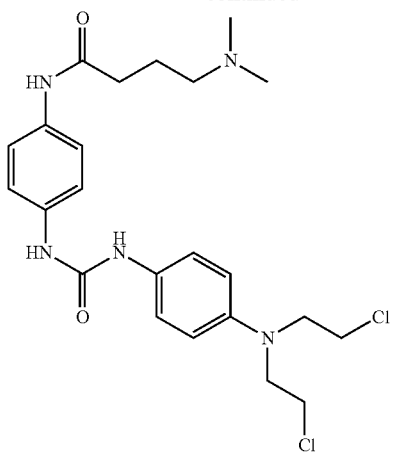
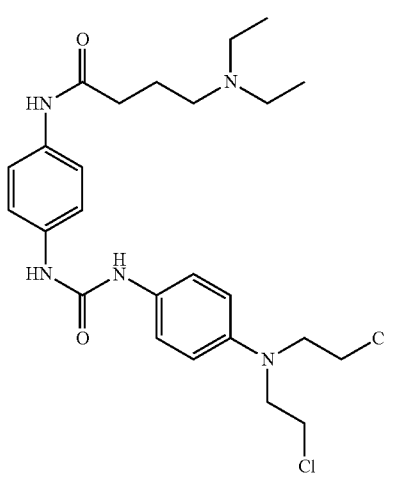
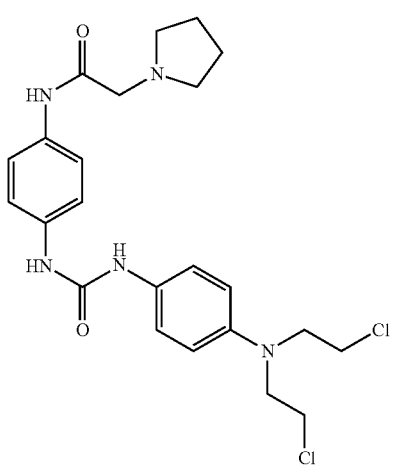
BO-2093
32
-continued
BO-2075
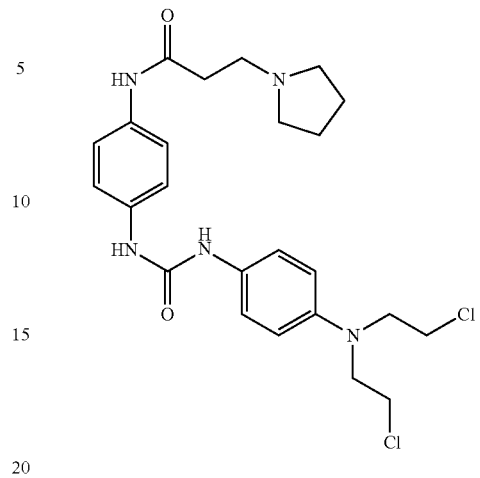
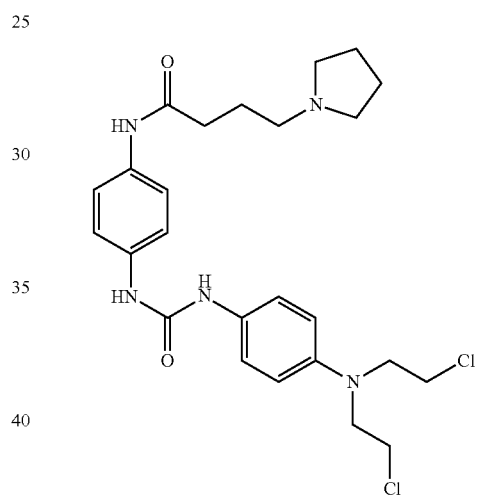
BO-2092
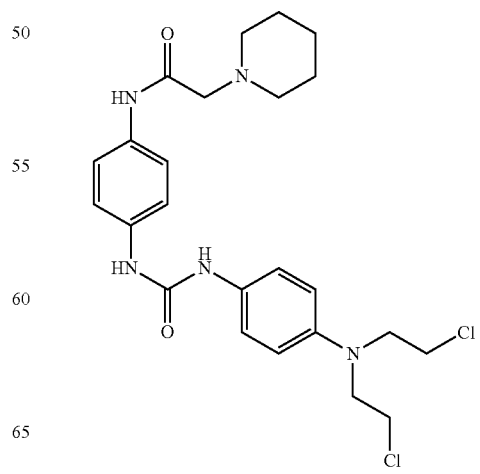

BO-2057
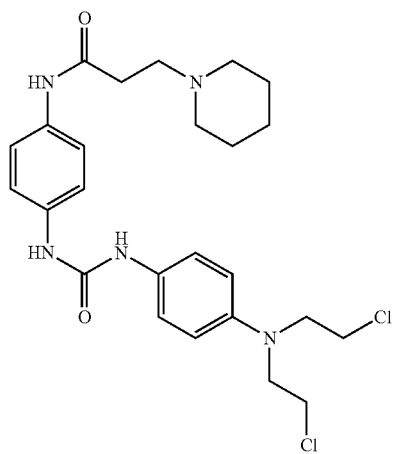
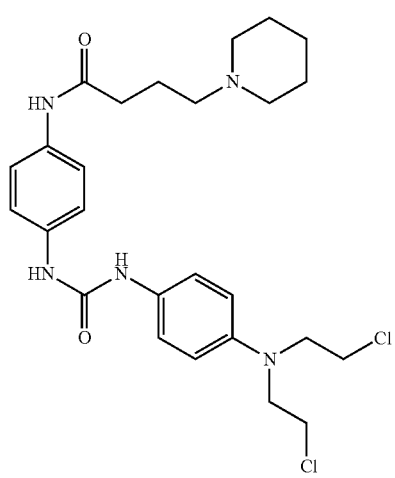
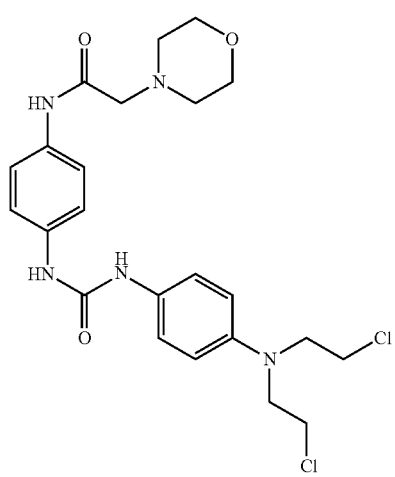
BO-2074
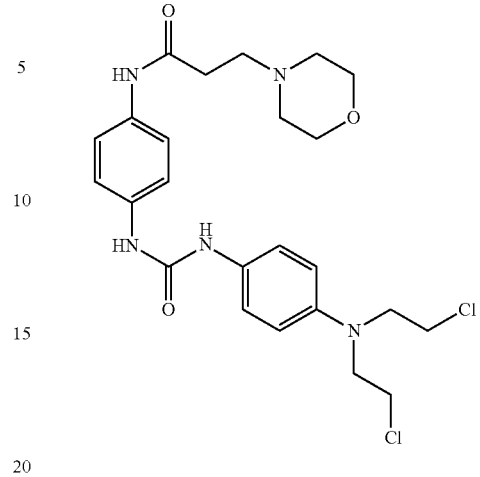
BO-2096
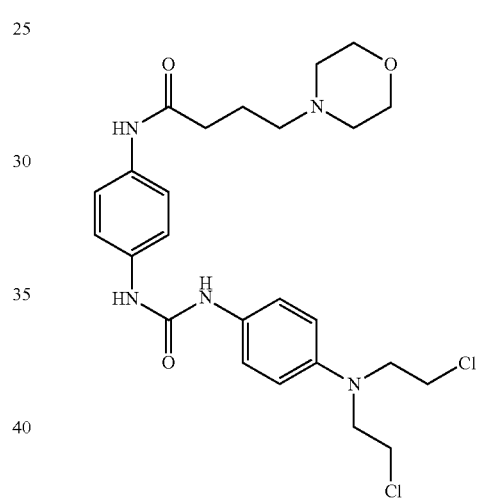

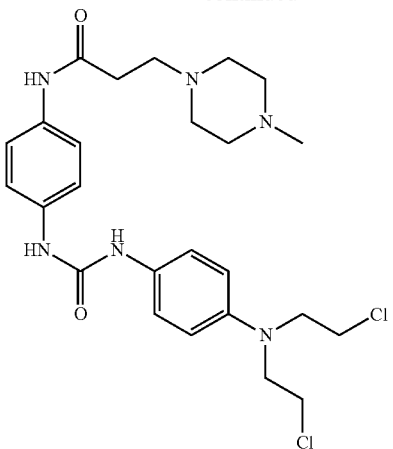

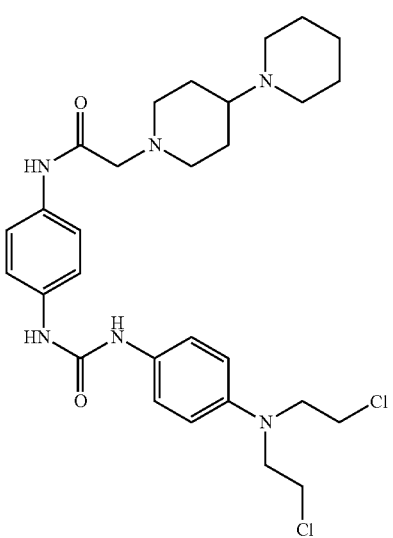

BO-2117

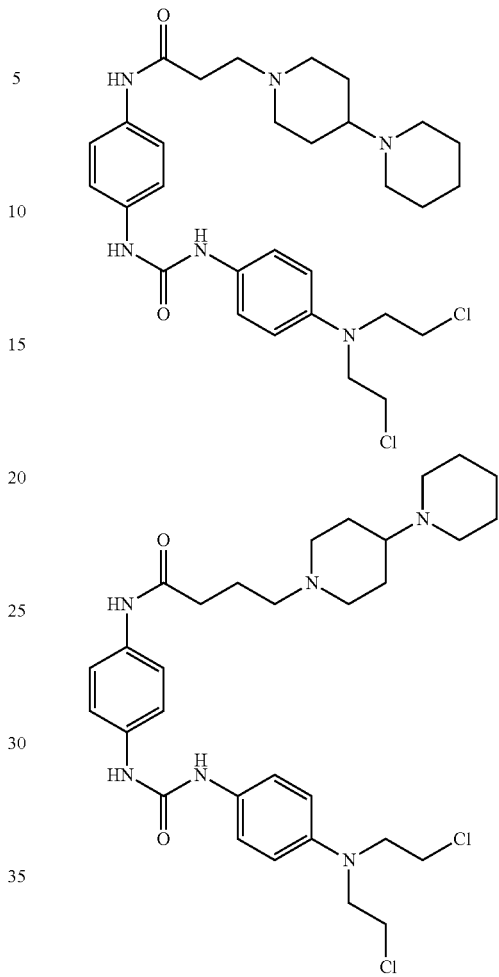

BO-2118

The compounds included in this new invention can be synthesized using conventional techniques. Advantageously, these compounds are conveniently synthesized from readily available starting materials and standard organic chemistry synthesis methods, including those methods illustrated in the schemes and the examples herein.

II. Methods of Cancer Treatment

The novel N-mustard conjugates of Formula (I) disclosed herein can be used to treat various types of cancers including, but not limited to, breast cancer, hepatocellular carcinoma, prostate cancer, lung cancer, ovarian cancer, kidney cancer, uterine cervical cancer, melanoma, embryonal carcinoma, leukemia, osteosarcoma, brain cancer, nasal cancer, pharyngeal cancer, head cancer, neck cancer, bladder cancer, pancreatic cancer, stomach cancer, colon cancer, skin cancer, colorectal, lymphoma, gastric cancer, or leukemia.

To practice these treatments, one can contact cancer cells with an effective amount of a compound of Formula (I) as described herein. In some embodiments, this is performed by administering the compound to an organism in need of the treatment. In some embodiments, the treatment is carried out in vitro. In some embodiments, the treatment is carried out in vivo. The organism is an animal or a human.

The subject in need of the treatment can be a human patient has or is suspected of having cancer including, but not limited to, breast cancer, hepatocellular carcinoma, prostate cancer, lung cancer, ovarian cancer, kidney cancer, uterine cervical cancer, melanoma, embryonal carcinoma, leukemia, osteosarcoma, brain cancer, nasal cancer, pharyngeal cancer, head cancer, neck cancer, bladder cancer, pancreatic cancer, stomach cancer, colon cancer, skin cancer, colorectal, lymphoma, gastric cancer, or leukemia.

The anti-cancer agents can be mixed with a pharmaceutically acceptable carrier to form a pharmaceutical composition. The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the anti-viral agents described herein, or more solubilizing agents, can be utilized as pharmaceutical carriers for delivery of the anti-viral agents. Examples of other carriers include colloidal silicon dioxide, magnesium stearate, sodium lauryl sulfate, and D&C Yellow #10. See, e.g., Remington's Pharmaceutical Sciences, Edition 16, Mack Publishing Co., Easton, Pa. (1980); and Goodman and Gilman's "The Pharmacological Basis of Therapeutics", Tenth Edition, Gilman, J. Hardman and L. Limbird, eds., McGraw-Hill Press, 155-173, 2001.

To practice the method of this invention, the above-described compounds or its pharmaceutical compositions can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation.

EXAMPLES

The specific examples below are to be constructed as merely illustrative, and not limitative of the remainder of the disclosure in any way whatsoever.

Example 1

Chemical Synthesis of New N-Mustard Conjugates

1. Preparation of 4-[N,N-bis(2-chloroethyl)amino]phenylisocyanate (19)

The known compound phenylisocyanate N-mustard 19 can be prepared by following the literature procedure[35,36] with modification (Scheme 3). The commercially available 4-fluoronitrobenzene (15) is reacted with diethanolamine under refluxing to give 4-[N,N-bis(2-hydroxyethyl)amino]nitrobenzene (16), which is then converted to 4-[N,N-bis(2-chloroethyl)amino]nitrobenzene (17) by treating with thionyl chloride. Catalytic hydrogenation (10% Pd/C, $H_2$) of compound 17 in ethyl acetate affords N,N-bis(2-chloroethyl)benzene-1,4-diamine (18), which is immediately treated with HCl in ethyl acetate to yield hydrochloride salt of 18. The hydrochloride salt 18 is suspended in $CHCl_3$ and cooled in an ice-bath. To the suspension is added triethylamine and stirred in Argon atmosphere for 5 to 10 min. and then is added dropwise triphosgene solution in $CHCl_3$ and continuously stirred for 20 min. The reaction mixture is evaporated under reduced pressure and the residue is the triturated with THF, filtered and the filtrate containing phenylisocyanate 19, which is used directly for the next reaction without purification. Compound 18 and 19 can be used for the synthesis of the newly invented compounds.

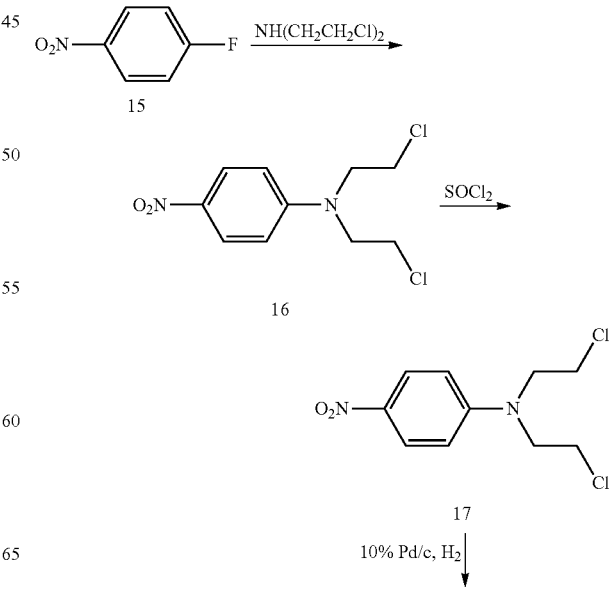

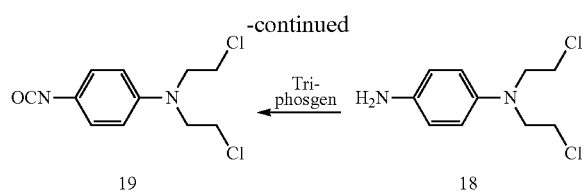

2. Synthesis of 4-[N,N-bis(2-chloroethyl)aminophenyl-4-nitrophenyl carbonate (30)

Phenol N-mustard is synthesized by to known procedures with modification. Scheme 4 shows the synthetic route for phenol mustard. Treatment of 4-nitrophenol (20) with benzyl chloride or 4-fluoro-1-nitrobenzene (22) with benzyl alcohol in the presence of base (such as NaOH, KOH, $Na_2CO_3$, $K_2CO_3$ or organic base) gives compound 21, which is converted into 4-benzyloxyaniline (23) by reduction (Fe/$CH_3COOH$ or Pd/C, $H_2$). Treatment of 23 with ethylene oxide affords 4-N,N-bis(2-hydroxyethyl)aminophenyl benzyl ether 24.[37]

Alternatively, the intermediate 24 can be prepared by reacting 4-hydroxyaniline (25) with 2-chloroethanol in the presence of $Na_2CO_3$ followed with benzyl bromide.[38] Treatment of 24 with thionyl chloride (or $POCl_3$, methanesulfonyl chloride/pyridine, and other halogenating reagents) yields 4-N,N-bis(2-chloroethyl)aminophenyl benzyl ether 27. The O-benzyl protecting function of 27 is removed by catalytic hydrogenation or by treating with HCl/$CH_3COOH$ to give the desired phenol mustard 28, which is then treated with phosgene affords 4-[bis(2-chloroethyl)amino]phenyl-chloridocarbamate (29). One can also convert 28 to 4-[N,N-bis(2-chloroethyl)aminophenyl-4-nitrophenyl carbonate (30) by reacting with p-nitrochloroformate/$Et_3N$ to yield 4-[N,N-bis(2-chloroethyl)aminophenyl-4-nitrophenyl carbonate (30).[39-41] Both 19 and 30 can be used for the synthesis of the target compounds having a carbamic acid ester linkage.

Scheme 4

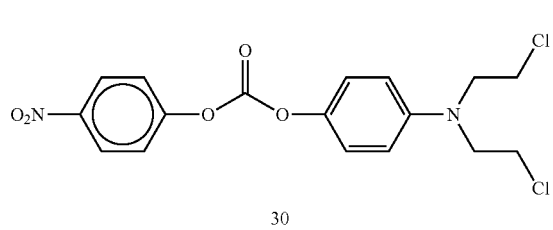
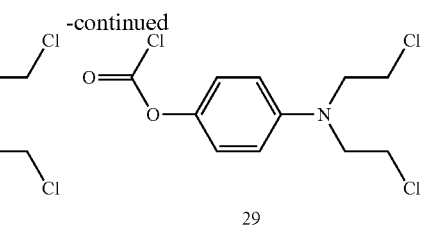
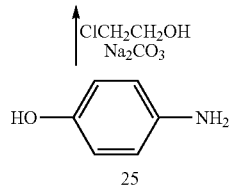

3. Synthesis of 4-aminoquinoline derivatives (33)

4-Aminoquinolines used for the synthesis of compounds of Formula (I-A) can be synthesized starting from quinolin-4-ones, which can be prepared by methods described in literatures[42,43,44] (Scheme 5). Treatment of quinolin-4-ones (31) with phosphorus oxychloride (or thionyl chloride) gives 4-chloroquinolines (32), which is further reacted with a mixture of phenol and ammonia at 180° C. to afford 4-aminoquinolines (33).

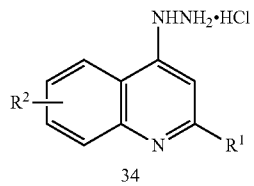

$R^1$ = Me or substituted benzenes (i.e., 3'-MeOC$_6$H$_4$, 2'-FC$_6$H$_4$, 3'-ClC$_6$H$_4$, etc.
$R^2$ = H, F, Cl, Me, OMe, NMe$_2$ or cyclic amine

5. Synthesis of 4-quinolyloxyaniline derivatives (36)

4-Quinolyloxy anilines (36) used for preparing compounds of Formula I-B can be prepared by the reaction of 4-chloroquinolines (32) with 3- or 4-nitrophenol at 140-150° C. to give 4-(4-nitrophenoxy)quinolines derivatives (35) by following procedure described previously.[49-51] The nitro group in 35 is reduced (Pd/C/H$_2$ or Zn/MeOH/reflux) to yield the corresponding anilinine derivatives 36 (Scheme 7).

Scheme 5

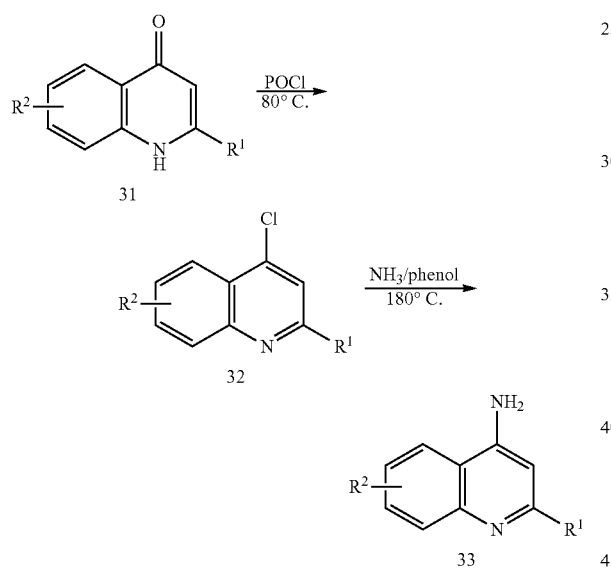

Scheme 7

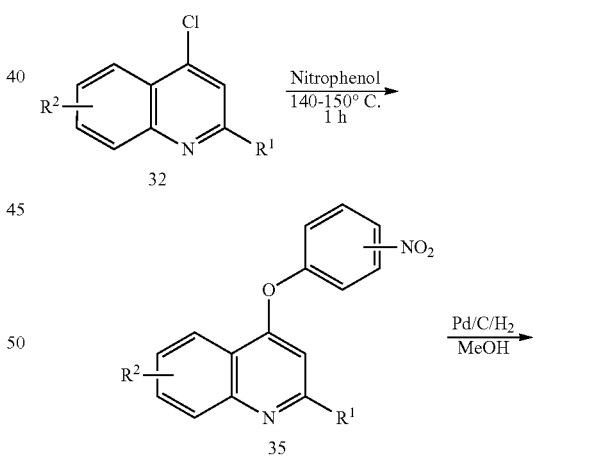

4. Synthesis of 4-quinolylhydrazone derivatives (34)

4-Quinolylhydrazones used for the synthesis of compound of Formula I-A can be synthesized starting from 4-chloroquinolines (32) according to the literature procedures.[45-48] A mixture of 4-chloroqinolines (32) and 80% hydrazine hydrate aqueous solution will be refluxed in ethanol to afford 4-quinolylhydrazones (34) (Scheme 6).

Scheme 6

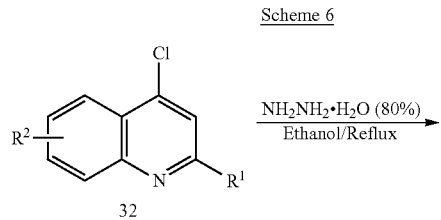
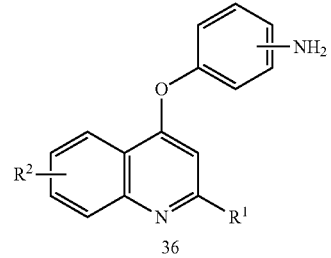

$R^1$ = Me or substituted benzenes (i.e., 3'-MeOC$_6$H$_4$, 2'-FC$_6$H$_4$, 3'-ClC$_6$H$_4$, etc.
$R^2$ = H, F, Cl, Me, OMe, NMe$_2$ or cyclic amine

6. Synthesis of 4-anilinoquinline derivatives (38)

4-Anilinoquinline derivatives (38) used for preparing compounds of Formula I-B can be prepared by the reaction of 4-chloroquinolines (32) with the commercially available 3- or 4-nitroaniline (37a, and 37b, respectively) at 140-150° C. to give 4-(4-nitroanilino)quinolines derivatives (38) by following procedure described previously.[49-51] The nitro group in 38 is reduced (Pd/C/H$_2$ or Zn/MeOH/reflux) to yield the corresponding anilinine derivatives 39 (Scheme 8).

Scheme 8

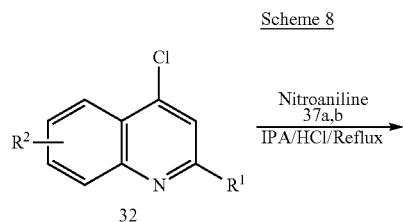

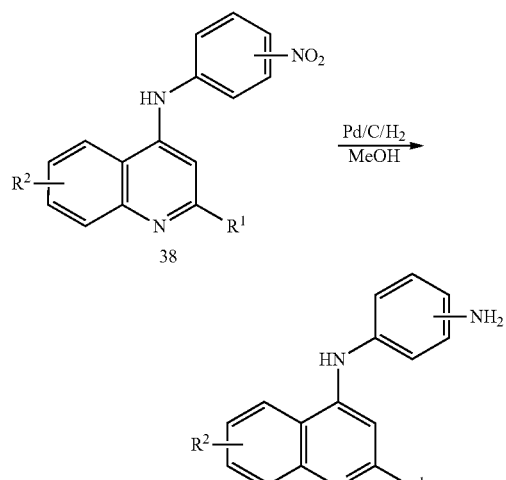

$R^1$ = Me or substituted benzenes (i.e., 3'-MeOC$_6$H$_4$, 2'-FC$_6$H$_4$, 3'-ClC$_6$H$_4$, etc.
$R^2$ = H, F, Cl, Me, OMe, NMe$_2$ or cyclic amine

7. Synthesis of Compounds of Formulae (I-A) and (I-B) Containing a Urea or Carbamic Acid Ester Linkage Compounds of Formula (I-A) and (I-B) can be prepared by reacting 4-aminoquinolines (33), 4-hydrazinoquinoline (34), 4-phenoxyquinolines (36), or 4-anilinoquinoline (39) with N-mustards (i.e., 19 or 30) in a proper solvent (such as CHCl$_3$, THF, dioxane or DMF) in the presence of base (such as pyridine, triethylamine, DMAP, etc.) at room temperature to 60° C. as shown in Schemes 9 and 10.

Scheme 9

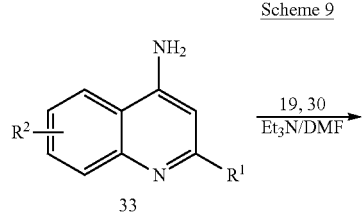

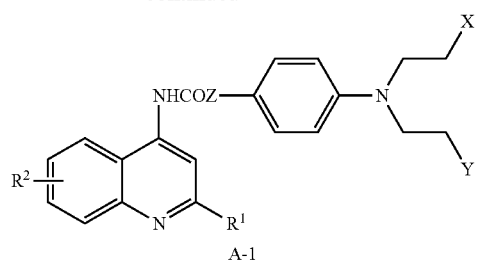

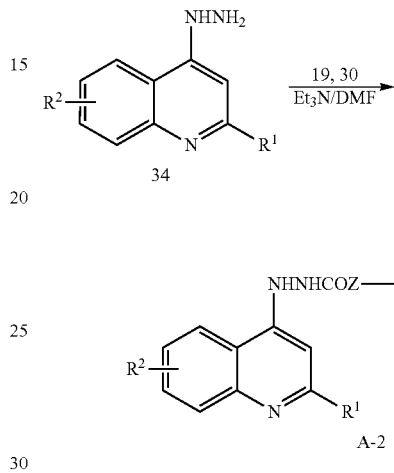

Scheme 10

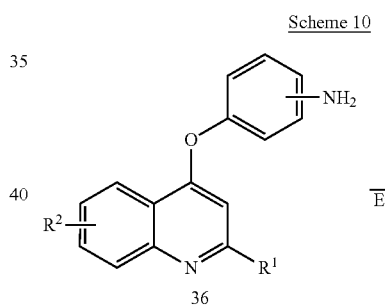

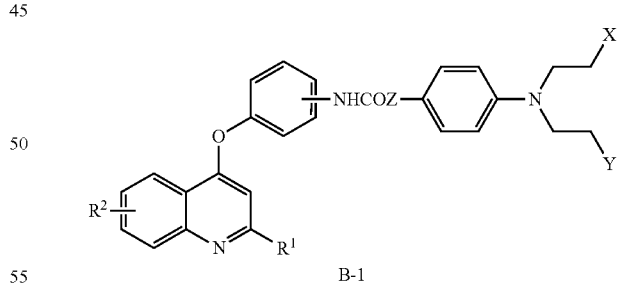

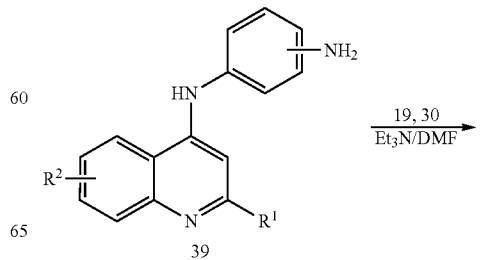

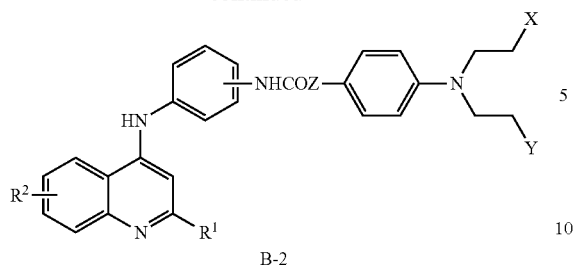

B-2

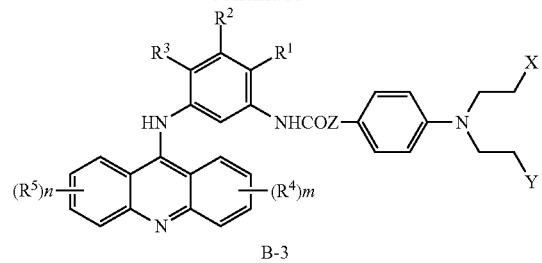

B-3

8. Synthesis of Compounds of Formulae (I-C) and (I-D) Containing a Urea or Carbamic Acid Ester Linkage Compounds of Formula (I-C) and (I-D) can be prepared by reacting 9-aminoacridines (40) or 9-anilinoacridines (41, 42, and 43) with phenyl N-mustards (19 or 30) in a proper solvent (such as CHCl$_3$, THF, dioxane or DMF) in the presence of base (such as pyridine, triethylamine, DMAP, etc.) at room temperature to 60° C. as shown in Schemes 11 and 12.

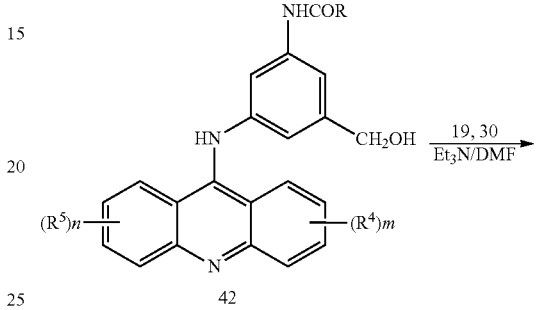

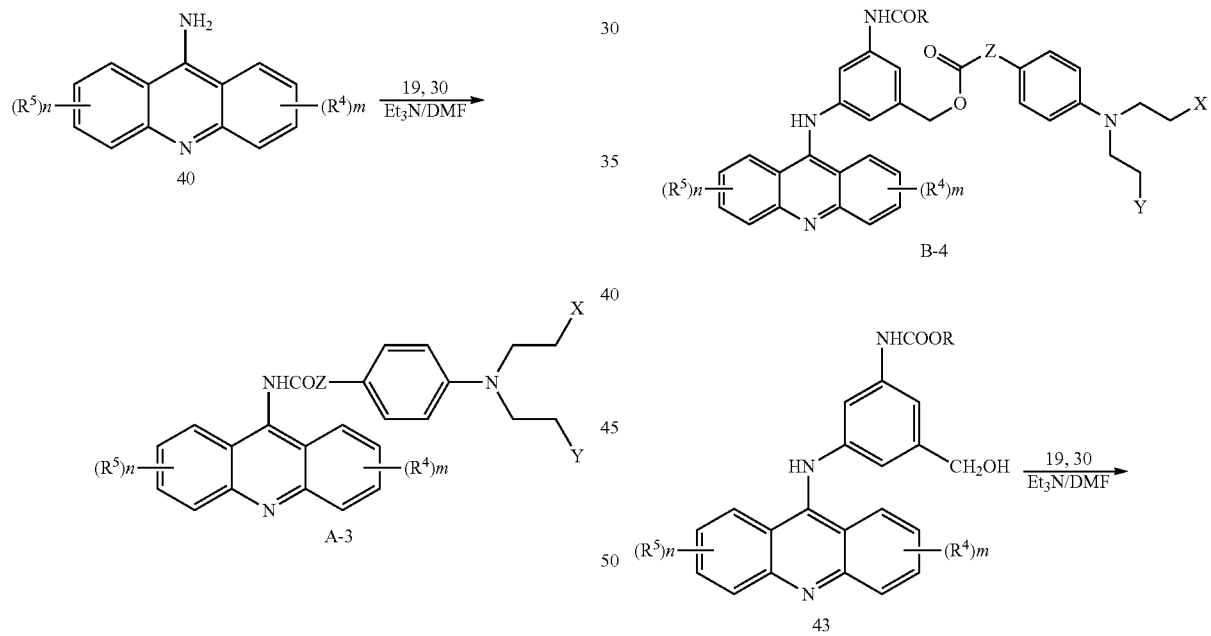

Scheme 11

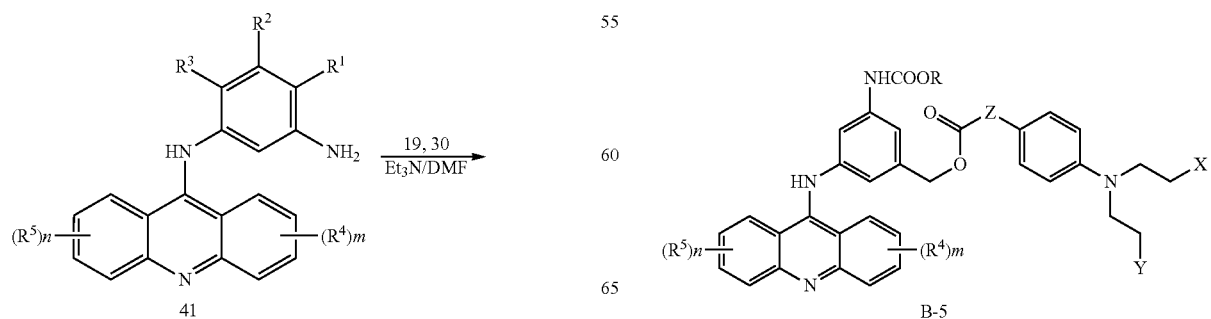

Scheme 12

9. Synthesis of Compounds of Formulae (I-E) by Method A or B

Method A

The phenyl N-mustard 18 is reacted with the commercially available 3- or 4-nitrophenyl isocyanate (44a or 44b, respectively) in $CHCl_3$ in the presence of base (such as triethylamine, TEA) will give compound 45a,b as shown in Scheme 13. The nitro function in 45a,b is reduced to aniline derivatives 46a,b by catalytic hydrogenation (10% Pd/C, $H_2$, EtOAc, at 35-38 psi). Compounds 46a,b are then reacted with various ω-haloalkyl carboxylic acid chlorides (47) in THF at 50° C. afford compounds 48, which are then reacted with various N,N-dialkylamines or cyclic amines (49) to give the desired target compounds of Formula I-E. Compounds of Formula I-E can be converted into water-soluble by treating with inorganic acid (such as HCl, HBr, $H_2SO_4$, etc.) or organic acid (such as toluenesulfonic acid, methanesulfonic acid, citric acid, etc.)

Method B

Alternatively, compounds of Formula I-E can be prepared by reacting 3- or 4-nitroaniline (37a,b) with various ω-haloalkyl carboxylic acid chloride (47) in $CHCl_3$ at room temperature to afford compounds 50, which are then reacted with various N,N-dialkylamines or cyclic amines (49) to give intermediates 51 (Scheme 14). The nitro function in 51 is then reduced to the amino derivatives 52. Condensation of 52 with phenyl isocyanate 19 can yield the desired compounds of Formula I-E.

Scheme 13

Reaction conditions: a) TEA, RT; b) 10% Pd/c, $H_2$, EtOAc, 35-38 psi; c) Acid chloride, THF, 50° C.; d) Different secondary amine, THF

Scheme 14

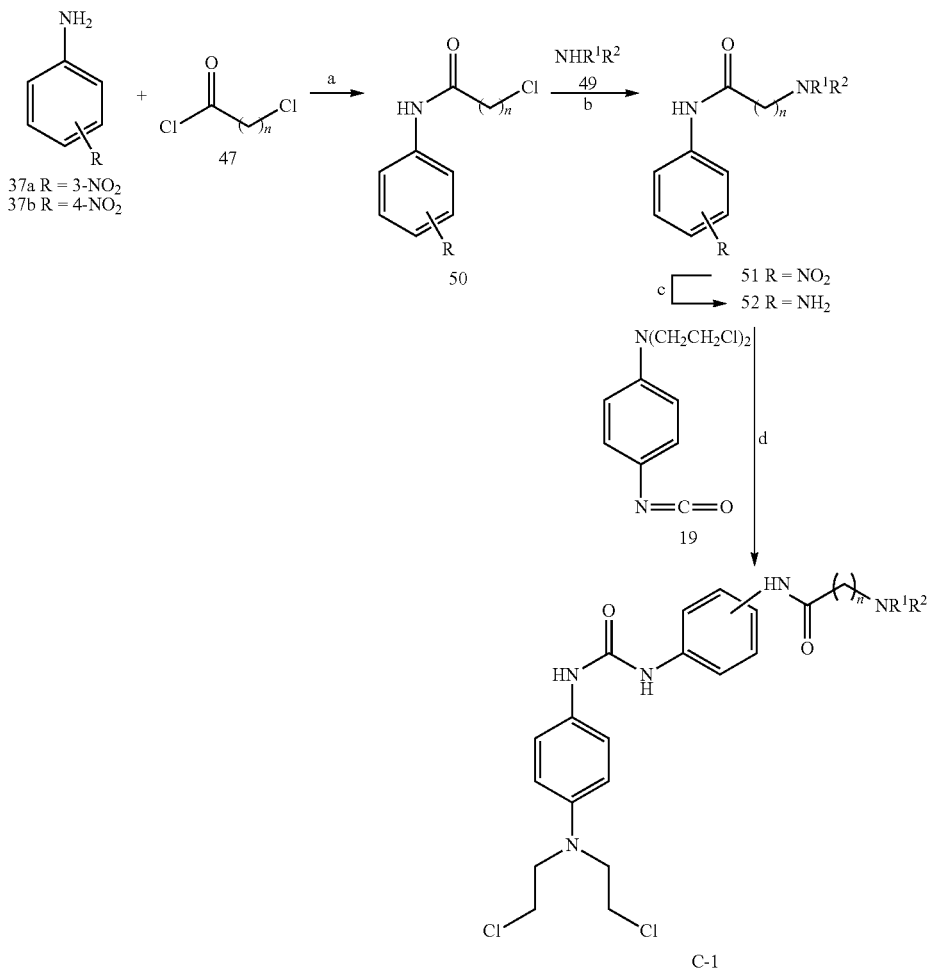

Reaction conditions: a) 50-60° C.; b) Different secondary amine, THF, RT; c) 10% Pd/c, H₂, EtOAc, 35-38 psi; d) TEA, DMF, RT

Example 2

Newly Invented N-Mustard Conjugates

Compound BO-1038

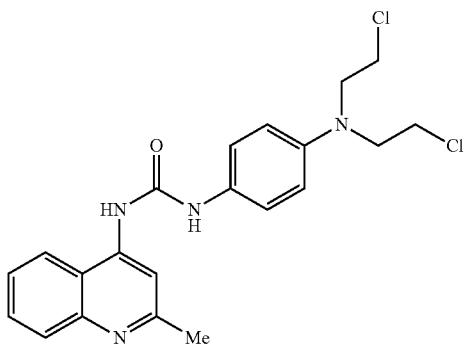

BO-1038

To a solution of N,N-bis(2-chloroethyl)benzene-1,4-diamine hydrochloride (18, 0.612 g, 2.0 mmol) in dry $CHCl_3$ (35 mL) containing $Et_3N$ (0.4 mL) was added dropwise a solution of triphosgene (231 mg, 0.8 mmol.) in an ice bath with vigorous stirring for 30 min. The reaction mixture was evaporated and the residue diluted with THF (20 mL), filtered through a pad of Celite, washed with THF (5 mL). The filtrate and washings were combined and then added dropwise into a solution of commercially available 4-amino-2-methylquinoline (0.177 g, 2.0 mmol) in dry DMF (15 mL) containing $Et_3N$ (0.5 mL) at 0° C. After being stirred at room temperature for 3 h, the reaction mixture was heated at 40-45° C. for 16 h and then evaporated in vacuo to dryness. The residue was dissolved in a mixture of $CHCl_3$/MeOH, mixed silica gel (10 g) and then evaporated in vacuo to dryness. The residue was put on the top of a silica gel column (2×30 cm) and chromatographed using $CHCl_3$/MeOH (100:2 v/v) as eluent. The fractions containing the main product were combined and evaporated in vacuo to dryness and the residue was recrystallized from acetone to give 1-{4-[bis(2-chloroethyl)amino]phenyl}-3-(2-methylquinolin-4-yl)urea (BO-1038); 187 mg (40.1%); mp 128-129° C.; $^1$H NMR ($CHCl_3$-$d_6$) δ 2.63 (3H, s, Me), 3.57 (4H, t, J=6.6 Hz, 2×$CH_2$), 3.66 (4H t, J=6.6 Hz, 2×CH$_2$), 6.56 (2H, d, J=7.9 Hz, 2×ArH), 7.12-7.14 (1H, m, ArH), 7.21 (2H, d, J=8.8 Hz, 2×ArH), 7.26 (1H, s, ArH), 7.44-7.56 (2H, m, 2×ArH), 7.92 (2H, d, J=8.5 Hz, 2×ArH), 8.14 (1H, s, ArH), 8.40 (1H, brs, exchangeable, NH). Anal. Calcd. for (C$_{21}$H$_{22}$Cl$_2$N$_4$O): C, 57.94; H, 5.56; N, 12.87. Found: C, 58.27; H, 5.56; N, 12.6.

Compound BO-1049

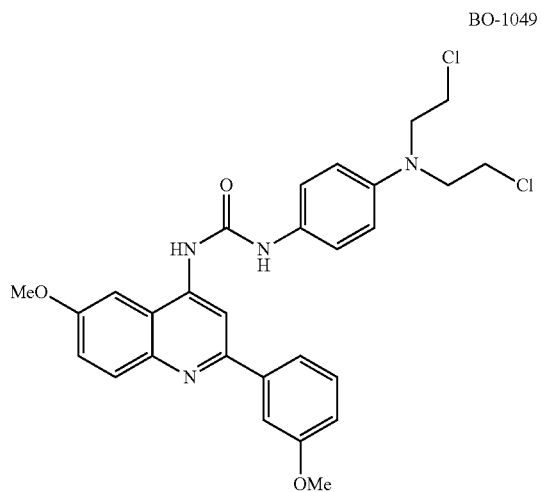

BO-1049

1) Preparation of 4-chloro-6-methoxy-2-(3-methoxyphenyl)quinoline

6-Methoxy-2-(3-methoxyphenyl)-1H-quinoline-4-one[44] (5.63 g, 20 mmol) was added to POCl$_3$ (11.6 g, 7 mL, 75 mmol) in a round flask at 0° C. with stirring. The homogenous suspension in the flask was then immersed into pre-heated at 80° C. oil bath and continuously heated until it solidified (about 15 min). The reaction mixture was cooled to room temperature and added to the mixture of ice (150 g), saturated NaHCO$_3$ aqueous solution (100 mL) and CH$_2$Cl$_2$ (100 mL). The organic layer was separated and the water layer was extracted with CH$_2$Cl$_2$ (2×10 mL). The combined extracts were dried over Na$_2$SO$_4$, filtered and concentrated in vacuo to dryness. The residue was crystallized from CHCl$_3$/hexane to give 6-methoxy-2-(3-methoxyphenyl)-4-chloro-quinoline, 5.94 g (99.0%), which was pure enough for using in next step. The analytic sample was prepared by recrystallization (CHCl$_3$/hexane); mp 106-107° C.; $^1$H NMR (CDCl$_3$) δ3.93 and 3.99 (each: 3H, s, OCH$_3$), 7.00 (1H, dd, J=2.9, 8.1 Hz, ArH), 7.40-7.45 (3H, m, ArH), 7.64 (1H, d, J=8.1 Hz, ArH), 7.71 (1H, t, J=1.5 Hz, ArH), 7.92 (1H, s, ArH), 8.07 (1H, d, J=8.8 Hz, ArH). Anal. Calcd. for (C$_{17}$H$_{14}$Cl$_2$NO$_2$): C, 68.12; H, 4.71; N, 4.67. Found: C, 68.22; H, 4.34; N, 4.44.

2) Preparation of 4-amino-6-methoxy-2-(3-methoxyphenyl)quinoline

A mixture of 6-methoxy-2-(3-methoxyphenyl)-4-chloro-quinoline (5.90 g, 19.68 mmol) and phenol (20 g) was heated with stirring at 180° C. and ammonia was passed through the reaction mixture during 11 h. Phenol was then removed by steam distillation. The mixture was filtered and the filtrate was basified to pH 8 by adding 8% Na$_2$CO$_3$ aqueous solution. The solid formed was collected by filtration and dried to give the desired 4-amino-6-methoxy-2-(3-methoxyphenyl)quino- line, 5.313 g (96.3%); mp 148-149° C.; $^1$H NMR (DMSO-d$_6$) δ 3.85, 3.90 (each: 3H, s, OCH$_3$), 6.67 (2H, s, exchangeable, NH$_2$), 7.00 (1H, dd, J=2.9 and 8.1 Hz, ArH), 7.10 (1H, s, ArH), 7.28 (1H, dd, J=2.9 and 8.8 Hz, ArH), 7.40 (1H, t, J=8.1 Hz, ArH), 7.53 (1H, d, J=2.9 Hz, ArH), 7.61 (1H, 1H, d, J=8.1 Hz, ArH), 7.64 (1H, t, J=2.2 Hz, ArH), 7.77 (1H, d, J=8.8 Hz, ArH). Anal. Calcd. for (C$_{17}$H$_{16}$N$_2$O$_2$): C, 72.84; H, 5.75; N, 9.99. Found: C, 72.82; H, 5.51; N, 10.12.

3) Preparation of 1-{4-[bis(2-chloroethyl)amino] phenyl-3-[6-methoxy-2-(4-methoxyphenyl)-quinolin-4-yl]urea To a solution of N,N-bis(2-chloroethyl)benzene-1,4-di- amine hydrochloride (18, 0.918 g, 3.0 mmol) in dry CHCl$_3$ (35 mL) containing Et$_3$N (0.6 mL) was added dropwise a solution of triphosgene (356 mg, 1.2 mmol.) in an ice bath with vigorous stirring for 30 min. The reaction mixture was evaporated and the residue diluted with THF (20 mL), filtered through a pad of Celite, washed with THF (5 mL). This intermediate was dissolved in anhydrous DMF (1 mL) and then added dropwise to a solution of 4-amino-6-methoxy-2-(3-methoxyphenyl)quinoline (280 mg, 1.0 mmol) in dry DMF (1 mL). The reaction mixture was stirred at 50° C. for 9 h and the solvent was removed by vacuum distillation. The residue was chromatographed on a silica gel column (2×24 cm) using CHCl$_3$/MeOH/(100:1 v/v) as eluent. The fractions containing the desired product were combined, evaporated and the solid residue was recrystallized from EtOH to give 1-{4-[bis(2-chloroethyl)amino]phenyl-3-[6-methoxy-2-(4-methoxyphenyl)quinolin-4-yl]urea (BO-1049); 400 mg (74.2%); mp 112-113° C.; $^1$H NMR (DMSO-d$_6$) δ 3.72 (8H, m, 4×CH$_2$), 3.87 (3H, s, OMe), 4.01 (3H, s, OMe), 6.72 (2H, d, J=8.8 Hz, ArH), 7.07 (1H, dd, J=2.2 and 8.1 Hz, ArH), 7.41 (2H, d, J=8.8 Hz, 2×ArH), 7.47 (2H, m, 2×ArH), 7.65 (3H, m, ArH), 7.99 (2H, d, J=10.3 Hz, 2×ArH), 8.80 (1H, d, J=8.8 Hz, ArH), 9.25 (2H, brs, exchangeable, 2×NH). Anal. Calcd. for (C$_{28}$H$_{28}$Cl$_2$N$_4$O$_3$): C, 62.61; H, 5.23; N, 10.39. Found: C, 62.34; H, 4.99; N, 10.59.

Compound BO-1233

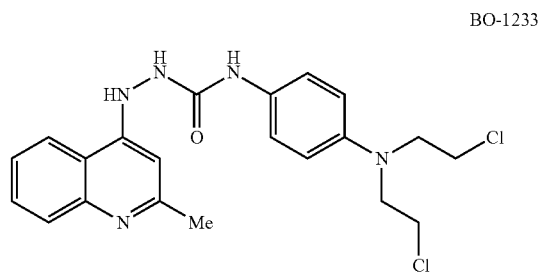

BO-1233

1) Preparation of 4-chloro-2-methylquinoline

The commercially available 4-hydroxy-2-methylquinoline (6.522 g, 41 mmol) was added portionwise to POCl$_3$ (35 mL) in a round flask at 0° C. with stirring. The homogenous suspension was then immersed into a pre-heated at 80° C. oil bath and continuously refluxed for 4 h. The reaction mixture was cooled to room temperature and the excess POCl$_3$ was distilled out under reduces pressure. The residue was treated carefully with ice (150 g) and then with saturated NaHCO$_3$ aqueous solution (200 mL). The mixture was extracted with CH$_2$Cl$_2$ (100×3 mL), dried over Na$_2$SO$_4$, and evaporated in vacuo to dryness to give known 4-chloro-2-methylquinoline,[52] 6.10 g (84.14%) as oil, which was pure enough for using in next step. $^1$H NMR (DMSO) δ 2.61 (3H, s, Me), 7.66 (1H, s, ArH), 7.67-7.71 (1H, m, ArH), 7.82-7.85 (1H, s, ArH), 8.01 (1H, d, J=6.7 Hz, ArH), 8.12-8.14 (1H, s, ArH). Anal. Calcd. for ($C_{10}H_8ClN$): C, 67.62; H, 4.54; N, 7.89. Found: C, 67.62; H, 4.54; N, 7.89.

2) Preparation of 4-hydrazino-2-methylquinoline

A solution of 4-chloro-2-methylquinoline (5.01 g, 28.2 mmol) and 80% hydrazine hydrate (8 ml) solution was refluxed in ethanol (30 mL) for 8 h. The resulting solution was cooled to room temperature and the solid formed was collected by filtration, washed with ethanol, and dried to yield known 4-hydrazino-2-methylquinoline,[53,54] 4.712 g (79.70%); mp 195-197° C.; $^1$H NMR (DMSO-$d_6$) δ 2.64 (3H, s, Me), 5.15 (2H, brs, exchangeable, $NH_2$), 6.99 (1H, s, ArH), 7.58 (1H, t, J=7.6 Hz, ArH), 7.86 (1H, t, J=7.6 Hz, ArH), 7.85 (1H, d, J=8.4 Hz, ArH), 8.42 (1H, d, J=8.2 Hz, ArH), 10.64 (1H, s, exchangeable, NH), Anal. Calcd. for ($C_{10}H_{12}N_3$·HCl): C, 57.28; H, 5.77; N, 20.04. Found: C, 57.28; H, 5.77; N, 20.04.

3) Preparation of N-{4-[bis(2-chloroethyl)amino] phenyl}-2-(2-methyl-4-quinolinyl)-hydrazinecarboxamide To a suspension of N,N-bis(2-chloroethyl)benzene-1,4-diamine hydrochloride (18, 2.524 g, 8.25 mmol) in dry $CHCl_3$ (20 mL), $Et_3N$ (2.5 mL) was added dropwise at −5-0° C. The resulting solution was added dropwise to a solution of triphosgene (0.673 g, 3.21 mmol) in dry $CHCl_3$ (15 mL) at −5-0° C. The reaction mixture was stirred at room temperature for 30 min. The resulting solution was evaporated under reduced pressure to dryness to give crude isocyanate (19) as liquid. This solution was added dropwise into a suspension of 4-hydrazino-2-methylquinoline (1.053 g, 5 mmol) in dry DMF (40 mL) containing $Et_3N$ (4 mL) at 0° C. The reacting mixture was stirred at room temperature for 1.5 h. The resulting solution was evaporated under reduced pressure to dryness. The solid residue was triturated with a mixture of THF/ether (2:1 v/v) and the solid was collected by filtration, washed with little amount of cold chloroform and methanol, and dried to give N-{4-[bis(2-chloroethyl)amino]phenyl}-2-(2-methyl-4-quinolinyl)hydrazinecarboxamide (BO-1233), 2.05 g (94.47%); mp 235-236° C.; $^1$H NMR (DMSO-$d_6$) δ 2.71 (3H, s, Me), 3.68-3.71 (8H, m, 4×$CH_2$), 6.70 (2H, d, J=9.0 Hz, ArH), 6.89 (1H, s, ArH), 7.31 (2H, d, J=9.0 Hz, ArH), 7.72 (1H, t, J=7.7 Hz, ArH), 7.97 (1H, t, J=7.1 Hz, ArH), 8.03 (1H, d, J=8.5 Hz, ArH), 8.49 (1H, d, J=8.5 Hz, ArH), 9.04 and 9.12 (each 1H, s, exchangeable, 2NH), 10.84 (1H, brs, exchangeable, NH). Anal. Calcd. for ($C_{21}H_{23}Cl_2N_5O$): C, 58.34; H, 5.36; N, 16.20. Found: C, 58.50; H, 5.37; N, 16.40.

Compound BO-1228

BO-1228

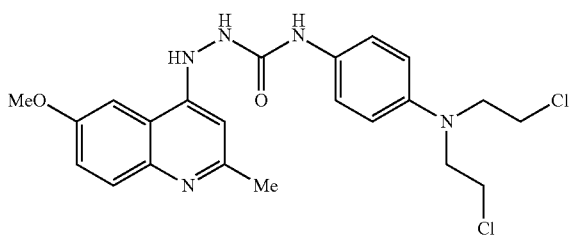

To a suspension of N,N-bis(2-chloroethyl)benzene-1,4-diamine hydrochloride (18, 0.826 g, 2.7 mmol) in dry $CHCl_3$ (10 mL), $Et_3N$ (1.5 mL) was added dropwise at −5-0° C. The resulting solution was added dropwise to a solution of triphosgene (0.296 g, 1 mmol) in dry $CHCl_3$ (10 mL) at −5-0° C. The reaction mixture was stirred at room temperature for 30 min. The resulting solution was evaporated under reduced pressure to dryness to give crude isocyanate (19) as liquid. This solution was added dropwise into a suspension of known 4-hydrazino-6-methoxy-2-methylquinoline (0.36 g, 1.5 mmol)[55] and $Et_3N$ (2 mL) in dry DMF (15 mL at 0° C. The reacting mixture was stirred at room temperature for 1.5 h. The resulting solution was evaporated under reduced pressure to dryness. The solid residue was triturated with a mixture of THF/ether (2:1 v/v) and the solid was collected by filtration, washed with little amount of cold chloroform and methanol, and dried to give N-{4-[bis(2-chloroethyl)amino]phenyl}-2-(6-methoxy-2-methyl-4-quinolinyl)hydrazinecarboxamide (BO-1228), 0.413 g (60%): mp 224-225° C.; $^1$H NMR (DMSO-$d_6$) δ 2.68 (3H, s, Me), 3.68-3.70 (8H, m, 4×$CH_2$), 3.94 (3H, s, OMe), 6.70 (2H, d, J=9.0 Hz, ArH), 6.84 (1H, s, ArH), 7.31 (2H, d, J=9.0 Hz, ArH), 7.61 (1H, dd, J=2.2 and 9.2 Hz, ArH), 7.91 (1H, d, J=2.2 Hz, ArH), 7.96 (1H, d, J=9.2 Hz, ArH), 9.01 and 9.11 (each 1H, s, exchangeable, 2×NH), 10.65 (1H, brs, exchangeable, NH). Anal. Calcld. for ($C_{22}H_{25}Cl_2N_5O_2$): C, 57.14; H, 5.45; N, 15.15. Found: C, 57.40; H, 5.18; N, 15.52.

Compound BO-1034

BO-1034

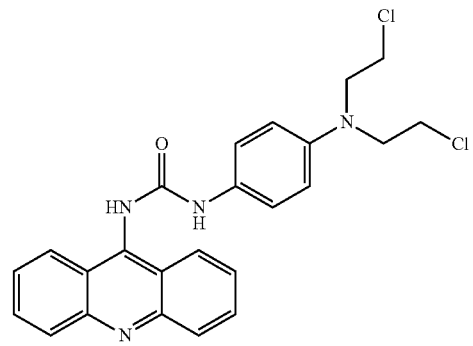

To a solution of N,N-bis(2-chloroethyl)benzene-1,4-diamine hydrochloride (18, 0.306 g, 1.0 mmol) in dry $CHCl_3$ (35 mL) containing $Et_3N$ (0.2 mL) was added dropwise a solution of triphosgene (115 mg, 0.4 mmol.) in an ice bath with vigorous stirring for 30 min. The reaction mixture was evaporated and the residue diluted with THF (20 mL), filtered through a pad of Celite, washed with THF (5 mL). The combined filtrate and washings (containing carbamoyl chloride 38) were then added dropwise into a solution of commercially available 9-aminoacridine hydrochloride (248 mg, 1.0 mmol) in dry DMF (10 mL) containing $Et_3N$ (0.5 mL) at room temperature. After being stirred for 16 h, the solvent was evaporated under reduced pressure and the residue was dissolved in a mixture of $CHCl_3$/MeOH containing silica gel (5 g) and evaporated in vacuo to dryness. The residue was put on the top of a silica gel column (2×20 cm) using $CHCl_3$/MeOH (50/1v/v) as eluent. The fractions containing the main product were combined and evaporated in vacuo to dryness and residue was recrystallized from acetone to give 1-acridin-9-yl-3-{4-[bis(2-chloroethyl)amino]phenyl}urea (BO-1034); 273 mg (60%); mp 184-186° C.; $^1$HNMR (DMSO-$d_6$) δ 3.71 (8H, s, 4×$CH_2$), 6.73 (2H, d, J=9.1 Hz, 2×ArH), 7.10-7.13 (2H, m, 2×ArH), 7.28-7.53 (3H, m, 3×ArH), 7.58-7.60 (2H, m, 2×ArH), 7.84 (1H, brs, exchangeable, NH), 8.15 (2H, d, J=9.1 Hz, 2×ArH), 8.22 (1H, m, ArH), 9.37 (1H, brs, exchangeable, NH). Anal. Calcld. for ($C_{24}H_{22}Cl_2N_4O$); C, 63.58; H, 4.89; N, 12.36. Found: C, 63.35; H, 5.05; N, 12.09.

Compound BO-1547

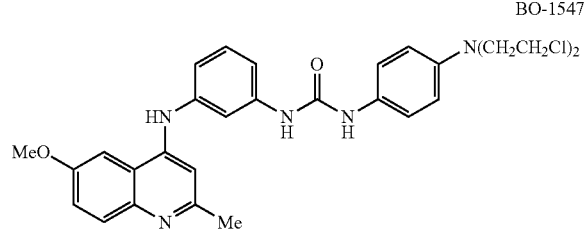

To a suspension of N,N-bis(2-chloroethyl)benzene-1,4-diamine hydrochloride 18 (1.22 g, 4 mmol) in dry chloroform (50 mL) was added triethylamine (0.72 mL) at room temperature. The clear solution obtained was then cooled to −10° C. and a solution of triphosgene (0.712 g, 2.4 mmole) in dry chloroform (10 mL) was added dropwise into a reaction mixture at 0° C. After being stirred for 30 min, the reaction mixture was evaporated to dryness under reduced pressure. The solid residue was triturated with dry THF (100 ml), filtered, and washed with small amount of THF. The combined filtrate and washings was evaporated to dryness to give the crude isocyanate 19, which was then dissolved in dry DMF (5 mL) and added dropwise to a solution of N1-(6-methoxy-2-methylquinolin-4-yl)benzene-1,3-diamine (0.56 g, 2 mmol) in dry DMF (10 mL) containing Et$_3$N (1 mL). After being stirred for 5 h at room temperature, the solid separated was filtered and washed with dry DMF. The filtrate was evaporated to dryness in vacuo. The residue was purified by column chromatography using CHCl$_3$/MeOH (100:3 v/v) as an eluent. The fractions containing the main product were combined and evaporated to dryness and the residue was recrystallized from CHCl$_3$ to give BO-1547 (0.87 g, 81%); mp 225-227° C.; $^1$H NMR (DMSO-d$_6$) δ 2.58 (3H, s, Me), 3.68-3.70 (8H, m, CH$_2$), 3.97 (3H, s, OMe), 6.73-6.69 (3H, m, Ar—H), 7.03 (1H, d, J=7.6 Hz, Ar—H), 7.28 (2H, d, J=9.0 Hz, Ar—H), 7.35 (1H, d, J=7.7 Hz, Ar—H), 7.44 (1H, t, J=8.0 Hz, Ar—H), 7.64-7.62 (1H, m, Ar—H), 7.71 (1H, s, Ar—H), 7.93 (1H, d, J=9.1 Hz, Ar—H), 8.09 (1H, s, Ar—H), 8.84 (1H, s, NH, Exchangeable), 9.31 (1H, s, NH, Exchangeable), 10.49 (1H, s, NH, Exchangeable); ESI-HRMS calcd for C$_{28}$H$_{29}$Cl$_2$N$_5$O$_2$ m/z 538.4682 (M+H). found 538.2451 (M+H).

Compound BO-1037

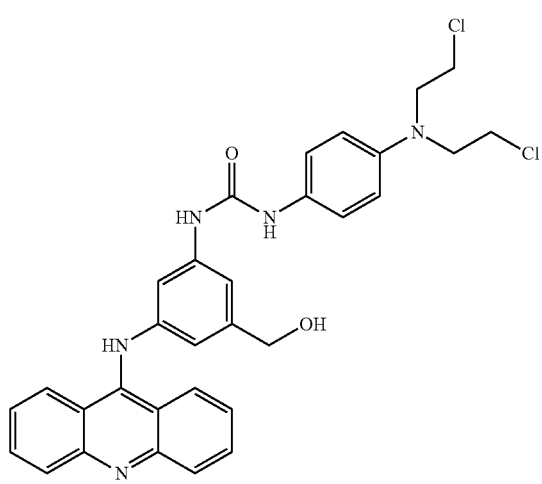

To a solution of N,N-bis(2-chloroethyl)benzene-1,4-diamine hydrochloride (18, 0.306 g, 1.0 mmol) in dry CHCl$_3$ (35 mL) containing Et$_3$N (0.2 mL) was added dropwise a solution of triphosgene (115 mg, 0.4 mmol.) in an ice bath with vigorous stirring for 30 min. The reaction mixture was evaporated and the residue diluted with THF (20 mL), filtered through a pad of Celite, washed with THF (5 mL). The filtrate and washings were combined and was added dropwise into a solution of 3-(acridin-9-yl)amino-5-hydroxymethylaniline (6, AHMA)$^{18}$ (0.351 g, 1.0 mmol) in dry DMF (10 mL) containing Et$_3$N (0.5 mL) at 0° C. After being stirred for 18 h, the reaction mixture was evaporated in vacuo to dryness and the residue was dissolved in a mixture of CHCl$_3$/MeOH, mixed with silica gel (5 gm) and evaporated in vacuo to dryness. The residue was put on the top of a silica gel column (2×20 cm) and chromatographed using CHCl$_3$/MeOH (100:5 v/v) as eluent. The fractions containing the main product were combined and evaporated in vacuo to dryness and residue was recrystallized from CHCl$_3$/MeOH to give 1-[3-(acridin-9-ylamino)-5-hydroxymethylphenyl]-3-{4-[bis(2-chloroethyl)amino]phenyl}urea (BO-1037), 205 mg (35%); mp 173-175° C.; $^1$H NMR (DMSO-d$_6$) δ 3.67 (8H, m, 4×CH$_2$), 4.41 (2H, d, J=6.0 Hz, CH$_2$), 5.14 (1H, t, J=6.0 Hz, exchangeable, OH), 6.37 (1H, s, ArH), 6.68 (2H, d, J=9.1 Hz, 2×ArH,), 6.81 (1H, s, ArH), 7.01 (1H, s, ArH), 7.05-7.19 (1H, m, ArH), 7.24 (2H, d, J=9.1 Hz, 2×ArH), 7.55 (4H, m, 4×ArH) 8.05 (2H, m, 2×ArH), 8.25 (1H, m, ArH) 8.46 (1H, m, ArH), 10.48 (1H, brs, exchangeable, NH). Anal. Calcd. for (C$_{31}$H$_{29}$Cl$_2$N$_5$O$_2$): C, 63.81; H, 5.18; N, 12.00. Found: C, 64.07; H, 5.26; N, 11.87.

Compound BO-1050

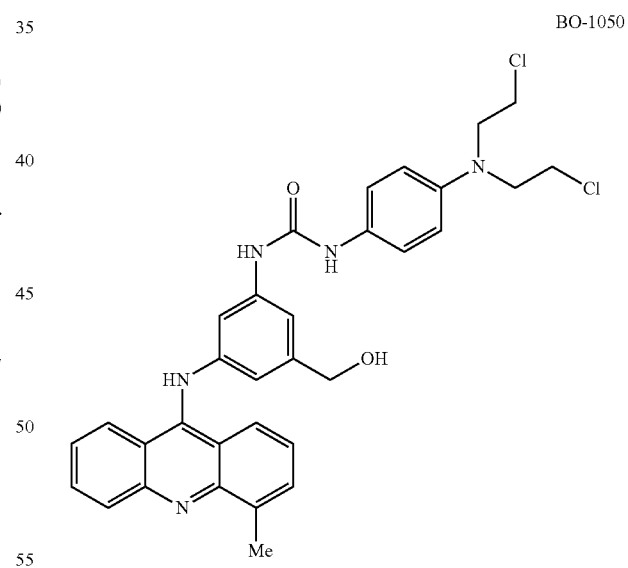

To a solution of N,N-bis(2-chloroethyl)benzene-1,4-diamine hydrochloride (18, 0.306 g, 1.0 mmol) in dry CHCl$_3$ (35 mL) containing Et$_3$N (0.2 mL) was added dropwise a solution of triphosgene (115 mg, 0.4 mmol.) in an ice bath with vigorous stirring for 30 min. The reaction mixture was evaporated and the residue diluted with THF (20 mL), filtered through a pad of Celite, washed with THF (5 mL). The filtrate and washings were combined and was then added dropwise into a solution of 3-amino-5-(4-methylacridin-9-ylamino)phenyl]-methanol$^{18}$ (0.329 mg, 1.0 mmol) in dry DMF (20 mL) containing Et$_3$N (0.5 mL) at 0° C. and stirred at room temperature for 16 h. The solvent was removed by distillation under reduced pressure to dryness and the residue was dissolved in CHCl$_3$/MeOH and mixed with silica gel (5 g) and then evaporated in vacuo to dryness. The residue was put on the top of a silica gel column (2×20 cm) and chromatographed using CHCl$_3$/MeOH (100:2 v/v) as eluent. The fractions containing the main product were combined and concentrated in vacuo and the residue was recrystallized from CHCl$_3$/MeOH to give 1-{4-[bis(2-chloroethyl)amino]phenyl}-3-[3-hydroxymethyl-5-(4-methylacridin-9-ylamino)phenyl]urea (BO-1050), 179 mg (30%); mp 251-252° C.; $^1$H NMR (DMSO-d$_6$) δ 3.64-3.71 (8H, m, 4×CH$_2$), 4.00 (3H, s, Me), 4.47 (2H, d, J=5.1 Hz, CH$_2$) 5.11 (1H, t, J=5.1 Hz, exchangeable, OH), 6.35 (1H, s, ArH), 6.68 (2H, d, J=8.8 Hz, 2×ArH) 6.75 (1H, s, ArH), 6.88-7.18 (4H, m, 4×ArH), 7.24 (2H, d, J=8.8 Hz, 2×ArH) 7.52 (2H, s, 2×ArH), 7.83 (2H, s, 2×ArH), 8.25 (1H, s, ArH) 8.40 (1H, s, ArH), 10.24 (1H, s, exchangeable, NH). Anal. Calcld. for (C$_{32}$H$_{31}$Cl$_2$N$_5$O$_2$.3H$_2$O): C, 59.81; H, 5.80; N, 10.89. Found: C, 59.74; H, 5.79; N, 9.67.

Compound BO-1051

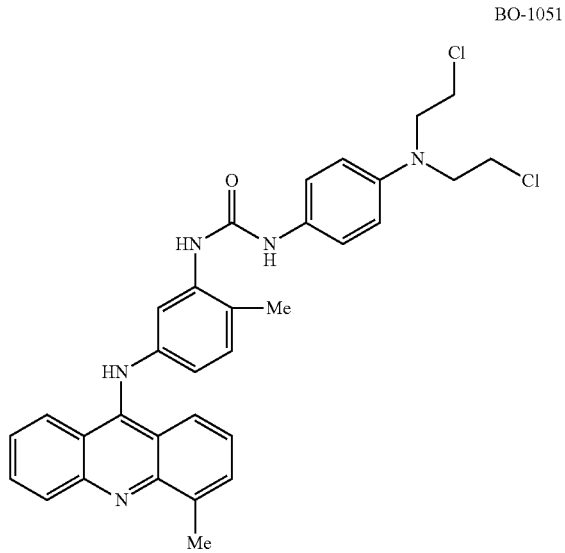

BO-1051

To a solution of N,N-bis(2-chloroethyl)benzene-1,4-diamine hydrochloride (18, 1.84 g, 6.0 mmol) in dry CHCl$_3$ (100 mL) containing Et$_3$N (1.1 mL) was added dropwise a solution of triphosgene (712 mg, 2.4 mmol.) in an ice bath with vigorous stirring for 30 min. The reaction mixture was evaporated and the residue diluted with THF (100 mL), filtered through a pad of Celite, washed with THF (25 mL). The filtrate containing crude mustard isocyanate 19 was added dropwise into the solution of 4-methyl-N'-1'-(4-methylacridin-9-yl)benzene-1,3-diamine$^{33}$ (1.065 g, 3.4 mmol) in dry DMF (50 mL) containing pyridine (2 mL) at −10° C. The reaction mix was allowed to stir at room temperature for 19 h. The solvent removed under reduce pressure and the solid residue was recrystallized from CHCl$_3$:MeOH (1:10) to give 1-{4-[bis(2-chloroethyl)-amino]phenyl}-3-[3-hydroxymethyl-5-(4-methylacridin-9-yl-amino)phenyl]urea (BO-1051), 1.63 g (83.8%); mp 267-270° C.; $^1$H NMR (DMSO-d$_6$) δ 2.34 (3H, s, Me), 2.78 (3H, s, Me), 3.65-3.70 (8H, m, 4×CH$_2$), 6.68 (2H, d, J=9.4 Hz, 2×ArH), 6.87 (1H, m, ArH), 7.22-7.35 (3H, m, ArH), 7.35-7.43 (1H, m, ArH), 7.43-7.49 (1H, m, ArH), 7.86 (1H, d, m, ArH), 7.94-8.03 (1H, m, ArH), 8.13-8.26 (3H, m, 3×ArH), 8.28 (1H, brs, exchangeable, NH), 8.34 (1H, m, ArH), 9.35 (1H, brs, exchangeable, NH), 11.51 (1H, brs, exchangeable, NH). Anal. Calcld. for (C$_{32}$H$_{31}$Cl$_2$N$_5$O.2H$_2$O): C, 63.15; H, 3.13; N, 11.50. Found: C, 63.38; H, 3.52; N, 10.97.

Compound BO-1079

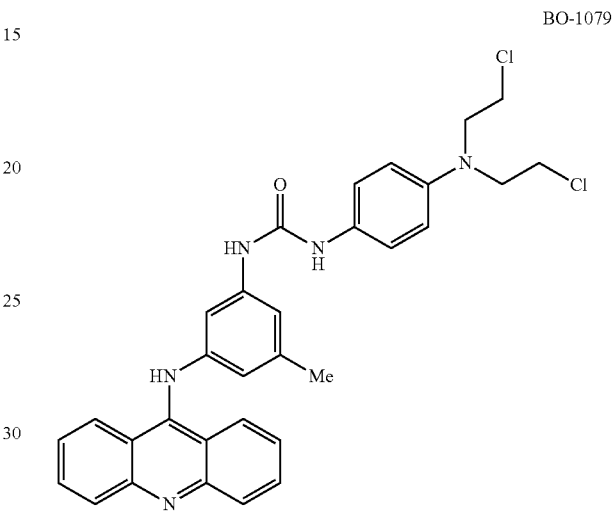

BO-1079

To a solution of N,N-bis(2-chloroethyl)benzene-1,4-diamine hydrochloride (18, 0.918 g, 3.0 mmol) in dry CHCl$_3$ (35 mL) containing Et$_3$N (0.6 mL) was added dropwise a solution of triphosgene (356 mg, 1.2 mmol.) in an ice bath with vigorous stirring for 30 min. The reaction mixture was evaporated and the residue diluted with THF (20 mL), filtered through a pad of Celite, washed with THF (5 mL). The filtrate containing crude N-mustard isocyanate 19 was evaporated in vacuo to dryness and the residue was dissolved in dry DMF (5 mL) and then added dropwise into the solution of N-acridin-9-yl-5-methylbenzene-1,3-diamine (0.517 g, 1.7 mmol) in dry DMF (25 mL) containing pyridine (2 mL) at −10° C. The reaction mixture was allowed to cool down to room temperature and continuously stirred for 24 h and then evaporated in vacuo to dryness. The residue was dissolved in a mixture of CHCl$_3$/MeOH containing silica gel (10 g) and evaporated under reduced pressure to dryness. The residue was put on the top of a silica gel column (4×30 cm) and chromatographed by using CHCl$_3$/MeOH (100:3 v/v) as eluent. The fractions containing the main product were combined and evaporated in vacuo to dryness to give 1-[3-(acridin-9-ylamino)-5-methylphenyl]-3-{4-[bis(2-chloroethyl)amino]phenyl}urea (BO-1079), 0.375 g (39%); mp 280-285° C.; 1H NMR (DMSO-d6) δ 2.26 (3H, s, Me), 3.68 (8H, s, 4×CH$_2$), 6.68 (2H, d, J=9.0 Hz, ArH) 6.75-6.89 (1H, m, ArH), 7.19-7.32 (3H, m, ArH), 7.40-7.62 (3H, m, ArH), 7.93-8.14 (4H, m, ArH), 8.29 (2H, d, J=9.0 Hz, ArH), 8.94 (1H, brs, exchangeable, NH), 9.37 (1H, brs, exchangeable, NH), 11.51 (1H, brs, exchangeable, NH). Anal. Calcld. for (C$_{31}$H$_{29}$Cl$_2$N$_5$.0.3; H$_2$O): C, 60.88; H, 6.11; N, 11.45. Found: C, 61.08; H, 6.18; N, 11.32.

Compound BO-1053

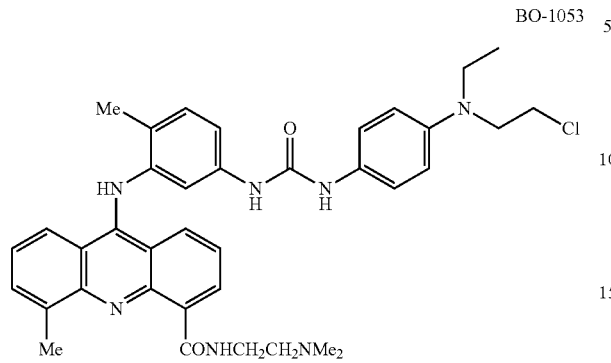

To a solution of N,N-bis(2-chloroethyl)benzene-1,4-diamine hydrochloride (18, 0.918 g, 3.0 mmol) in dry CHCl$_3$ (35 mL) containing Et$_3$N (0.6 mL) was added dropwise a solution of triphosgene (356 mg, 1.2 mmol.) in an ice bath with vigorous stirring for 30 min. The reaction mixture was evaporated and the residue diluted with THF (20 mL), filtered through a pad of Celite, washed with THF (5 mL). The filtrate containing crude N-mustard isocyanate 19 was evaporated in vacuo to dryness and the residue was dissolved in dry DMF (5 mL) and then added dropwise into the solution of 9-(5-amino-2-methyl-phenylamino)-5-methylacridine-4-carboxylic acid (2-dimethylaminoethyl)amide (0.732 g, 1.7 mmol)[33] in dry DMF (25 mL) containing pyridine (2 mL) at −10° C. and then stirred at room temperature for 24 h. The solvent removed under reduced pressure to dryness and the residue was dissolved in a mixture of CHCl$_3$/MeOH containing silica gel (10 gm) and evaporated in vacuo to dryness. The residue was put on the top of a silica gel column (4×30 cm) and chromatographed using CHCl$_3$/MeOH (100:5 v/v) as eluent. The fractions containing the main product were combined and evaporated in vacuo to dryness. The residue was recrystallized from EtOH/hexane to give 9-[5-(3-{4-[bis(2-chloroethyl)amino]phenyl}ureido)-2-methyl-phenylamino]-5-methyl-acridine-4-carboxylic acid (2-dimethylaminoethyl)amide (BO-1053); 0.385 g (32%); mp 286-289° C.; $^1$H NMR (DMSO-d$_6$) δ 2.19 (3H, s, Me), 2.67 (6H, m, NMe$_2$), 2.85 (3H, s, Me), 3.14 (2H, brs, CH$_2$), 3.63-3.69 (8H, m, 4×CH$_2$), 3.85 (2H, brs, CH$_2$), 6.41 (1H, m, ArH,), 6.65 (2H, d, J=9.0 Hz, ArH), 6.97 (1H, m, ArH), 7.24 (2H, d, J=9.0 Hz, ArH), 7.36-7.44 (1H, m, ArH), 7.51 (1H, m, ArH), 7.74 (2H, m, ArH), 7.93 (1H, m, ArH), 8.09 (1H, m, ArH), 8.41 (1H, m, ArH), 8.67 (1H, m, ArH), 9.04 (1H, brs, exchangeable, NH), 9.45 (1H, brs, exchangeable, NH), 12.18 (1H, brs, exchangeable, NH). Anal. Calcld. for (C$_{37}$H$_{41}$Cl$_2$N$_7$O$_2$.6H$_2$O): C, 54.91; H, 5.20; N, 12.34. Found: C, 55.08; H, 5.32; N, 12.44.

Compound BO-1062

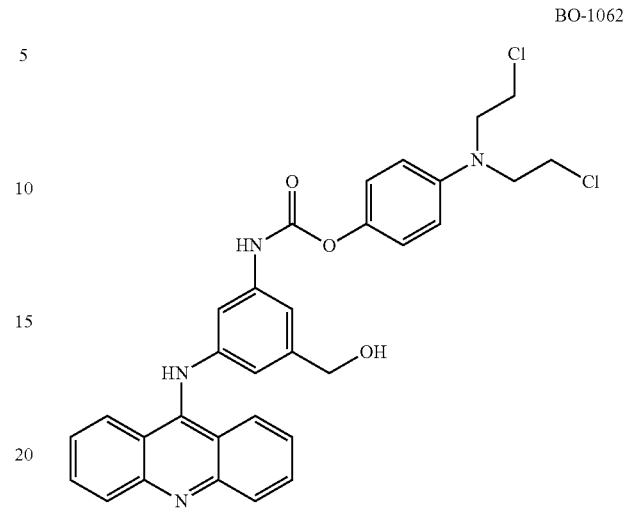

The known 4-[N,N-bis(2-chloroethyl)aminophenyl-4-nitrophenyl carbonate[39-41] (30, 1.12 g, 2.7 mmol) was added into a solution of 3-(acridin-9-ylamino)-5-hydroxymethylaniline (AHMA)[18] (1.130 g, 2.73 mmol) in dry DMF (20 mL) containing pyridine (5 mL) at 0° C. After being stirred at room temperature for 21 h, the reaction mixture was evaporated under reduced pressure to dryness. The solid residue was triturated with acetone (15 mL) and filtered. The filtered cake was washed with acetone (10 mL) and then recrystallized from CHCl$_3$/MeOH (1:10) to give the desired [3-(acridin-9-ylamino)-5-hydroxymethylphenyl]carbamic acid 4-[bis(2-chloroethyl)amino]phenyl ester (BO-1062), 1.169 g (79%); mp 241-242° C.; $^1$H NMR (DMSO-d$_6$) δ 3.72 (8H, s, 4×CH$_2$), 4.46 (2H, s, CH$_2$), 5.36 (1H, brs, exchangeable, OH), 6.74 (2H, d, J=9.0 Hz, 2×ArH), 6.93-723 (3H, m, 3×ArH), 7.40-7.73 (4H, m, 4×ArH), 7.93-8.05 (2H, m, ArH), 8.06-8.22 (2H, m, ArH), 8.23-8.46 (2H, m, ArH), 10.38 (1H, s, exchangeable, NH), 11.53 (1H, brs. exchangeable, NH). Anal. Calcld. for (C$_{31}$H$_{28}$Cl$_2$N$_4$O$_3$.3H$_2$O): C, 59.24; H, 5.42; N, 8.91. Found: C, 58.96; H, 5.08; N, 8.89.

Compound BO-1063

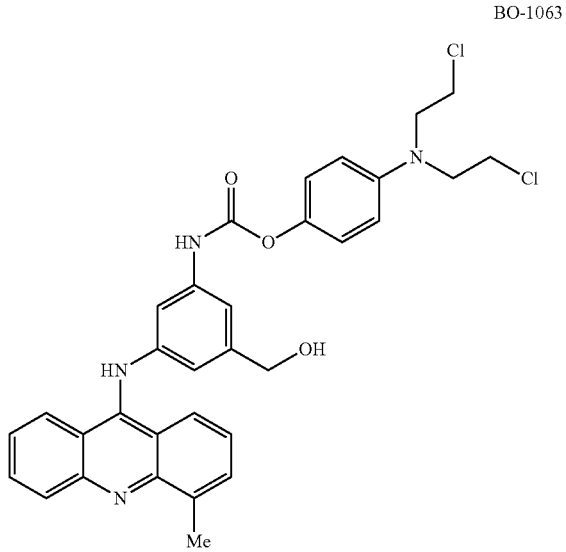

4-[N,N-bis(2-chloroethyl)aminophenyl-4-nitrophenyl carbonate (30)[39-41] (1.1967 g, 3.0 mmol) was added into a solution of 3-amino-5-(4-methylacridin-9-ylamino)phenyl] methanol[33] (0.987, 3.0 mmol) in dry DMF (20 mL) containing pyridine (5 mL) at 0° C. for 1 h and then stirred at room temperature for 21 h. The reaction mixture was evaporated in vacuo to dryness and the solid was triturated with acetone (15 mL) and then filtered. The filtered cake was washed with acetone (5 mL) and the recrystallized from CHCl$_3$/MeOH (1:10) to give the resired [3-hydroxymethyl-5-(4-methylacridin-9-ylamino)phenyl]carbamic acid 4-[bis(2-chloroethyl)-amino]phenyl ester (BO-1063), 1.053 g (61%); mp 229-231° C.; $^1$H NMR (DMSO-d$_6$) δ 2.81 (3H, s, Me), 3.72 (8H, s, 4×CH$_2$), 4.57 (2H, s, CH$_2$), 5.35 (1H, brs, exchangeable, OH), 6.74 (2H, d, J=9.0 Hz, 2×ArH), 6.98 (1H, s, ArH), 7.03 (2H, d, J=9.0 Hz, 2×ArH), 7.32-7.69 (4H, m, 4×ArH), 7.80-7.93 (1H, m, ArH), 7.96-8.11 (1H, m, ArH), 8.17-8.44 (2H, m, 2×ArH), 8.48-8.72 (1H, m, ArH), 10.37 (1H, brs, exchangeable, NH), 11.77 (1H, brs, exchangeable, NH). Anal. Calcld. for (C$_{32}$H$_{30}$Cl$_2$N$_4$O$_3$.3H$_2$O): C, 59.72; H, 5.64; N, 8.71. Found: C, 59.57; H, 5.34; N, 8.61.

Compound BO-1064

BO-1064

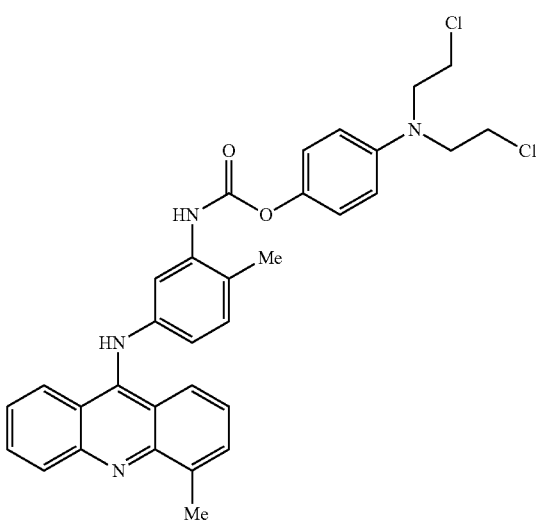

4-[N,N-bis(2-chloroethyl)aminophenyl-4-nitrophenyl carbonate (30) (1.198 g, 3.0 mmol) was added portionwise into a solution of 4-methyl-N'1'-(4-methylacridin-9-yl)benzene-1,3-diamine[33] (0.940 g, 2.73 mmol) in dry DMF (20 mL) containing pyridine (5 ml) at room temperature. After being stirred for 36 h, the solvent was evaporated under reduced pressure and the residue was dissolved in a mixture of CHCl$_3$/MeOH containing silica gel (5 gm) and evaporated in vacuo to dryness. The residue was put on the top of a silica gel column (4×20 cm) and chromatographed by using CHCl$_3$/MeOH (100/1 v/v) as eluent. The fractions containing the main product were combined and evaporated in vacuo to dryness and the residue was recrystallized from CHCl$_3$/MeOH to give [2-methyl-5-(4-methylacridin-9-ylamino)phenyl]-carbamic acid 4-[bis(2-chloroethyl)amino]phenyl ester (BO-1064); 0.905 g (52.5%); mp 154-156° C.; $^1$H NMR (DMSO-d$_6$) δ 2.36 (1H, s, Me), 2.81 (1H, s, Me), 3.71 (8H, s, 4×CH$_2$), 6.72 (2H, d, J=9.0 Hz, ArH), 6.94-7.07 (2H, m, ArH), 7.09-7.18 (1H, m, ArH), 7.28-7.52 (3H, m, ArH), 7.56-7.70 (1H, m, ArH), 7.79-7.90 (1H, m, ArH), 7.92-8.04 (1H, m, ArH), 8.18-8.34 (2H, m, ArH), 8.52-8.65 (1H, m, ArH), 9.52 (1H, s, exchangeable, NH), 11.65 (1H, brs, exchangeable, NH). Anal. Calcld. for (C$_{32}$H$_{30}$Cl$_2$N$_4$O$_2$.4.5H$_2$O): C, 58.73; H, 6.00; N, 8.56. Found: C, 58.57; H, 5.84; N, 8.62.

Compound BO-1066

BO-1066

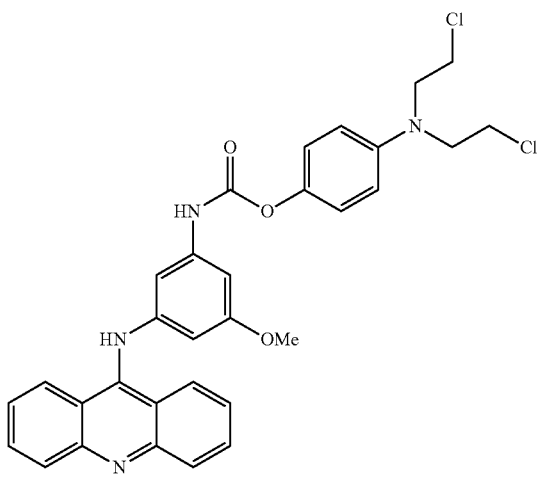

4-[N,N-bis(2-chloroethyl)aminophenyl-4-nitrophenyl carbonate (30) (1.198 g, 3.0 mmol) was added portionwise into a solution of N-acridin-9-yl-5-methoxybenzene-1,3-diamine[34] (0.945 g, 3.0 mmol) in dry DMF (20 mL) containing pyridine (5 mL) at room temperature. After being stirred for 56 h, the solvent was evaporated under reduced pressure and the residue was dissolved in a mixture of CHCl$_3$/MeOH containing silica gel (5 g) and evaporated in vacuo to dryness. The residue was put on the top of a silica gel column (4×20 cm) and chromatographed by using CHCl$_3$/MeOH (100/1 v/v) as eluent. The fractions containing the main product were combined and evaporated in vacuo to dryness and the residue recrystallize from CHCl$_3$/MeOH to give [3-(acridin-9-ylamino)-5-methoxyphenyl]carbamic acid 4-[bis(2-chloroethyl)amino]phenyl ester (BO-1066); 0.317 g (21%); mp 179-180° C.; $^1$H NMR (DMSO-d$_6$) δ 3.34 (3H, s, Me), 3.71 (8H, s, 4×CH$_2$), 6.08-6.16 (1H, m, ArH), 6.51-6.61 (1H, m, ArH), 6.74 (2H, d, J=9.0 Hz, ArH) 6.85-6.93 (1H, m, ArH), 7.02 (2H, d, J=9.0 Hz, ArH), 7.04-7.17 (H, m, ArH), 7.36-7.66 (4H, m, ArH), 7.77-8.14 (2H, m, ArH), 10.05 (1H, s, exchangeable, NH), 11.23 (1H, brs, exchangeable, NH). Anal. Calcld. for (C$_{31}$H$_{28}$Cl$_2$N$_4$O$_3$.0.5H$_2$O): C, 63.70; H, 5.00; N, 9.59. Found: C, 63.62; H, 5.03; N, 9.51.

Compound BO-1065

BO-1065

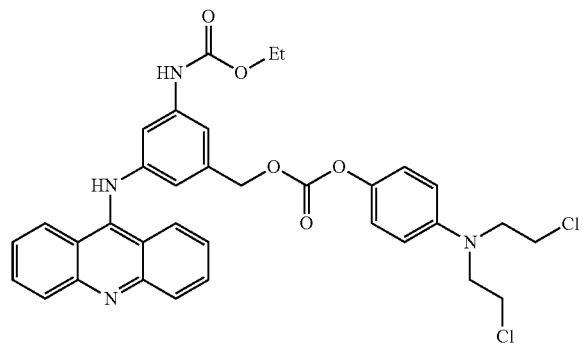

4-[N,N-bis(2-chloroethyl)aminophenyl-4-nitrophenyl carbonate[39-41] (30) (0.800 g, 2.0 mmol) was added portionwise into a solution of [3-(acridin-9-ylamino)-5-hydroxymethyl-phenyl]carbamic acid ethyl ester[56] (0.774 g, 2.0 mmol) in dry DMF (10 mL) containing pyridine (4 mL) at room temperature. After being stirred for 40 h, the solvent was evaporated under reduced pressure and the residue was dissolved in a mixture of $CHCl_3$/MeOH containing silica gel (5 g) and then evaporated in vacuo to dryness. The residue was put on the top of a silica gel column (4×20 cm) and chromatographed by using $CHCl_3$/MeOH (100/1 v/v) as eluent. The fractions containing the main product were combined and evaporated in vacuo to dryness and the residue recrystallized from $CHCl_3$/MeOH to give carbonic acid 3-(acridin-9-ylamino)-5-ethoxycarbonylaminobenzyl ester 4-[bis(2-chloroethyl)amino]phenyl ester (BO-1065); 0.719 g (55.7%); mp 131-133° C.; $^1$H NMR (DMSO-$d_6$) δ 1.22 (3H, t, J=9.0 Hz, Me), 3.71 (8H, s, 4×$CH_2$), 4.09 (2H, q, J=9.0 Hz, $CH_2$), 5.13 (1H, s, $CH_2$), 6.43-6.62 (1H, m, ArH) 6.73 (2H, d, J=9.0 Hz, ArH), 6.68-7.19 (5H, m, ArH), 7.21-7.19 (1H, m, ArH), 7.38-7.72 (4H, m, ArH), 7.75-8.39 (2H, m, ArH), 9.66 (1H, s, exchangeable, NH), 11.17 (1H, brs, exchangeable, NH). Anal. Calcld. for ($C_{34}H_{32}Cl_2N_4O_5$·0.5$H_2O$): C, 62.20; H, 5.07; N, 8.53. Found: C, 62.29; H, 5.07; N, 8.52.

Compound BO-1262

BO-1262

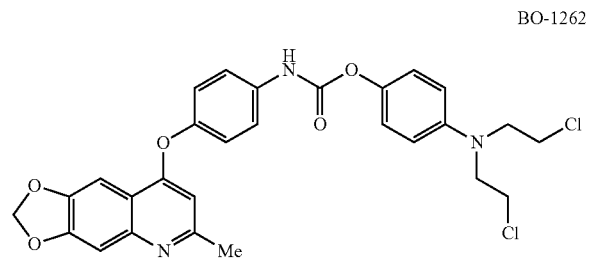

1) Preparation of 6-methyl-8-(4-nitrophenoxy)[1,3]dioxolo[4,5-g]quinoline

A mixture of known 8-chloro-6-methyl[1,3]dioxolo[4,5-g]quinoline (2.216 g, 10 mmol)[56] and 4-nitrophenol (2.08 g, 15 mmole) was heated at 140-150° C. for 2 h. The resulting solution was dissolved in chloroform and washed with 10% aq. solution of NaOH and brine. The organic layer was dried over anhydrous $Na_2SO_4$ and concentrated under reduce pressure. The resulting solid was collected by filtration, washed with ether and dried to 6-methyl-8-(4-nitrophenoxy)[1,3]dioxolo[4,5-g]quinoline, 2.94 g of (90.60%); mp 210-212° C.; $^1$H NMR (DMSO-$d_6$) δ 2.52 (3H, s, Me), 6.21 (2H, s, $CH_2$), 6.86 (1H, s, ArH), 7.30 (1H, s, ArH), 7.34-7.38 (3H, m, ArH), 8.29-8.33 (2H, m, ArH). Anal. Calcld. for ($C_{17}H_{12}N_2O_5$): C, 62.96; H, 3.73; N, 8.64. Found: C, 62.27; H, 3.84; N, 8.58.

2) Preparation of 4-[(6-methyl[1,3]dioxolo[4,5-g]quinolin-8-yl)oxy]phenylamine A mixture of 6-methyl-8-(4-nitrophenoxy)[1,3]dioxolo[4,5-g]quinoline (2.0 g, 6.18 mmol) in dioxane (100 mL) and 10% Pd/C (500 mg) was hydrogenated for 7 h at 35 psi. The reaction mixture was filtered through a pad of Celite and the filter cake was washed with dioxan. The combined filtrate and washings was evaporated in vacuo to dryness. The solid residue recrystallized from $CHCl_3$ to yield 4-[(6-methyl[1,3]dioxolo-[4,5-g]quinolin-8-yl)oxy]phenylamine, 1.680 g (92.43%); mp 251-253° C.; $^1$HNMR (DMSO-$d_6$) δ 2.43 (3H, s, Me), 5.56 (2H, brs, exchangeable, $NH_2$), 6.21 (2H, s, $CH_2$), 6.32 (1H, s, ArH), 6.66 (2H, d, J=8.6 Hz, ArH), 6.90 (2H, d, J=8.6 Hz, ArH), 7.28 (1H, s, ArH), 7.49 (1H, s, ArH). Anal. Calcld. for ($C_{17}H_{14}N_2O_3$): C, 69.38; H, 4.79; N, 9.25. Found: C, 69.57; H, 4.88; N, 9.32.

3) Preparation of N-{4-[bis(2-chloroethyl)amino]phenyl}-N'-{4-[(6-methyl[1,3]dioxolo[4,5-g]-quinolin-8-yl)oxy]phenyl}urea To a suspension of N,N-bis(2-chloroethyl)benzene-1,4-diamine hydrochloride (37, 1.101 g, 3.6 mmol) in dry $CHCl_3$ (10 mL), $Et_3N$ (1.5 mL) was added dropwise at −5-0° C. The resulting solution was added dropwise to a solution of triphosgene (0.415 g, 1.4 mmol) in dry $CHCl_3$ (10 mL) at −5-0° C. The reaction mixture was stirred at room temperature for 30 min. The resulting solution was evaporated under reduced pressure to dryness to give crude isocyanate (39), which was dissolved in dry DMF (2 mL). To this solution was added dropwise a solution of 4-[(6-methyl[1,3]-dioxolo[4,5-g]quinolin-8-yl)oxy]phenylamine (0.589 g, 2 mmol) in dry DMF (10 mL) containing $Et_3N$ (1.5 mL) at room temperature and then stirred for 5 h. The resulting solution was evaporated under reduced pressure to dryness and the solid residue was chromatographed on a silica gel column (3×35 cm) using $CHCl_3$ as the eluent. The main fractions containing the desired product were combined and concentrated under reduced pressure. The resulting solid was collected by filtration, and recrystallized from $CHCl_3$ to yield N-{4-[bis(2-chloroethyl)amino]phenyl}-N'-{4-[(6-methyl[1,3]dioxolo[4,5-g]-quinolin-8-yl)oxy]phenyl}urea (32, BO-1262); 0.556 g (50.2%): mp 217-218° C.; $^1$H NMR (DMSO-$d_6$) δ 2.43 (3H, s, Me), 3.70 (8H, s, 4×$CH_2$), 6.20 (2H, s, $CH_2$), 6.36 (1H, s, ArH), 6.72 (2H, d, J=8.52 Hz, ArH), 7.14 (2H, d, J=8.76 Hz, ArH), 7.27-7.30 (3H, m, ArH), 7.48 (1H, s, ArH), 7.55 (2H, d, J=8.60 Hz, ArH), 8.39 (1H, s, exchangeable, NH), 8.69 (1H, s, exchangeable, NH). Anal. Calcld. for ($C_{28}H_{26}Cl_2N_4O_4$): C, 60.77; H, 4.74; N, 10.12. Found: C, 60.55; H, 4.76; N, 10.32.

Compound BO-1263

BO-1263

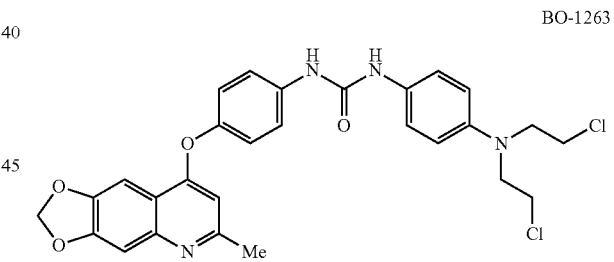

A mixture of 4-[N,N-bis(2-chloroethyl)aminophenyl-4-nitrophenyl carbonate (50)[39-41] (0.590 g, 1.5 mmol) and 4-[(6-methyl[1,3]dioxolo[4,5-g]quinolin-8-yl)oxy]-phenylamine (0.294 g, 1 mmol) in pyridine was stirred overnight at room temperature and then evaporated in vacuo to dryness. The solid product was purified by column chromatography on a silica gel column (3×35 cm) using $CHCl_3$ as the eluent. The main fractions containing the desired product was combined and concentrated under reduced pressure to dryness and the solid residue was recrystallized from $CHCl_3$ to afford 4-[bis(2-chloroethyl)amino]phenyl-4-[(6-methyl[1,3]dioxolo[4,5-g]quinolin-8-yl)oxy]phenylcarbamate (33, BO-1263); 0.372 g (67.23%): mp 183-184° C.; $^1$H NMR (DMSO-$d_6$) δ 2.43 (3H, s, Me), 3.74 (8H, s, 4×$CH_2$), 6.20 (2H, s, $CH_2$), 6.77 (2H, d, J=9.12 Hz, ArH) 6.77 (2H, d, J=9.08 Hz, ArH), 7.20 (1H, d, J=8.92 Hz, ArH), 7.28 (1H, s, ArH), 7.47 (1H, s, ArH), 7.61 (2H, d, J=8.92 Hz, ArH), 10.20 (1H, s, exchangeable, NH). Anal. Calcld. for ($C_{28}H_{25}Cl_2N_3O_5$): C, 60.66; H, 4.55; N, 7.58. Found: C, 60.39; H, 4.67; N, 7.52.

Compound BO-1054

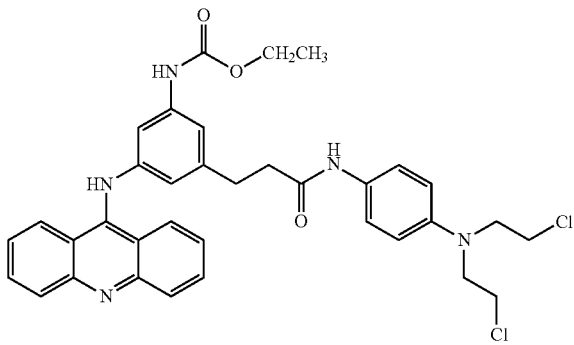

To a solution of N,N-bis(2-chloroethyl)benzene-1,4-diamine hydrochloride (18, 0.918 g, 3.0 mmol) in dry CHCl$_3$ (35 mL) containing Et$_3$N (0.6 mL) was added dropwise a solution of triphosgene (356 mg, 1.2 mmol.) in an ice bath with vigorous stirring for 30 min. The reaction mixture was evaporated and the residue diluted with THF (20 mL), filtered through a pad of Celite, washed with THF (5 mL). The filtrate containing crude N-mustard isocyanate 19 was evaporated in vacuo to dryness and the residue was dissolved in dry DMF (5 mL) and then added dropwise into a solution of [3-(acridin-9-ylamino)-5-hydroxymethyl-phenyl]carbamic acid ethyl ester[52] (0.988 g, 2.5 mmol) in dry DMF (25 mL) containing pyridine (2 mL) at −10° C. The reaction mixture was allowed to stir at room temperature for 24 h. The mixture was then evaporated in vacuo to dryness and the residue was dissolved in a mixture of CHCl$_3$/MeOH containing silica gel (10 g) and then evaporated in vacuo to dryness. The residue was put on the top of a silica gel column (4×30 cm) and chromatographed using CHCl$_3$/MeOH (100:3 v/v) as eluent. The fractions containing the main product were combined and evaporated in vacuo to dryness and the residue was recrystallized from CHCl$_3$/MeOH to give (3-(acridin-9-ylamino)-5-{4-[bis(2-chloroethyl)amino]phenylcarbamoyloxymethyl}phenyl)carbamic acid ethyl ester (BO-1054), 0.185 g (10.0%); mp 178-182° C.; $^1$H NMR (DMSO-d$_6$) δ 1.21 (3H, t, J=7.0 Hz, Me), 3.68 (8H, m, 4×CH$_2$), 4.08 (2H, q, J=7.0 Hz, CH$_2$), 5.02 (2H, s, CH$_2$), 6.65 (2H, d, J=9.0 Hz, ArH) 6.81-7.35 (6H, m, ArH), 7.39-7.95 (4H, m, ArH), 7.98-8.83 (3H, m, ArH), 9.36 (1H, brs, exchangeable, NH), 9.69 (2H, brs, exchangeable, NH). Anal. Calcld. for (C$_{34}$H$_{33}$Cl$_2$N$_5$O$_4$): C, 63.16; H, 5.14; N, 10.83. Found: C, 62.93; H, 5.04; N, 10.58.

Compound BO-2189

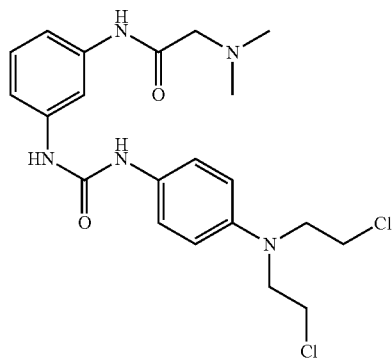

1) Preparation of 1-(4-(bis(2-chloroethyl)amino)phenyl)-3-(3-nitrophenyl)urea (45a)

To a stirred mixture of N-mustard amine 18 (7.66 g, 25 mmol) and triethylamine (TEA, (4 mL, 27.5 mmol) in CHCl$_3$ (100 mL) was added a solution of 3-nitrophenyl isocyanate 44a (4.1 g, 25 mmol) in CHCl$_3$ (50 mL) dropwise at room temperature. After being stirred additional 40-45 minutes, the solvent was removed by evaporation under reduced pressure and the solid residue was triturated with saturated aqueous solution of NaHCO$_3$ and then collected by filtration. The solid was washed with water, hexane, and dried. The solid was recrystallized from ethyl acetate to give 1-(4-(bis(2-chloroethyl)amino)phenyl)-3-(3-nitrophenyl)urea (45a), 9.1 g (92%); mp 246-247° C. $^1$H NMR (DMSO-d$_6$) δ: 3.69-3.71 (8H, m, CH$_2$), 6.71-6.74 (2H, d, J=9.0 Hz, Ar—H), 7.29-7.31 (2H, d, J=8.9 Hz, Ar—H), 7.52-7.56 (1H, t, J=8.1 and 8.2 Hz, Ar—H), 7.69-7.71 (1H, d, J=8.0 Hz, Ar—H), 7.78-7.80 (1H, q, J=8.2 and 1.8 Hz, Ar—H), 8.52 (1H, brs, NH), 8.54-8.55 (1H, d, J=2 Hz, Ar—H), 9.11 (1H, brs, NH).

2) Preparation of 1-(3-aminophenyl)-3-(4-(bis(2-chloroethyl)amino)phenyl)urea (46a)

The solution of compound 45a (3.5 g, 8.8 mmol) in ethyl acetate (100 mL) was hydrogenated with H$_2$ gas in Parr hydrogenator using 10% Pd—C (0.8 g) as a catalyst at 30-35 psi for 6-7 hours. After completion of the reaction, the mixture was filtered through celite pad and filtrate was evaporated to dryness under reduced pressure to afford 1-(3-aminophenyl)-3-(4-(bis(2-chloroethyl)amino)phenyl)urea (46a), 3.0 g (93%); mp 182-183° C. $^1$H NMR (DMSO-d$_6$) δ: 3.66-3.72 (8H, m, CH$_2$), 5.22 (2H, brs, NH$_2$), 6.17-6.19 (1H, d, J=8.0 Hz, Ar—H), 6.54-6.56 (1H, d, J=7.9 Hz, Ar—H), 6.69-6.71 (2H, d, J=9.0 Hz, Ar—H), 6.86 (1H, s, Ar—H), 6.88-6.90 (1H, t, J=8.0 Hz, Ar—H), 7.25-7.28 (2H, d, J=8.9 Hz, Ar—H), 8.27 (2H, br s, NH).

3) Preparation of N-(3-(3-(4-(bis(2-chloroethyl)amino)phenyl)ureido)-phenyl)-2-chloroacetamide To a solution of 46a (3.0 g, 8.0 mmol) in THF (100 mL), chloroacetyl chloride (2.2 g, 20 mmol) in THF (50 mL) was added dropwise at RT and the resulting mixture was stirred at RT for additional 45 minutes. The reaction mixture was evaporated under reduced pressure and the solid residue was triturated with saturated aqueous solution of NaHCO$_3$ and then filtered. The solid was washed successfully with water and hexane, and dried to yield N-(3-(3-(4-(bis(2-chloroethyl)amino)-phenyl)ureido)phenyl)-2-chloroacetamide, 2.8 g (82%); mp 232-233° C. $^1$H NMR (DMSO-d$_6$) δ: 2.80-2.83 (2H, t, J=5.9 Hz, CH$_2$), 3.68-3.71 (8H, m, CH$_2$), 3.86-3.89 (2H, t, J=5.9 Hz, CH$_2$), 6.70-6.72 (2H, d, J=8.5 Hz, Ar—H), 7.14-7.30 (5H, m, Ar—H), 7.76 (1H, s, Ar—H), 8.46 (1H, brs, NH), 8.73 (1H, brs, NH), 10.04 (1H, brs, NH).

4) Preparation of N-(3-(3-(4-(Bis(2-chloroethyl)amino)phenyl)ureido)-phenyl)-2-(dimethyl-amino)acetamide hydrochloride To a solution of N-(3-(3-(4-(bis(2-chloroethyl)amino)phenyl)ureido)phenyl)-2-chloroacetamide (0.88 g, 2 mmol) in THF (50 mL) was added dropwise dimethylamine (2M solution in THF) (2 mL, 4.0 mmol). The reaction mixture was heated at 50-60° C. for overnight. After cooling the mixture, the solvent was removed by evaporation under reduced pressure. The residue obtained was triturated with saturated aqueous solution of NaHCO$_3$. The solid product was collected by filtration, washed successively with water and hexane, and dried to yield N-(3-(3-(4-(bis(2-chloroethyl)amino)phenyl)

ureido)phenyl)-2-(dimethyl-amino)acetamide (BO-2189), 0.56 g (62%), mp 62-64° C. The product was dissolved in ethanol and excess of HCl in ethylacetate was added. The solution was evaporated in vacuo to dryness and the residue was co-evaporated several times with EtOH to dryness to form BO-2189 hydrochloride. $^1$H NMR (DMSO-$d_6$) δ: 2.88 (6H, s, CH$_3$), 3.68-3.71 (8H, m, CH$_2$), 4.13 (2H, s, CH$_2$), 6.71-6.73 (2H, d, J=8.8 Hz, Ar—H), 7.16-7.30 (5H, m, Ar—H), 7.78 (1H, s, Ar—H), 8.95 (1H, brs, NH), 9.24 (1H, brs, NH), 9.99 (1H, brs, NH). $^{13}$C NMR (CDCl$_3$, 125 MHz) δ: 41.09, 43.25, 52.73, 57.88, 108.84, 112.56, 113.17, 113.55, 120.03, 129.04, 138.31, 140.73, 152.86, 162.91. HRMS [ES$^+$]: calcd for $C_{21}H_{27}Cl_2N_5O_2$, 452.3774 [M+H]$^+$. found 452.1620. HPLC 97.3%.

Compound BO-2151

BO-2151

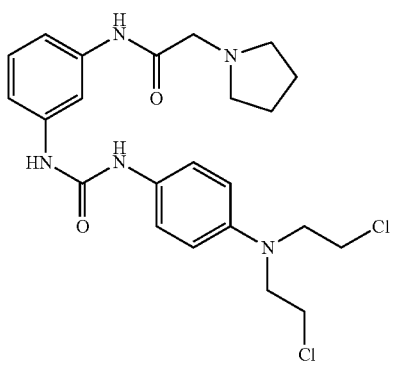

By following the same procedure as that for BO-2189, N-(3-(3-(4-(bis(2-chloroethyl)amino)phenyl)ureido)-phenyl)-2-(pyrrolidin-1-yl)acetamide (BO-2151) hydrochloride was prepared from N-(3-(3-(4-(bis(2-chloroethyl)amino) phenyl)ureido)phenyl)-2-chloroacetamide (2.2 g, 5.0 mmol) and pyrrolidine (1.6 g, 20 mmol) in THF (50 mL), 1.6 g (69%), mp 66-68° C. $^1$H NMR (DMSO-$d_6$) δ: 1.90-1.93 (2H, m, CH$_2$), 1.98-2.01 (2H, m, CH$_2$), 3.11-3.15 (2H, m, CH$_2$), 3.61-3.64 (2H, m, CH$_2$), 3.66-3.72 (8H, m, CH$_2$), 6.72-6.74 (2H, d, J=7.8 Hz, Ar—H), 7.19-7.22 (2H, d, J=7.6 Hz, Ar—H), 7.29-7.32 (3H, m, Ar—H), 7.78 (1H, s, Ar—H), 9.04 (1H, brs, NH), 9.31 (1H, brs, NH), 10.35 (1H, brs, NH). $^{13}$C NMR (CDCl$_3$, 125 MHz) δ: 22.82, 41.05, 52.88, 54.04, 55.72, 108.81, 112.53, 113.50, 120.03, 129.05, 138.43, 140.72, 152.87, 163.35. HRMS [ES$^+$]: calcd for $C_{23}H_{29}Cl_2N_5O_2$, 478.4147 [M+H]$^+$. found 478.1777. HPLC 98.6%.

Compound BO-2147

BO-2147

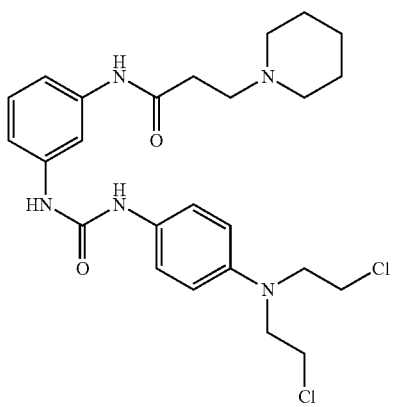

1) Preparation of N-(3-nitrophenyl)-3-(piperidin-1-yl)propanamide

By following the same procedure as that for compound 3-(dimethylamino)-N-(3-nitrophenyl)propanamide, N-(3-Nitrophenyl)-3-(piperidin-1-yl)propanamide was prepared from 3-chloro-N-(3-nitrophenyl)propanamide (4.6 g, 20 mmol) and piperidine (2.8 g, 40 mmol) in THF (50 mL). Yield 5.3 g (95%), mp 95-96° C. $^1$H NMR (DMSO-$d_6$) δ: 1.38-1.40 (2H, m, CH$_2$), 1.48-1.52 (4H, m, CH$_2$), 2.39-2.41 (4H, m, CH$_2$), 2.51-2.53 (2H, m, CH$_2$), 2.61-2.65 (2H, m, CH$_2$), 7.58-7.62 (1H, m, Ar—H), 7.86-7.90 (2H, m, Ar—H), 8.63-8.65 (1H, m, Ar—H), 10.61 (1H, brs, NH).

2) Preparation of N-(3-aminophenyl)-3-(piperidin-1-yl)propanamide

By following the same procedure as that for N-(3-aminophenyl)-3-(dimethylamino)propanamide, N-(3-aminophenyl)-3-(piperidin-1-yl)propanamide was prepared from N-(3-nitrophenyl)-3-(piperidin-1-yl)propanamide (4.34 g, 10 mmol) and 10% Pd/C (0.8 g) in ethyl acetate (100 mL) as a brown gum. Yield 3.4 g (89%). $^1$H NMR (DMSO-$d_6$) δ: 1.38 (2H, s, CH$_2$), 1.48 (4H, s, CH$_2$), 2.37 (6H, s, CH$_2$), 2.53 (2H, s, CH$_2$), 5.02 (2H, brs, NH$_2$), 6.21-6.23 (1H, m, Ar—H), 6.63-6.65 (1H, m, Ar—H), 6.86-6.89 (2H, m, Ar—H), 9.90 (1H, brs, NH).

3) Preparation of N-(3-(3-(4-(Bis(2-chloroethyl)amino)phenyl)ureido)-phenyl)-3-(piperidin-1-yl)-propanamide By following the same procedure as that for BO-2091, BO-2147 was prepared from N-(3-aminophenyl)-3-(piperidin-1-yl)propanamide (2.47 g, 10.0 mmol) and N-mustard isocyanate [19, freshly prepared from N-mustard amine hydrochloride 18 (6.1 g, 20 mmol)] in dry DMF. Yield: 4.2 g (82%); mp 108-110° C. The HCl salt of compound BO-2147 was prepared by following the same procedure as that for compound BO-2091. $^1$H NMR (DMSO-$d_6$) δ: 1.33-1.42 (1H, m, CH), 1.67-1.79 (5H, m, CH), 2.90-2.94 (4H, m, CH$_2$), 3.30-3.33 (2H, m, CH$_2$), 3.38-3.42 (2H, m, CH$_2$), 3.69-3.74 (8H, m, CH$_2$), 6.73-6.75 (2H, m, Ar—H), 7.16-7.18 (2H, m, Ar—H), 7.26-7.27 (3H, m, Ar—H), 7.72 (1H, s, Ar—H), 8.95 (1H, brs, NH), 9.14 (1H, brs, NH), 10.33 (1H, brs, NH). $^{13}$C NMR (CDCl$_3$, 125 MHz) δ: 21.32, 22.37, 30.53, 40.89, 51.79, 52.13, 53.14, 108.79, 112.57, 113.03, 113.97, 119.99, 128.88, 139.31, 140.50, 152.87, 167.79. HRMS [ES$^+$]: calcd for $C_{25}H_{33}Cl_2N_5O_2$, 506.4678 [M+H]$^+$. found 506.2090. HPLC 98.8%.

Compound BO-2191

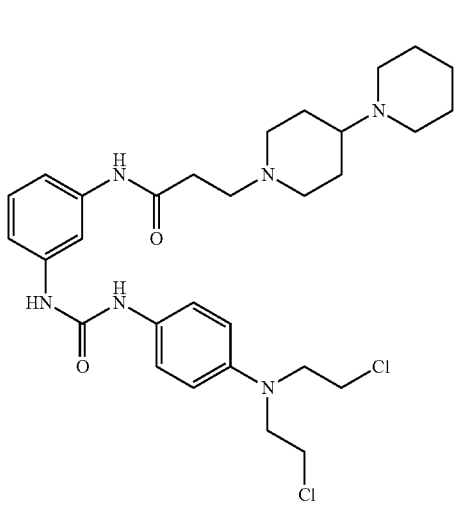

BO-2191

Compound BO-2091

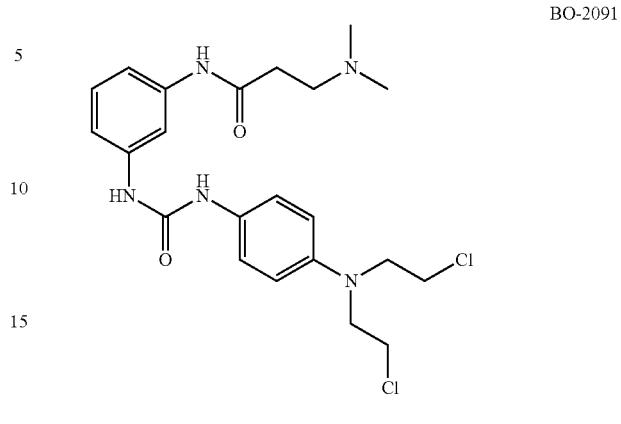

BO-2091

1) Preparation of N-(3-(3-(4-(Bis(2-chloroethyl)amino)phenyl)ureido)-phenyl)-3-chloropropanamide To a solution of 1-(3-aminophenyl)-3-(4-(bis(2-chloroethyl)amino)phenyl)urea (46a) (3.0 g, 8.0 mmol) in THF (100 mL) was added dropwise 3-chloropropionyl chloride (2.5 g, 20 mmol) in THF (200 mL) at RT and the resulting mixture was stirred at RT for 40-45 minutes and then evaporated to dryness under reduced pressure. The solid residue was triturated with saturated aqueous solution of NaHCO$_3$ and collected by filtration. The solid product was washed successively with water and hexane, and dried to give N-(3-(3-(4-(bis(2-chloroethyl)amino)phenyl)-ureido)phenyl)-3-chloropropanamide, 2.8 g (82%), mp 232-233° C. $^1$H NMR (DMSO-d$_6$) δ: 2.80-2.83 (2H, t, J=5.9 Hz, CH$_2$), 3.68-3.71 (8H, m, CH$_2$), 3.86-3.89 (2H, t, J=5.9 Hz, CH$_2$), 6.70-6.72 (2H, d, J=8.5 Hz, Ar—H), 7.14-7.30 (5H, m, Ar—H), 7.76 (1H, s, Ar—H), 8.46 (1H, brs, NH), 8.73 (1H, brs, NH), 10.04 (1H, brs, NH).

2) Preparation of 3-([1,4'-bipiperidin]-1'-yl)-N-(3-(3-(4-(bis(2-chloroethyl)amino)-phenyl)ureido)phenyl) propanamide hydrochloride By following the same procedure as that for BO-2189, 3-([1,4'-bipiperidin]-1'-yl)-N-(3-(3-(4-(bis(2-chloroethyl)amino)phenyl)ureido)phenyl)propanamide hydrochloride (BO-2191) was prepared from N-(3-(3-(4-(bis(2-chloroethyl)amino)phenyl)ureido)phenyl)-3-chloropropanamide (0.92 g, 2.0 mmol) and 4-piperidinopiperidine (0.38 g, 2.2 mmol) in THF (50 mL). Yield: 1.0 g (84%), mp 134-136° C. $^1$H NMR (DMSO-d$_6$) δ: 1.39-1.42 (1H, m, CH), 1.68-1.71 (1H, m, CH), 1.76-1.91 (7H, m, CH), 1.97-1.99 (1H, m, CH), 2.13-2.20 (2H, m, CH$_2$), 2.33-2.36 (2H, m, CH$_2$), 2.93-3.04 (7H, m, CH), 3.60-3.71 (10H, m, CH$_2$), 6.71-6.73 (2H, d, J=8.6 Hz, Ar—H), 7.15-7.18 (2H, m, Ar—H), 7.28-7.30 (3H, m, Ar—H), 7.73 (1H, s, Ar—H), 8.91 (1H, brs, NH), 9.11 (1H, brs, NH), 10.29 (1H, brs, NH). $^{13}$C NMR (CDCl$_3$, 125 MHz) δ: 21.09, 21.43, 22.38, 23.09, 30.56, 41.11, 49.01, 50.24, 51.58, 52.76, 59.33, 10872, 112.50, 113.27, 120.03, 128.86, 139.25, 140.53, 152.87, 167.65, 171.97. HRMS [ES$^+$]: calcd for C$_{30}$H$_{42}$Cl$_2$N$_6$O$_2$, 589.5995 [M+H]$^+$. found 589.2825. HPLC 99.2%.

1) Preparation of 3-Chloro-N-(3-nitrophenyl)propanamide

To a stirred solution of 3-nitroaniline (37a, 6.9 g, 50 mmol) in THF (50 mL) was added dropwise 3-chloropropionyl chloride (10 mL, 100 mmol) over 30 min under argon atmosphere. The reaction was stirred at 50° C. for 10 h. After cooling, the reaction mixture was evaporated to dryness under vacuo and the residue was neutralized with saturated aqueous solution of NaHCO$_3$ and the solid product was collected by filtration, washed with water followed by hexane, and dried to afford 3-chloro-N-(3-nitrophenyl)propanamide, 10.61 g (92%), mp 86-88° C. (Lit. 100-102° C.[57]). $^1$H NMR (DMSO-d$_6$) δ: 2.87-2.90 (2H, t, J=9.9 Hz, CH$_2$), 3.90-3.92 (2H, t, J=9.9 Hz, CH$_2$), 7.61-7.64 (1H, t, J=6.6 and 6.6 Hz, Ar—H), 7.90-7.94 (2H, m, Ar—H), 8.65-8.66 (1H, t, J=3.4 and 1.7 Hz, Ar—H), 10.59 (1H, brs, NH).

2) Preparation of 3-(Dimethylamino)-N-(3-nitrophenyl)propanamide

To a stirred solution of 3-chloro-N-(3-nitrophenyl)propanamide (4.6 g, 20 mmol) in THF (50 mL) was added dropwise N,N-dimethyl amine (2M solution in THF) (1.8 g, 20 mL, 40 mmol) at room temperature. The resulting mixture was stirred at room temperature overnight and then evaporated to dryness under reduced pressure. The residue was triturated with 5% NH$_3$ (aqueous, 50 mL) and the solid product was collected by filtration, washed with water followed by hexane, and dried to give 3-(dimethylamino)-N-(3-nitrophenyl)propanamide, 4.1 g (87%), mp 80-81° C. $^1$H NMR (DMSO-d$_6$) δ: 2.17 (6H, s, CH$_3$), 2.47-2.50 (2H, t, J=6.4 Hz, CH), 2.56-2.59 (2H, t, J=6.8 Hz, CH), 7.57-7.62 (1H, t, J=8.2 Hz, Ar—H), 7.88-7.91 (2H, dd, J=8.1 and 2.2 Hz, Ar—H), 8.63-8.64 (1H, t, J=2.0 Hz, Ar—H), 10.49 (1H, brs, NH).

3) Preparation of N-(3-aminophenyl)-3-(dimethylamino)propanamide

10% Palladium on charcoal (1.0 g) was suspended in a solution of 3-(dimethylamino)-N-(3-nitrophenyl)propanamide (4.7 g, 20 mmol) in ethyl acetate. The mixture was hydrogenated at 35 psi overnight. The reaction was filtered through a pad of Celite. The filter cake was washed successively with ethyl acetate and methanol. The combined filtrate and washings were evaporated in vacuo to dryness to give N-(3-aminophenyl)-3-(dimethylamino)propanamide as brown gum, 3.9 g (94%). $^1$H NMR (DMSO-$d_6$) δ: 2.16 (6H, s, $CH_3$), 2.36 (2H, t, J=6.8 Hz, $CH_2$), 3.40 (2H, t, J=6.8 Hz, $CH_2$), 5.20 (2H, brs, $NH_2$), 6.66 (1H, d, J=7.8 Hz, Ar—H), 6.91 (1H, d, J=7.7 Hz, Ar—H), 7.04 (1H, s, Ar—H), 7.15 (1H, t, J=7.4 Hz, Ar—H), 9.05-9.08 (1H, brs, NH).

4) Preparation of N-(3-(3-(4-(bis(2-chloroethyl)amino)phenyl)ureido)-phenyl)-3-(dimethyl-amino)propanamide To a stirred solution of N-(3-aminophenyl)-3-(dimethylamino)propanamide (1.15 g, 5.5 mmol) in dry DMF (20 mL) containing TEA (1.6 mL) was added a solution of N,N-bis(2-chloroethyl)-4-isocyanatoaniline [7, freshly prepared from $N^1,N^1$-bis-(2-chloroethyl)benzene-1,4-diamine hydrochloride 6 (3.4 g, 11 mmol) and triphosgene in chloroform] in dry DMF (5 mL)) at room temperature. After being stirred overnight at room temperature, the solid was filtered and washed with dry DMF. The filtrate was evaporated to dryness in vacuo and the product was purified by column chromatography using $CHCl_3$/MeOH (100:10 v/v) as an eluent. The fractions containing main product were combined and evaporated to dryness under vacuum to afford compound N-(3-(3-(4-(bis(2-chloroethyl)amino)-phenyl)ureido)phenyl)-3-(dimethylamino)-propanamide (BO-2091), 2.2 g (62%); mp 88-90° C. The HCl salt of BO-2091 was prepared by treating the compound with HCl/EtOAc in a mixture of EtOAc:MeOH (10:1, v/v, 50 mL) under argon atmosphere during 30-40 min at room temperature. Solvent was then evaporated to dryness to give HCl salt of BO-2091. $^1$H NMR (DMSO-$d_6$) δ: 2.77 (6H, s, $CH_3$), 2.84-2.87 (2H, t, J=7.1 Hz, $CH_2$), 3.32-3.35 (2H, t, J=6.7 Hz, $CH_2$), 3.68-3.70 (8H, m, $CH_2$), 6.71-6.73 (2H, d, J=8.6 Hz, Ar—H), 7.27-7.29 (2H, d, J=8.8 Hz, Ar—H), 7.36-7.38 (2H, d, J=8.8 Hz, Ar—H), 7.48-7.50 (2H, d, J=8.8 Hz, Ar—H), 7.95 (1H, brs, NH), 8.82 (1H, brs, NH), 9.02 (1H, brs, NH). $^{13}$C NMR ($CDCl_3$, 125 MHz) δ: 30.50, 41.00, 42.10, 52.52, 52.58, 112.95, 117.95, 119.74, 120.02, 130.64, 132.64, 135.77, 140.96, 152.85, 167.25. HRMS [ES$^+$]: calcd for $C_{22}H_{29}Cl_2N_5O_2$, 466.4040 [M+H]$^+$. found 466.1771. HPLC 98.7%.

Compound BO-2094

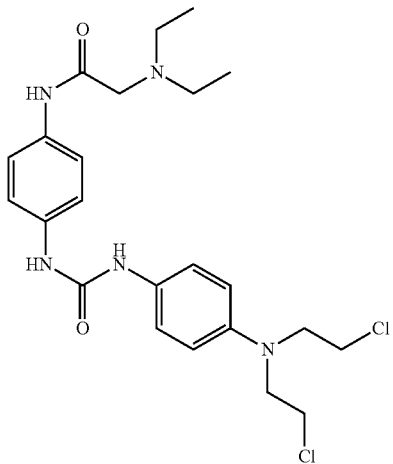

BO-2094

1) Preparation of 2-Chloro-N-(4-nitrophenyl)acetamide

To a solution of 4-nitroaniline 37b (6.9 g, 50 mmol) in THF (50 mL) was added dropwise a solution of chloroacetyl chloride (100 mmol) in dry THF (50 mL) at room temperature. The reaction mixture was stirred for additional 40-45 minutes and then evaporated in vacuo to dryness. The solid residue was triturated with saturated $NaHCO_3$ solution (aqueous) and then collected by filtration. The solid product was washed with water, followed by hexane, and dried to give 2-chloro-N-(4-nitrophenyl)acetamide, 10.02 g (94%); mp 182-183° C. (Lit. 181-183° C.$^{58}$). $^1$H NMR (DMSO-$d_6$) δ: 4.34 (2H, s, $CH_2$), 7.83-7.85 (2H, d, J=9.1 Hz, Ar—H), 8.23-8.26 (2H, d, J=9.1 Hz, Ar—H), 10.88 (1H, brs, NH).

2) Preparation of 2-Diethylamino-N-(4-nitrophenyl)acetamide

By following the same procedure as that for 3-(dimethylamino)-N-(3-nitrophenyl)propanamide, 2-diethylamino-N-(4-nitrophenyl)acetamide was prepared from 2-chloro-N-(4-nitrophenyl)acetamide and N,N-diethyl amine (1.4 g, 20 mmol) in THF (50 mL). Yield: 1.7 g (67%); mp 65-66° C. (Lit. 68-70° C.$^{59}$). $^1$H NMR (DMSO-$d_6$) δ: 1.01-1.05 (6H, t, J=7.0 Hz, $CH_3$), 2.65-2.67 (4H, m, $CH_2$), 3.32 (2H, s, $CH_2$), 7.93-7.95 (2H, d, J=9.0 Hz, Ar—H), 8.21-8.24 (2H, d, J=9.1 Hz, Ar—H), 10.34 (1H, brs, NH).

3) Preparation of N-(4-Aminophenyl)-2-(diethylamino)acetamide

By following the same procedure as that for N-(3-aminophenyl)-3-(dimethylamino)propanamide, N-(4-aminophenyl)-2-(diethylamino)acetamide was prepared from 2-diethylamino-N-(4-nitrophenyl)acetamide (1.6 g, 8.5 mmol) and 10% Pd/C (0.4 g) in ethyl acetate (100 mL) as a brown gum.$^{60}$ Yield: 1.3 g (95%). $^1$H NMR (DMSO-$d_6$) δ: 1.02-1.06 (6H, t, J=7.1 Hz, $CH_3$), 2.64-2.69 (4H, q, J=6.9 Hz, $CH_2$), 3.21 (2H, s, $CH_2$), 5.19 (2H, brs, $NH_2$), 6.50-6.52 (2H, d, J=8.6 Hz, Ar—H), 7.23-7.25 (2H, d, J=8.6 Hz, Ar—H), 9.41 (1H, brs, NH).

4) Preparation of N-(4-(3-(4-(Bis(2-chloroethyl)amino)phenyl)ureido)-phenyl)-2-(diethylamino)-acetamide BO-2094 was prepared by following the same procedure as that for BO-2091 using N-(4-aminophenyl)-2-(diethylamino)acetamide (1.2 g, 5.5 mmol) and N-mustard isocyanate 7 [freshly prepared from N-mustard amine 6 hydrochloride (3.3 g, 11 mmol)] in dry DMF. Yield: 1.4 g (48%); mp 209-211° C. The HCl salt of BO-2094 was prepared by following the same procedure as that for BO-2091. $^1$H NMR (DMSO-$d_6$) δ: 1.23-1.27 (6H, t, J=7.2 Hz, $CH_3$), 3.22-3.26 (4H, q, J=7.5 Hz, $CH_2$), 3.69-3.70 (8H, m, $CH_2$), 4.13 (2H, s, $CH_2$), 6.73-6.75 (2H, d, J=8.6 Hz, Ar—H), 7.28-7.30 (2H, d, J=8.8 Hz, Ar—H), 7.41-7.43 (2H, d, J=8.9 Hz, Ar—H), 7.51-7.54 (2H, d, J=8.9 Hz, Ar—H), 8.96 (1H, brs, NH), 9.22 (1H, brs, NH), 9.84 (1H, brs, NH). $^{13}$C NMR ($CDCl_3$, 125 MHz) δ: 9.37, 41.57, 48.90, 53.22, 53.31, 113.65, 118.53, 120.62, 130.39, 132.24, 137.10, 141.19, 153.43, 163.16. HRMS [ES$^+$]: calcd for $C_{23}H_{31}Cl_2N_5O_2$, 480.4305 [M+H]$^+$. found 480.1928. HPLC 97.7%.

Compound BO-2073

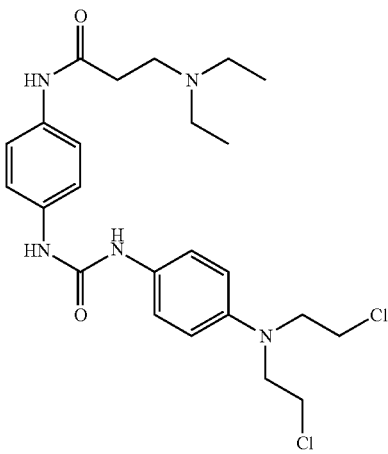

1) Preparation of 3-Chloro-N-(4-nitrophenyl)propanamide

By following the same method as that for 3-chloro-N-(3-nitrophenyl)propanamide, 3-chloro-N-(4-nitrophenyl)propanamide was prepared from 4-nitroaniline (6.9 g, 50 mmol) and 3-chloropropionyl chloride (10 mL, 100 mmol) in THF. Yield: 10.62 g (93%); mp 172-174° C. (Lit. 169-171° C.[58]). $^1$H NMR (DMSO-$d_6$) δ: 2.90-2.93 (2H, t, J=6.2 Hz, CH$_2$), 3.88-3.91 (2H, t, J=6.2 Hz, CH$_2$), 7.84-7.86 (2H, d, J=9.0 Hz, Ar—H), 8.22-8.24 (2H, d, J=9.0 Hz, Ar—H), 10.69 (1H, brs, NH).

2) Preparation of 3-(Diethylamino)-N-(4-nitrophenyl)propanamide

By following the same procedure as that for compound 3-(dimethylamino)-N-(3-nitrophenyl)propanamide, 3-(diethylamino)-N-(4-nitrophenyl)propanamide was prepared from 3-chloro-N-(4-nitrophenyl)propanamide (2.28 g, 10 mmol) and N,N-diethyl amine (1.4 g, 20 mmol) in THF (50 mL). Yield: 2.5 g (93%); mp 86-88° C. (Lit. 95-96° C.[61]). $^1$H NMR (DMSO-$d_6$) δ: 0.94-0.98 (6H, t, J=7.1 Hz, CH$_3$), 2.43-2.47 (6H, m, CH$_2$), 2.73-2.77 (2H, t, J=6.9 Hz, CH$_2$), 7.81-7.83 (2H, d, J=9.2 Hz, Ar—H), 8.20-8.23 (2H, d, J=9.1 Hz, Ar—H), 10.72 (1H, brs, NH).

3) Preparation of N-(4-Aminophenyl)-3-(diethylamino)propanamide

By following the same procedure as that for N-(3-aminophenyl)-3-(dimethylamino)propanamide, N-(4-aminophenyl)-3-(diethylamino)propanamide was prepared from 3-(diethylamino)-N-(4-nitrophenyl)propanamide (2.0 g, 7.5 mmol) and 10% Pd/C (0.4 g) in ethyl acetate (100 mL) as brown gum.[61] Yield: 1.6 g (92%); $^1$H NMR (DMSO-$d_6$) δ: 0.95-0.99 (6H, t, J=7.1 Hz, CH$_3$), 2.31-2.34 (2H, t, J=7.0 Hz, CH$_2$), 2.46-2.52 (4H, q, J=7.0 Hz, CH$_2$), 2.69-2.72 (2H, t, J=7.0 Hz, CH$_2$), 4.82 (2H, brs, NH$_2$), 6.48-6.50 (2H, d, J=8.6 Hz, Ar—H), 7.19-7.21 (2H, d, J=8.6 Hz, Ar—H), 9.71 (1H, brs, NH).

4) Preparation of N-(4-(3-(4-(Bis(2-chloroethyl)amino)phenyl)ureido)-phenyl)-3-(diethylamino)-propanamide By following the same procedure as that for BO-2091, BO-2073 was prepared from N-(4-aminophenyl)-3-(diethylamino)propanamide (1.2 g, 5.0 mmol) and N-mustard isocyanate 7 [freshly prepared from N-mustard amine hydrochloride 6 (3.0 g, 10 mmol)] in dry DMF. Yield: 1.6 g (85%); mp 178-179° C. The HCl salt of BO-2073 was prepared by following the same procedure as that for BO-2091. $^1$H NMR (DMSO-$d_6$) δ: 1.22-1.25 (6H, t, J=7.1 Hz, CH$_3$), 2.85-2.88 (2H, t, J=7.1 Hz, CH$_2$), 3.11-3.14 (4H, m, CH$_2$), 3.33-3.34 (2H, m, CH$_2$), 3.68-3.70 (8H, m, CH$_2$), 6.73-6.75 (2H, d, J=8.2 Hz, Ar—H), 7.28-7.30 (2H, d, J=8.6 Hz, Ar—H), 7.36-7.38 (2H, d, J=8.7 Hz, Ar—H), 7.49-7.51 (2H, d, J=8.8 Hz, Ar—H), 8.90 (1H, brs, NH), 9.09 (1H, brs, NH), 10.26 (1H, brs, NH). $^{13}$C NMR (CDCl$_3$, 125 MHz) δ: 8.35, 30.11, 41.07, 46.32, 46.72, 52.49, 112.76, 118.0, 119.71, 120.09, 130.39, 132.69, 135.74, 141.19, 152.83, 167.22. HRMS [ES$^+$]: calcd for C$_{24}$H$_{33}$Cl$_2$N$_5$O$_2$, 494.4571 [M+H]$^+$. found 494.2078. HPLC 96.6%.

Compound BO-2092

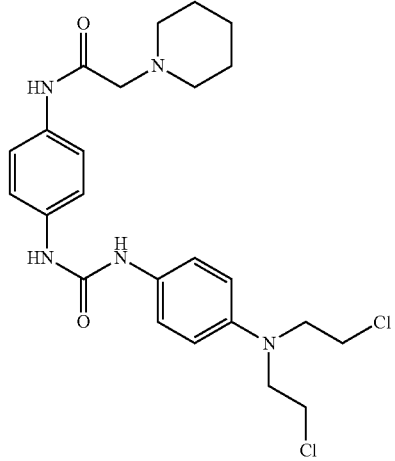

1) Preparation of N-(4-Nitrophenyl)-2-(piperidin-1-yl)acetamide

By following the same procedure as that for compound 3-(dimethylamino)-N-(3-nitrophenyl)propanamide, N-(4-nitrophenyl)-2-(piperidin-1-yl)acetamide was prepared from 2-chloro-N-(4-nitrophenyl)acetamide (2.15 g, 10 mmol) and piperidine (1.7 g, 20 mmol) in THF (50 mL). Yield: 2.6 g, (98%); mp 144-145° C. (Lit. 143-145° C.[59]). $^1$H NMR (DMSO-$d_6$) δ: 1.40-1.43 (2H, m, CH$_2$), 1.54-1.59 (4H, m, CH$_2$), 2.45-2.47 (4H, m, CH$_2$), 3.14 (2H, s, CH$_2$), 7.91-7.93 (2H, d, J=9.2 Hz, Ar—H), 8.21-8.23 (2H, d, J=9.2 Hz, Ar—H), 10.28 (1H, brs, NH).

2) Preparation of N-(4-Aminophenyl)-2-(piperidin-1-yl)acetamide

By following the same procedure as that for N-(3-aminophenyl)-3-(dimethylamino)propanamide, N-(4-aminophenyl)-2-(piperidin-1-yl)acetamide was prepared from N-(4-nitrophenyl)-2-(piperidin-1-yl)acetamide (2.4 g, 9.1 mmol) and 10% Pd/C (0.5 g) in ethyl acetate (100 mL). Yield: 2.1 g (98%), mp 106-107° C. (Lit. 107-108° C.[60]). $^1$H NMR (DMSO-$d_6$) δ: 1.39-1.40 (2H, m, CH$_2$), 1.52-1.58 (4H, m, CH$_2$), 2.43-2.50 (4H, m, CH$_2$), 2.97 (2H, m, CH$_2$), 4.85 (2H, brs, NH$_2$), 6.49-6.51 (2H, d, J=8.6 Hz, Ar—H), 7.2-7.24 (2H, d, J=8.6 Hz, Ar—H), 9.19 (1H, brs, NH).

3) Preparation of N-(4-(3-(4-(bis(2-chloroethyl) amino)phenyl)ureido)-phenyl)-2-(piperidin-1-yl)-acetamide By following the same procedure as that for BO-2091, BO-2092 was prepared from N-(4-aminophenyl)-2-(piperidin-1-yl)acetamide (2.0 g, 8.6 mmol) and N-mustard isocyanate 7 [freshly prepared from N-mustard amine hydrochloride 6 (5.3 g, 17 mmol)] in dry DMF. Yield: 1.9 g (44%); mp 227-229° C. The HCl salt of compound BO-2092 was prepared by following the same procedure as that for BO-2091. $^1$H NMR (DMSO-$d_6$) δ: 1.40-1.41 (1H, m, CH), 1.69-1.79 (6H, m, $CH_2$), 3.07-3.08 (2H, m, $CH_2$), 3.46-3.49 (2H, m, $CH_2$), 3.68-3.72 (8H, m, $CH_2$), 4.08 (2H, s, $CH_2$), 6.70-6.72 (2H, d, J=9.0 Hz, Ar—H), 7.27-7.29 (2H, d, J=8.9 Hz, Ar—H), 7.41-7.43 (2H, d, J=8.9 Hz, Ar—H), 7.50-7.52 (2H, d, J=8.9 Hz, Ar—H), 8.79 (1H, brs, NH), 9.05 (1H, brs, NH), 9.85 (1H, brs, NH). $^{13}$C NMR (CDCl$_3$, 125 MHz) δ: 21.55, 22.66, 41.69, 53.05, 53.41, 57.48, 113.30, 118.57, 120.64, 120.70, 130.87, 132.19, 137.07, 141.91, 153.42, 162.70. HRMS [ES$^+$]: calcd for $C_{24}H_{31}Cl_2N_5O_2$, 492.4412 [M+H]$^+$. found 492.1928. HPLC 98.6%.

Example 3

Biological Methods and Materials

Tumor and Cell Lines.

Human colon carcinoma HCT-116 cells and human glioma U87GM cells were obtained from American Type Culture Collection (ATCC, Rockville, Md.). Human mammary carcinoma (MX-1) tumor cells were obtained from MSKCC cell bank. The CCRF-CEM human lymphoblastic leukemia cells and their vinblastine resistant subline (CCRF-CEM/VBL, 680-fold resistance in vitro) were obtained from Dr. William Beck of the University of Illinois, Chicago, and CCRF-CEM/Taxol (330-fold resistance in vitro). Resistant cells CCRF-CEM/taxol were produced by exposing the parent cells to increasing sublethal concentration ($IC_{50}$-$IC_{90}$) of paclitaxel for six months.

In Vitro Cytotoxicity Assays.

In preparation for in vitro cytotoxicity assays, cells were cultured at an initial density 2-5×10$^4$ cells per milliliter. They were maintained in a 5% $CO_2$-humidified atmosphere at 37° C. in RPMI medium 1640 (GIBCO/BRL) containing penicillin (100 units/mL), streptomycin (100 μg/mL, GIBCO/BRL), and 5% heat-inactivated FBS. For cells grown in suspension (such as CCRF-CEM and its sublines), cytotoxicity was measured, by using XTT microculture method[62] in 96-well microtiter plates. For solid tumor cells growing in a monolayer (such as MX-1 and HCT-116), cytotoxicity of the drug was determined, in duplicate, in 96-well microtiter plates by using the sulforhodamine B method.[63] For both methods, the absorbance of each well was measured with a microplate reader (Power Wave XS, Bio-Tek, Winooski, Vt.) after 72-hr incubation as described previously.[64] Dose-effect relationship data from 6 to 7 concentrations of each drug, in duplicate, were analyzed by using a computer program[65] based on the median-effect principle and plot.[66,67]

Animals.

Athymic nude mice bearing the nu/nu gene were obtained from NCI, Frederick, Md. and used for all human tumor xenografts. Male nude mice 6 weeks or older weighing 20-24 g or more were used. Compounds were administered via the tail vein for i.v. injection or infusion as described previously.[64] A typical formulation for chemotherapeutic studies for each drug was dissolved in DSMO to make a 25 mg/ml fresh solution, 0.4 ml of this solution was mixed with 0.3 ml of Tween 80, plus 1.3 ml to make 2 ml of 5 mg/ml solution. Bolus injection volume was 0.1-0.2 ml per mouse. Tumor volume was assessed by measuring length×width×height (or width) by using a caliper. For tumor-bearing nude mice during the course of the experiment, the body weight refers to total weight minus the weight of the tumor. All animal studies were conducted in accordance with the guidelines for the National Institute of Health Guide for the Care and Use of Animals and the protocol approved by the Institutional Animal Care and Use Committee.

Definition and Quantitative Determination of Therapeutic Effects in Nude Mice.

The therapeutic effects of a drug against human tumor xenografts in nude mice, under the optimal therapeutic conditions but without any lethality due to drug toxicity, the following degrees of therapeutic effects are defined and calculated by the following formula:

$$\text{Tumor suppression (\%)} = \left\{1 - \left[\frac{(T_c - T_0) - (T_x - T_0)}{(T_c - T_0)}\right]\right\} \times 100,$$

where $T_0$ is the initial tumor size (in mm$^3$) at beginning of drug treatment;

$T_c$ is tumor size of untreated control group on a given date; and $T_x$ is tumor size of the drug treated group on a given date.

$$\text{Tumor shrinkage (\%)} = \left\{1 - \left[\frac{(T_0 - T_x)}{(T_0)}\right]\right\} \times 100 \quad \text{Eq. 2)}$$

Where $T_0$ and $T_x$,

Tumor disappearance (complete remission or CR) is defined by the effect where

[$T_x$=0] for a period of time (in days) for a proportion of animals ($N_{CR}$/N), where N is the total number of animals in the group, and $N_{CR}$ is the number of mice in the group that achieved CR.

Tumor relapse is quantitatively calculated by

[The Day tumor relapsed ($D_{relp}$)—The Day CR achieved ($D_{CR}$)] (Eq. 3) for a proportion of animals ($N_{relp}$/N) where N is the total number of animals in the group, and $N_{relp}$ is the number of the mice in the group that relapsed.

The log cell kill (LCK) of the tumor tissue after a given chemotherapy that reached CR is estimated by:

$$LCK = \log [2^{(\text{Tumor remission in days/Tumor doubling time in days})}] \quad \text{(Eq. 4)}$$

We have designed and synthesized a series of aniline and phenol N-mustard linked to DNA-affinic carriers (such as 9-anilinoacridines, acridines and quinolines), aminobenzamides or aminophenol ethers with a urea or carbamic acid ester linkage. The linkers located at the para-position of the N-mustard residue are able deactivate the reactivity of the DNA cross-linking phrmacophore. These agents are more stable than alkyl N-mustard derivatives. For example, the half-life ($t_{1/2}$) for BO-1051 was about 45 days in intravenous injection vehicle (DMSO/Tween 80/Saline) and has long half-life in rat plasma with $t_{1/2}$=54 h. The antitumor studies of the newly invented N-mustards demonstrated that these agents possess potent antitumor therapeutic efficacy and have potential for clinical applications.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Determination of DNA Interstrand Cross-Linking.

Formation of DNA cross-linking was analyzed by alkaline agarose gel electrophoresis. In brief, purified pEGFP-N1 plasmid DNA (1500 ng) was mixed with various concentrations (1-20 μM) of the tested compounds in 40 μL binding buffer (3 mM sodium chloride/1 mM sodium phosphate, pH 7.4, and 1 mM EDTA). The reaction mixture was incubated at 37° C. for 2 h. At the end of reaction, the plasmid DNA was linearized by digestion with BamHI and followed by precipitation with ethanol. The DNA pellets were dissolved and denatured in alkaline buffer (0.5 N NaOH-10 mM EDTA). An aliquot of 20 μL of DNA solution (1000 ng) was mixed with 4 μL of 6× alkaline loading dye and then electrophoretically resolved on a 0.8% alkaline agarose gel with NaOH-EDTA buffer at 4° C. The electrophoresis was carried out at 18V for 22 h. After staining the gels with an ethidium bromide solution, the DNA was then visualized under UV light.

Example 4

Biological Results

In Vitro Cytotoxicity

All representative compounds of Formulae (I-A), (I-B) and (I-C) were evaluated for their in vitro and in vivo cytotoxicity. Tables 1 and 2 show the potency of inhibiting tumor cell growth by the newly synthesized derivatives in vitro. The $IC_{50}$ is defined by the concentration required to inhibit tumor cell growth by 50%. It demonstrated that these agents exhibited potent cytotoxicity against human lymphoblastic leukemis (CCRF/CEM) as well as the solid tumors (mammary MX-1 and colon HCT-116) cell growth in vitro with submicromolar $IC_{50}$ values. The growth inhibition against human lymphoblastic leukemic cells (CCRF-CEM) and its drug-resistant sublines (resistant to vinblastine and taxol, CCRF-CEM/VBL and CCRF-CEM/taxol, respectively) by the newly synthesized was also indicated in Table 1. The results revealed that these compounds have little or no cross-resistance to either taxol or vinblastine. With one exception, BO-1037 was cross-resistant to these two antitumor agents. It suggested that most N-mustard derivatives were neither a good substrate of membrane of p-glycoprotein nor mutated tubulin.

For compounds of Formula (I-C), the cytotoxicity of these agents was compared with previously synthesized compound BO-1055 and cisplatin against human lymphoblastic leukemia (CCRF-CEM) and its sub-cell line resistant to Vinblastine (CCRF-CEM/VBL), prostate cancer (PC3), colon cancer (HCT-116) and lung cancer (H460 and H1299). It reveals that compounds having —NHC(O)R group at the para position are generally more cytotoxic than the corresponding compounds having —NHC(O)R group at the meta position. Moreover, compounds having an acetamide (wherein n=1) side-chain are more potent than the corresponding propanamide (n=2) side-chain. We also found that compounds having —NHC(O)R group at the meta position (meta position) have no cross-resistance to Vinblastine, while compounds having —NHC(O)R group at the para position have a little cross-resistance to the natural anticancer agent.

TABLE 1

Cytotoxicity $IC_{50}$ Value (μM) of the compounds of Formula (I-A) and Formula (I-B) against CCRF-CEM leukemic sublines, MX-1 and HCT-116 solid tumor cell growth in vitro.

| Compound | CCRF-CEM | CCRF-CEM/Taxol[b] | CCRF-CEM/VBL[b] | MX-1 | HCT-116 |
| --- | --- | --- | --- | --- | --- |
| BO-1038 | 0.19 | 0.43 | 0.66 | 0.34 | 1.42 |
| BO-1231 | 0.11 | 0.31 | 0.24 | 0.18 | 0.30 |
| BO-1049 | 0.36 | 0.59 | 0.56 | 1.83 | 3.69 |
| BO-1233 | 0.12 | 1.83 | 0.85 | 0.36 | 0.38 |
| BO-1242 | 0.06 | 4.19 | 6.95 | 0.28 | 0.15 |
| BO-1393 | 0.58 | 0.91 | 1.22 | 1.78 | 1.26 |
| BO-1391 | 0.26 | 0.57 | 0.50 | 1.02 | 2.02 |
| BO-1228 | 0.20 | 1.54 | 2.02 | 0.26 | 0.26 |
| BO-1034 | 0.23 | 0.39 | 0.38 | 0.81 | 0.90 |
| BO-1262 | 0.94 | ND | 0.72 | ND | ND |
| BO-1263 | 7.89 | ND | 7.58 | ND | ND |
| BO-1547 | 0.24 | ND | 4.13 | ND | ND |
| BO-2294 | 3.01 | ND | 2.53 | ND | ND |
| BO-2295 | 1.86 | ND | 2.11 | ND | ND |
| BO-1037 | 0.06 | 17.10 | 64.14 | 0.37 | 0.22 |
| BO-1050 | 0.03 | 0.39 | 1.80 | 0.12 | 0.26 |
| BO-1051 | 0.08 | 0.09 | 0.13 | 0.24 | 0.44 |
| BO-1079 | 0.14 | 0.38 | 0.60 | 0.53 | 0.80 |
| BO-1149 | 0.01 | 0.02 | 0.02 | 0.59 | 0.16 |
| BO-1053 | 0.01 | 0.18 | 0.30 | 0.06 | 0.06 |
| BO-1150 | 0.02 | 0.03 | 0.03 | 0.58 | 0.26 |
| BO-1148 | 0.01 | 0.03 | 0.05 | 1.20 | 0.26 |
| BO-1154 | 0.01 | 0.01 | 0.02 | 0.37 | 0.07 |
| BO-1062 | 0.08 | 0.14 | 0.18 | 0.10 | 0.57 |
| BO-1063 | 0.07 | 0.10 | 0.13 | 0.08 | 0.44 |
| BO-1171 | 0.08 | 0.22 | 0.16 | 0.21 | 0.43 |
| BO-1064 | 0.13 | 0.17 | 0.16 | 0.29 | 0.61 |
| BO-1172 | 0.09 | 0.16 | 0.12 | 0.18 | 0.19 |
| BO-1213 | 0.02 | 0.03 | 0.19 | 0.14 | 0.24 |
| BO-1066 | 0.21 | 0.31 | 0.11 | 0.34 | 1.71 |
| BO-1054 | 0.09 | 0.24 | 0.32 | 0.60 | 0.75 |
| BO-1244 | 0.19 | 0.65 | 0.75 | 1.13 | 0.30 |
| BO-1245 | 0.75 | 3.36 | 6.42 | 5.97 | 2.40 |
| BO-1065 | 0.32 | 0.51 | 0.48 | 0.09 | 0.64 |
| Taxol | 0.0013 | 0.43 | 1.27 | 0.04 | 0.0013 |
| Vinblastine | 0.00073 | 0.08 | 0.50 | 0.0029 | 0.0018 |

[a]Cell growth inhibition was measured by the XTT assay for leukemic cells and the SRB assay for solid tumor cells after 72-hr incubation using a microplate spectrophotometer. $IC_{50}$ values were determined from dose-effect relationship at six or seven concentrations of each drug by using the CompuSyn software by Chou and Martin based on the median-effect principle and plot. Ranges given for Taxol and Vinblastine were mean ± SE (n = 4).
[b]CCRF-CEM/Taxol and CCRF-CEM/VBL are subcell lines of CCRF-CEM cells that are 330-fold resistant to Taxol, and 680-fold resistant to Vinblastine, respectively, when comparing with the $IC_{50}$ of the parent cell line.

TABLE 2

Cytotoxicity $IC_{50}$ Value (μM) of the compounds of Formula (I-C) in cell lines of CEM, CEM-VBL, HCT-116, H460, H1299 and PC3.

| Compound | CCRF-CEM | CCRF-CEM/VBL | PC3 | HCT-116 | H460 | H1299 |
| --- | --- | --- | --- | --- | --- | --- |
| BO-2189 | 0.78 | 2.70 | 19.01 | 9.56 | 8.74 | 10.64 |
| BO-2183 | 2.01 | 1.38 | 12.99 | 4.62 | 5.67 | 11.69 |
| BO-2151 | 3.41 | 0.97 | 12.85 | 5.41 | 6.55 | 9.36 |
| BO-2184 | 1.35 | 1.33 | 10.08 | 7.50 | 5.62 | 8.55 |
| BO-2182 | 3.87 | 1.32 | 35.78 | 12.96 | 19.50 | 26.42 |
| BO-2188 | 30.43 | 1.81 | 25.91 | 6.15 | 12.28 | 12.80 |
| BO-2091 | 0.52 | 14.39 | 13.49 | 3.28 | 16.79 | 8.99 |

TABLE 2-continued

Cytotoxicity IC$_{50}$ Value (μM) of the compounds of Formula (I-C) in cell lines of CEM, CEM-VBL, HCT-116, H460, H1299 and PC3.

| Compound | CCRF-CEM | CCRF-CEM/VBL | PC3 | HCT-116 | H460 | H1299 |
|---|---|---|---|---|---|---|
| BO-2120 | 0.86 | 13.04 | 12.97 | 3.21 | 6.79 | 5.77 |
| BO-2121 | 0.67 | 27.08 | 10.34 | 5.11 | 9.84 | 4.33 |
| BO-2147 | 0.39 | 6.01 | 5.73 | 3.51 | 7.88 | 4.63 |
| BO-2148 | 3.10 | 4.84 | 35.45 | 16.75 | 38.47 | 15.94 |
| BO-2191 | 1.63 | 1.53 | 22.09 | 15.66 | 14.22 | 11.04 |
| BO-2095 | 0.29 | 1.34 | 7.33 | 2.54 | 1.21 | 5.36 |
| BO-2094 | 0.32 | 2.16 | 3.57 | 1.70 | 0.93 | 3.43 |
| BO-2093 | 0.26 | 2.00 | 3.52 | 1.77 | 0.95 | 3.41 |
| BO-2092 | 0.31 | 1.45 | 2.24 | 1.50 | 1.05 | 2.52 |
| BO-2096 | 1.13 | 18.38 | 16.01 | 6.67 | 4.74 | 18.63 |
| BO-2117 | 1.14 | 52.21 | 7.24 | 4.24 | 14.93 | 14.36 |
| BO-2060 | 0.25 | 8.03 | 3.08 | 1.77 | 1.41 | 7.62 |
| BO-2073 | 0.30 | 8.27 | 2.47 | 2.09 | 1.83 | 10.30 |
| BO-2075 | 0.28 | 17.12 | 3.48 | 1.48 | 1.03 | 6.43 |
| BO-2057 | 0.24 | 6.20 | 2.28 | 1.77 | 1.58 | 3.03 |
| BO-2074 | 1.06 | 23.42 | 9.74 | 7.02 | 3.95 | 15.19 |
| BO-2118 | 0.72 | 119.64 | 29.96 | 11.07 | 14.46 | 36.01 |
| BO-1055 | 1.23 | 1.05 | 17.64 | 9.43 | 38.27 | 14.79 |
| Cisplatin | 3.54 | 1.64 | 9.96 | 12.69 | 18.41 | 13.57 |

Inhibition of Biosynthesis of DNA, RNA and Protein

Figure 2:
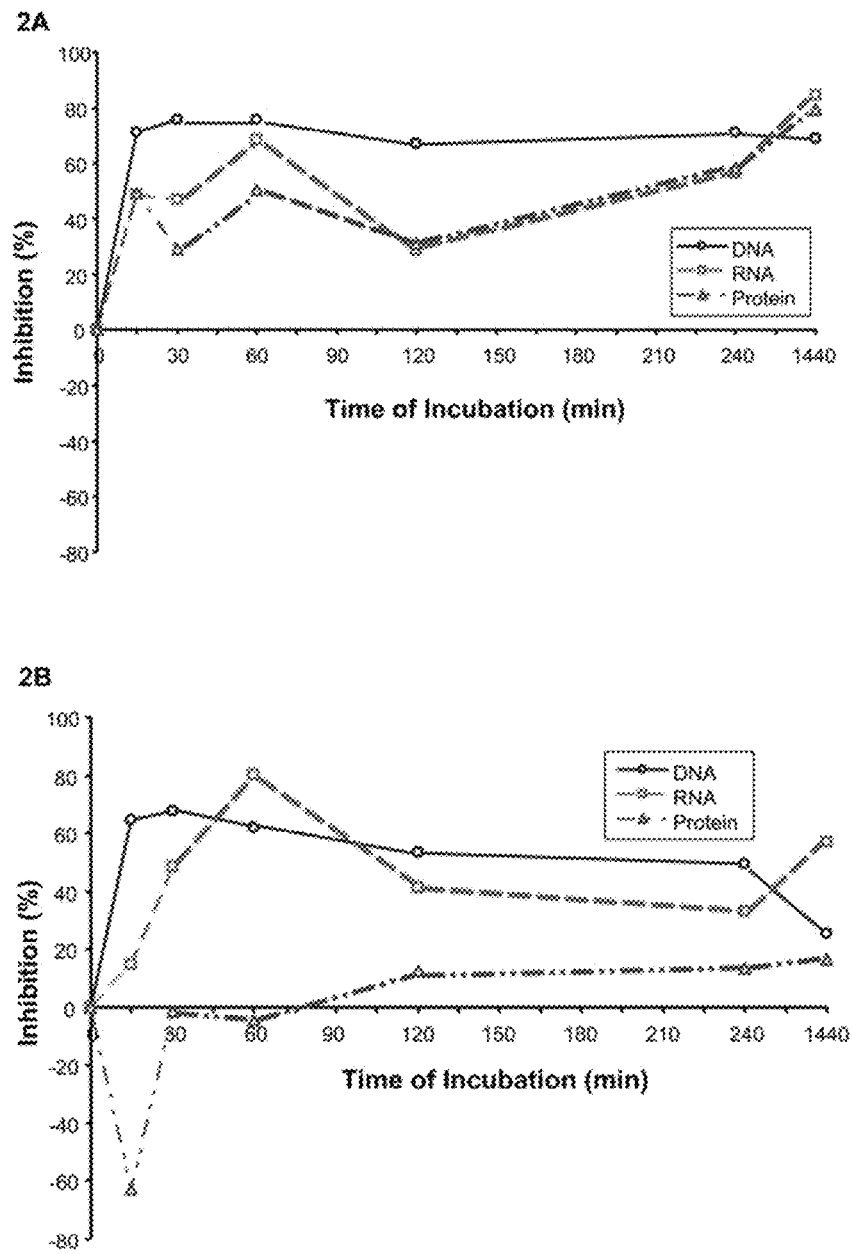
FIG. 2 illustrates inhibition of biosynthesis of DNA, RNA and protein by representative new compounds, BO-1038 (FIG. 2A) and BO-1051 (FIG. 2B) at the concentration of 10 µM.

FIG. 2 shows the time course of inhibition of biosynthesis of DNA, RNA and protein by representative new compounds, BO-1038 and BO-1501. [$^3$H]Thymidine (1 uCi), [$^3$H]adenosine (1 μCi) and [$^3$H]leucine (2 μCi) were used as the tracers for incorporation into DNA, RNA and protein, respectively. Each 1 mL incubation mixture contained 5.2×105 MX-1 cells, and 10 μM or 10 μM of BO-1038 or BO-1051, respectively. Incubation was terminated at each time points as indicated. For details of the method see Chou et al. Cancer Research 43: 3074-3079, 1983. As shown in FIG. 2, the degrees of inhibiting biosynthesis of DNA and RNA for both compounds were maximized at 50-80%. The half-maximal inhibition was reached within 15-30 min and persisted for over 6-24 hrs. The protein synthesis inhibition by BO-1038 was at similar degree as RNA synthesis inhibition which ranged 40-80% inhibition. However, the protein synthesis inhibition by BO-1051 was less than 20%, and there was an initial activation within the first 30 min followed by the moderate inhibition of about 20%. The degrees of inhibiting DNA and RNA biosynthesis by BO-1051 were similar except there was a delay in reaching maximal effect for about 1 hr.

In Vivo Antitumor Therapeutic Effect

Figure 4:
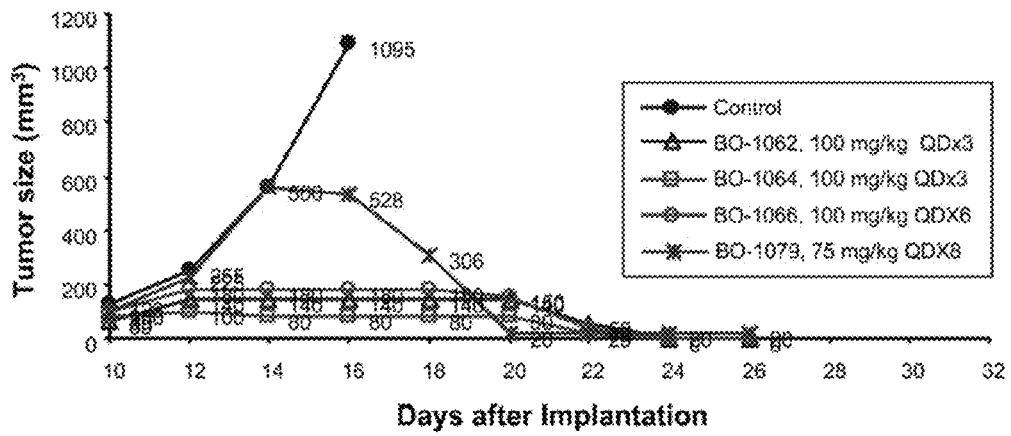
FIG. 4 illustrates therapeutic effect of BO-1062, 1064, 1066 and 1079 in nude mice bearing MX-1 (i.v. inj, n=1), tumor size changes (FIG. 4A) and body weight changes (FIG. 4B).
Figure 4:
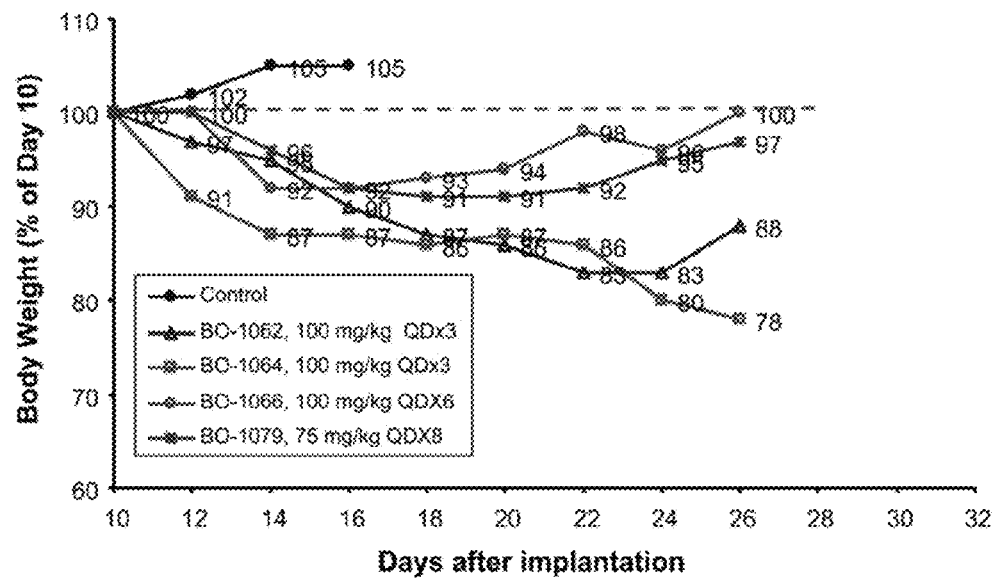
Figure 5:
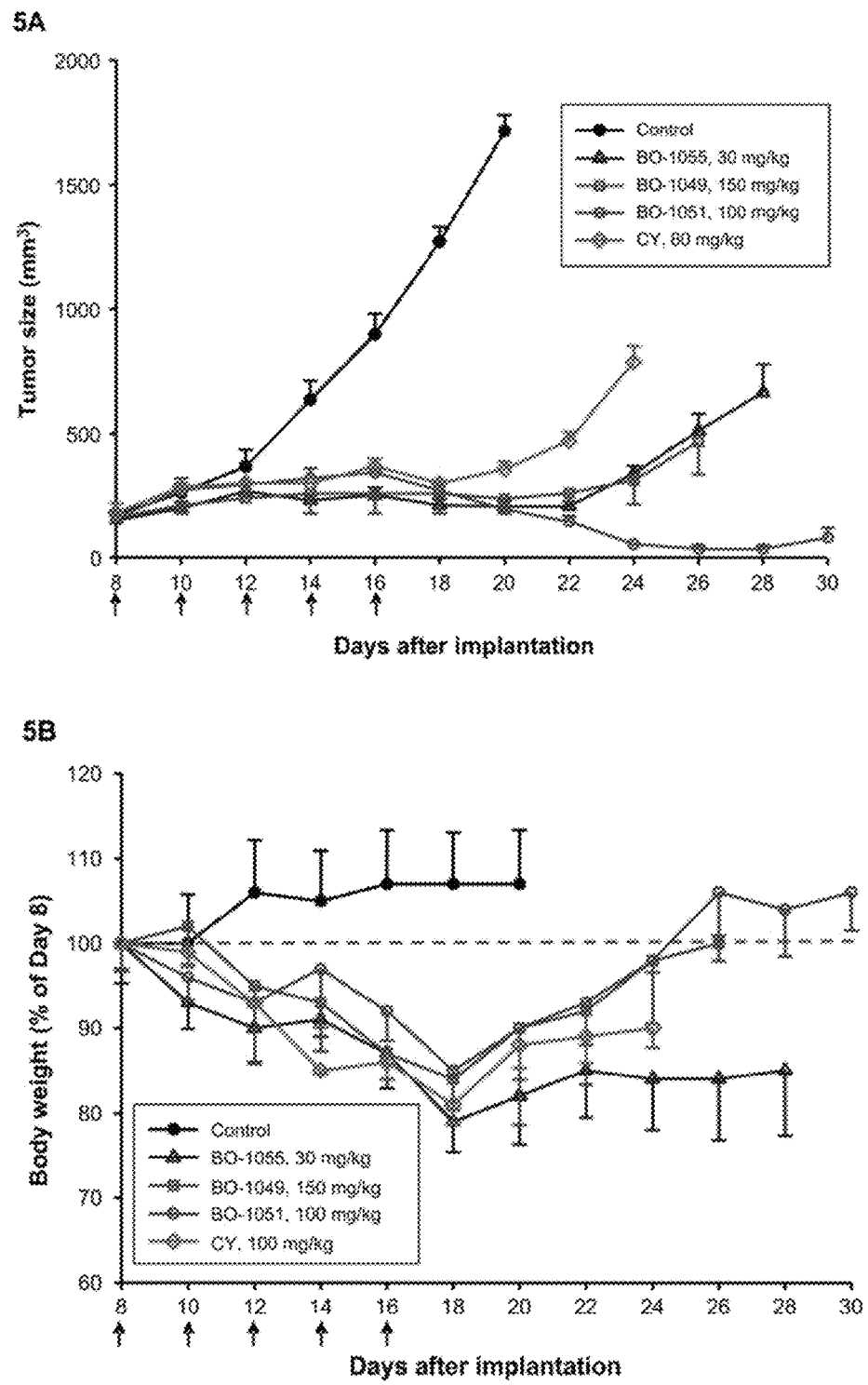
FIG. 5 illustrates therapeutic effects of BO-1049, 1051, 1055 and Cyclophosphamide in nude mice bearing human glioma U87 MG xenograft (iv. inj., Q2D×5, n=3), tumor size changes (FIG. 5A) and body weight changes (FIG. 5B).

Athymic nude mice bearing the nu/nu gene were used for human breast tumor MX-1 xenograft (FIGS. 3 and 4) and human brain glioma U87 GM xenograft (FIG. 5). Nude mice were obtained from National Cancer Institute, Frederick, Md. Male mice 6 weeks old or older weighing 22 g or more were used for experiments with subcutaneous tumor inoculation as described previously.[67] Drug was administrated via the tail vein by iv injection. Tumor volumes were assessed by measuring length×width×height (or width) by using caliper. Vehicle used was 20 μL DMSO in 180 μL saline. All animal studies were conducted in accordance with the guidelines of the U.S. National Institutes of Health Guide for the Care and Use of Animals and the protocol approved by the Institutional Animal Care and Use Committee.

Table 3 shows the in vivo antitumor therapeutic effect of representative compounds. Nude mice bearing human tumor were treated with these agents at the dose of 30-150 mg/kg, every other two days (Q2D), five times (for BO-1038-BO1055) or daily (QD) 3 to 5 times (for BO-1062-BO-1079) via intravenous injection, resulted in tumor total disappearance (or complete remission, CR) with low toxicity. These results demonstrated the newly invented compounds possess potent antitumor therapeutic efficacy and have potential for clinical applications.

Figure 3:
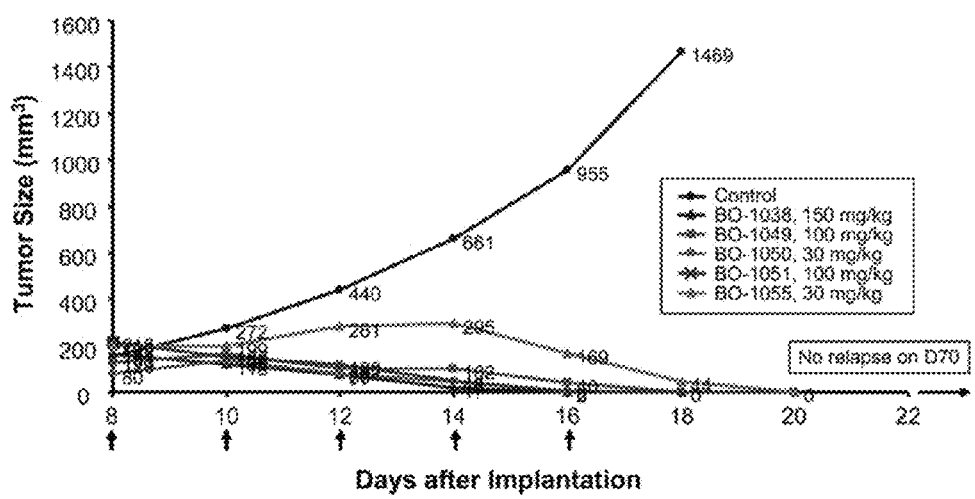
FIG. 3 illustrates therapeutic effect of BO-1038, 1049, 1050, 1051 and 1055 in nude mice bearing MX-1 xenograft, (i.v. inj, Q2D×5, n=3), average tumor size changes (FIG. 3A) and average body weight changes (FIG. 3B).
Figure 3:
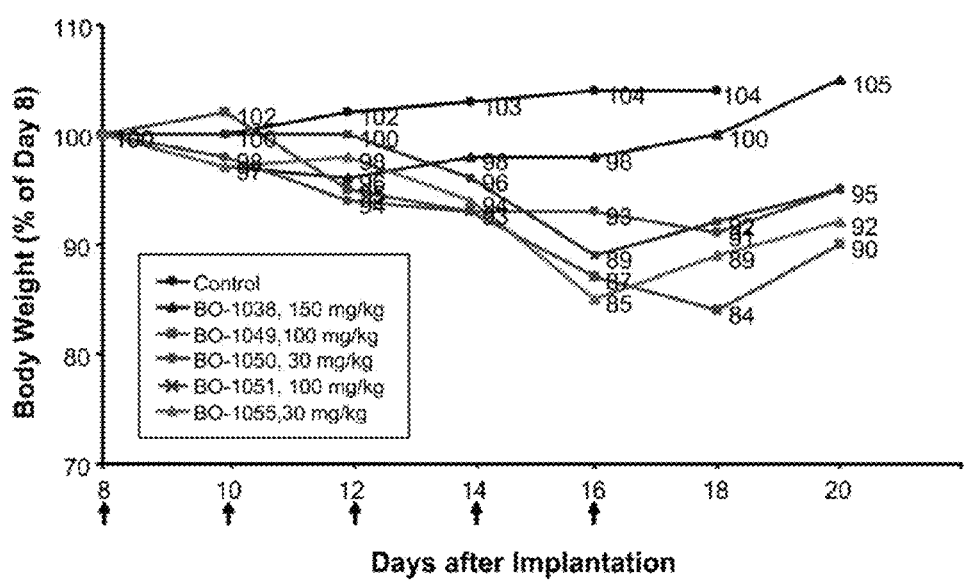

Examples of therapeutic effects for the representative N-mustard compounds against human breast carcinoma MX-1 xenograft in nude mice are summarized in Table 3. Under the experimental conditions as indicated, BO-1051, 1053, 1038, 1049, 1055 (FIGS. 3, A and B) and 1062, 1064 and 1066 (FIGS. 4, A and B) achieved complete tumor remission, whereas BO-1037 and 1050 (FIGS. 3, A and B) achieved CR in parts of the mice. Remarkably, BO-1038, 1049, 1050, 1051 and 1055, with only one cycle 5-dose-treatments, complete remission was achieved and maintained for over 70 days without any relapse in 3 out of 3 mice (FIG. 3A). Based on Eq. 4, the log cell kill (LSK) is estimated to be >4.1.

TABLE 3

Antitumor therapeutic effects of newly synthesized N-mustard compound against human mammary carcinoma MX-1 xenograft in nude mice[1]

| Compound | Dose (mg/kg) | Schedule | Therapeutic effect | Maximal body-weight loss (%) | Remark |
|---|---|---|---|---|---|
| BO-1037 | 50-90 | Q2D x 8 Q2D x 2 | 2/3 CR on D23, 25 2/3 relapsed on D40, 40 | 12 | |
| BO-1050 | 30 | Q2Dx5 | 2/2 CR on D16, 18 No relapse on D26 | 9 | See FIG. 3A, B |
| BO-1051[2] | 100 | Q2Dx5 | 3/3 CR on D16, 16, 18 No relapse on D70 | 11 | See FIG. 3A, B |
| BO-1079 | 75 | QDx8 | 1/1, >99% tumor growth suppression | 9 | See FIG. 4A, B |
| BO-1053 | 70 | Q2Dx5 | NA | NA | Too high dose |
| BO-1038 | 150 | Q2Dx5 | 3/3 CR on D16, 16, 16 No relapse on D70 | 4 | See FIG. 3A, B |
| BO-1049[2] | 100 | Q2Dx5 | 3/3 CR on D18, 18, 18 No relapse on D70 | 16 | See FIG. 3A, B |
| BO-1055[2] | 30 | Q2Dx5 | 3/3 CR on D20, 20, 20 No relapse on D70 | 15 | See FIG. 3A, B |
| BO-1062 | 100 | Q2Dx5 | 1/1 CR on D22 | 17 | See FIG. 4A, B |
| BO-1063 | 100 | QDx3 | NA | NA | Too high dose |
| BO-1064 | 100 | QDx3 | 1/1 CR on D22 | Died of Toxicity D28 | See FIG. 4A, B |

TABLE 3-continued

Antitumor therapeutic effects of newly synthesized N-mustard compound against human mammary carcinoma MX-1 xenograft in nude mice[1]

| Compound | Dose (mg/kg) | Schedule | Therapeutic effect | Maximal body-weight loss (%) | Remark |
|---|---|---|---|---|---|
| BO-1066 | 100 | QDx3 | 1/1 CR on D22 | 13 | See FIG. 4A, B |
| BO-1065 | 100 | QDx3 | NA | NA | Too high dose |

[1]Treatment started on Day 8 after tumor implantation. All treatments were carried out via i.v. injection. CR is referred as complete tumor remission.
[2]For therapeutic effect against human U87 GM glioma s.c. xenograft in nude mice, see FIG. 5A and 5B.

The therapeutic effects of N-mustard compounds, BO-1049, 1051 and 1055, against human glioma U87 GM s.c. xenograft in nude mice were given in FIGS. 5, A and B. U87 glioma is known to be refractory tumor that can not be effectively treated with cell-cycle specific anti-tumor drugs such as taxol, epothilones, or arabinosylcytosine. However, cell-cycle non-specific drugs such as alkylating agent, cyclophosphamide or BCNU, yields better therapeutic results. As shown in FIG. 5, BO-1049 (150 mg/kg), BO-1051 (100 mg/kg), and BO-1055 (30 mg/kg), Q2Dx5, i.v.-injection, resulted in complete tumor-growth suppression. However, upon 6 days of recession of treatment with BO-1049 or BO-1055, the tumor began to regrow. Remarkably, those mice with BO-1051 (100 mg/kg, Q2Dx5, n=3), it not only completely suppressed tumor growth but also continued to shrink tumor to only 18% of original tumor size (i.e., nearly complete remission) with only one cycle of treatment. Furthermore, this tumor shrinkage effect was observed on 10 and 12 days after the last dose of BO-1051 on Day 16 (The treatment started on Day 8). Interestingly, all three compounds (BO-1049, 1051 and 1055) yielded superior therapeutic effects than cyclophosphamide (80 mg/kg, Q2Dx5) in a parallel study.

DNA Cross-Linking Study

Figure 6:
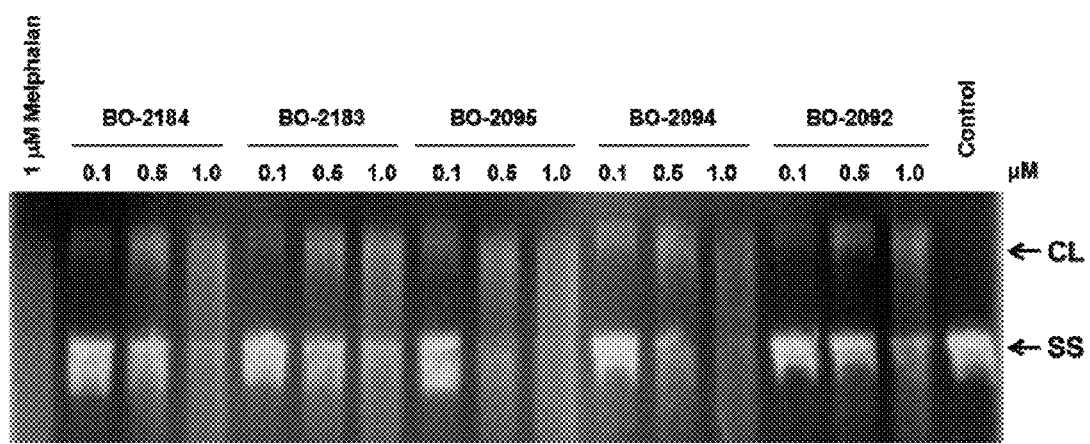
FIG. 6 illustrates the representative DNA cross-linking gel shift assay for newly synthesized water-soluble N-mustard derivatives, BO-2184, BO-2183, BO-2095, BO-2094, BO-2092, at the concentrations of 0.1, 0.5, and 1.0 µM. Melphalan (1.0 µM) was used as a positive control. CL: crosslinking; SS: single strand.

To realize whether the newly synthesized compounds are capable of cross-linking with DNA, linearized pBR322DNA was treated with selected compounds, BO-2184, BO-2183, BO-2095, BO-2094, BO-2092, at the concentrations of 0.1, 0.5, and 1.0 µM, using alkaline agarose gel shifting assay. Melphalan (1.0 µM) was used as a positive control. As revealed in FIG. 6, all tested compounds are able to bind covalently (interstrand cross-linking) with DNA, suggesting that DNA cross-linking may be the main mechanism of action for these agents.

REFERENCES

The content of each of the references disclosed in the present application is entirely incorporated herein by reference.

1. Hansson, J.; Lewensohn, R.; Ringborg, U.; Nilsson, B. Formation and removal of DNA cross-links induced by melphalan and nitrogen mustard in relation to drug-induced cytotoxicity in human melanoma cells. *Cancer Res.* 1987, 47, 2631-2637.
2. Suzukake, K.; Vistica, B. P.; Vistica, D. T. Dechlorination of L-phenylalanine mustard by sensitive and resistant tumor cells and its relationship to intracellular glutathione content. *Biochem. Pharmacol.* 1983, 32, 165-167.
3. Kaldor, J. M.; Day, N. E.; Hemminki, K. Quantifying the carcinogenicity of antineoplastic drugs. *Eur. J. Cancer Clin. Oncol.* 1988, 24, 703-711.
4. Creech, H. J.; Preston, R. K.; Peck, R. M.; O'Connell, A. P. Antitumor and mutagenic properties of a variety of heterocyclic nitrogen and sulfur mustards. *J. Med. Chem.* 1972, 15, 739-746.
5. Kohn, K. W.; Orr, A.; O'Connor, P. M. Synthesis and DNA-sequence selectivity of a series of mono- and difunctional 9-aminoacridine nitrogen mustards. *J. Med. Chem.* 1994, 37, 67-72.
6. Gourdie, T. A.; Valu, K. K.; Gravatt, G. L.; Boritzki, T. J.; Baguley, B. C.; Wakelin, L. P. G.; Wilson, W. R.; Woodgate P. D.; Denny, W. A. DNA-directed alkylating agents. 1. Structure-activity relationships for acridine-linked aniline mustards: consequences of varying the reactivity of the mustard. *J. Med. Chem.* 1990, 33, 1177-1186.
7. Valu, K. K.; Gourdie, T. A.; Gravatt, G. L.; Boritzki, T. J.; Woodgate, P. D.; Baguley, B. C.; Denny, W. A. DNA-Directed Alkylating Agents. 3. Structure-activity relationships for acridine-linked aniline mustards: consequences of varying the length of the linker chain. *J. Med. Chem.* 1990, 33, 3014-3019.
8. Gravatt, G. L.; Baguley, B. C.; Wilson, W. R.; Denny, W. A. DNA-directed alkylating agents. 4. 4-Anilinoquinoline-based minor groove directed aniline mustards. *J. Med. Chem.* 1991, 34, 1552-1560.
9. McClean, S.; Costelloe, C.; Denny, W. A.; Searcey, M.; Wakelin, L. P. G. Sequence selectivity, cross-linking efficacy and cytotoxicity of DNA-targeted 4-anilinoquinoline aniline mustards. *Anti-Cancer Drug Design,* 1999, 14, 187-204.
10. Fan, J.-Y.; Valu, K. K.; Woodgate, P. D.; Baguley, B. C.; Denny, W. A. Aniline mustard analogues of the DNA-intercalating agent amsacrine: DNA intercalation and biological activity. *Anti-Cancer Drug Design,* 1997, 12, 181-203.
11. Koyama, M.; Takahashi, K.; Chou, T.-C.; Darzynkiewicz, Z.; Kapuscinnski, J.; Kelly, T. R.; Watanabe, K. Y. Intercalating agents with covalent bond forming capability. A novel type of potential anticancer agents. 2. Derivatives of chrysophanol and emodin. *J. Med. Chem.* 1989, 32, 1594-1599.
12. Köhler, B.; Su, T.-L.; Chou, T.-C.; Jiang, X.-J.; Watanabe, K. A. Synthesis of cyclopentanthraquinones: analogues of mitomycin C. *J. Org. Chem.* 1993, 58, 1680-1686.
13. Wyatt, M. D.; Garbiras, B. J.; Haskell, M. K.; Lee, M.; Souhami, R. L.; Hartley, J. A. Structure-activity relationship of a series of nitrogen mustard- and pyrrole-containing minor groove binding agents related to distamycin. *Anti-Cancer Drug Designs,* 1994, 9, 511-525.
14. Wyatt, M. D.; Lee, M.; Hartley, J. A. Alkylation specificity for a series of distamycin analogues that tether chloambucil. *Anti-Cancer Drug Design,* 1997, 12, 49-60.
15. Bacherikov, V. A.; Chou, T.-C.; Dong, H.-J.; Chen, C.-H.; Lin, Y.-W.; Tsai, T.-J.; Su, T.-L. Potent antitumor N-mustard derivatives of 9-anilinoacridine, synthesis and antitumor evaluation. *Bioorg. Med. Chem. Lett.* 2004, 14, 4719-4722.
16. Bacherikov, V. A.; Chou, T.-C.; Dong, H.-J.; Zhang, X.; Chen, C.-H.; Lin, Y.-W.; Tsai, T.-J.; Lee, R.-Z.; Liu, L. F.; Su, T.-L. Potent antitumor 9-anilinoacridines bearing an alkylating N-mustard residue on the anilino ring: synthesis and biological activity. *Bioorg. Med. Chem.* 2005, 13, 3993-4006.
17. Su, T.-L.; Lin, Y.-W.; Chou, T.-C.; Zhang, X.; Bacherikov, V. A.; Chen, C.-H.; Liu, L. F.; Tsai, T.-J. Potent antitumor 9-anilinoacridines and acridines bearing an alkylating N-mustard residue on the acridine chromophore: Synthesis and biological activity. *J. Med. Chem.* 2006, 49, 3710-3718.
18. Su, T.-L.; Chou, T.-C.; Kim, J. Y.; Huang, J.-T.; Ciszewska, G.; Ren, W.-Y.; Otter, G. M.; Sirotnak, F. M.; Watanabe, K. A. 9-Substituted acridine derivatives with long half-life and potent antitumor activity: synthesis and structure-activity relationships. *J. Med. Chem.* 1995, 38, 3226-3235.
19. Su, T.-L. Development of DNA topoisomerase II-mediated anticancer agents, 3-(9-acridinylamino)-5-hydroxymethylaniline (AHMAs) and related compounds. *Current Med. Chem.* 2002, 9, 1677-1688.
20. Friedlos, F.; Denny, W. A.; Palmer, B. D.; Springer, C. J. Mustard Prodrugs for Activation by *Escherichia coli* Nitroreductase in Gene-Directed Enzyme Prodrug Therapy. *J. Med. Chem.* 1997, 40, 1270-1275.
21. Helsby, N. A.; Atwell, G. J.; Yang, S.; Palmer, B. D.; Anderson, R. F.; Pullen, S. M.; Ferry, D. M.; Hogg, A.; Wilson, W. R.; Denny, W. A. Aziridinyldinitro-benzamides: Synthesis and Structure-Activity Relationships for Activation by *E. coli* Nitroreductase. *J. Med. Chem.* 2004, 47, 3295-307.
22. Caroline J. Springer, Robert Dowell, Philip J. Burke, Elma Hadley, D. Huw Davies, David C. Blakey, Roger G. Melton, and Ion Niculescu-Duvaz Optimization of Alkylating Agent Prodrugs Derived from Phenol and Aniline Mustards: A New Clinical Candidate Prodrug (ZD2767) for Antibody-Directed Enzyme Prodrug Therapy. *J Med. Chem.* 1995, 38, 5051-5065.
23. Niculescu-Duvaz, I.; Cooper, R. G.; Stribbling, S. M.; Heyes, J. A.; Metcalfe, J. A.; Springer, C. J. Recent developments in gene-directed enzyme prodrug therapy (GDEPT) for cancer. *Curr Opin Mol. Ther.* 1999, 1, 480-486.
24. Masterson, L. A.; Spanswick, V. J.; Hartley, J. A.; Begent, R. H.; Howard, P. W.; Thurston, D. E. Synthesis and biological evaluation of novel pyrrolo [2,1-c][1,4]-benzodiazepine prodrugs for use in antibody-directed enzyme prodrug therapy. *Bioorg. Med. Chem. Lett.* 2006, 16, 252-256.
25. Davies L. C.; Friedlos, F.; Hedley, D.; Martin, J; Ogilvie, L. M.; Scanlon, I J.; Springer, C. J. Novel fluorinated prodrugs for activation by carboxypeptidase G2 showing good in vivo antitumor activity in gene-directed enzyme prodrug therapy. *J. Med. Chem.* 2005, 48, 5321-5328.
26. Schepelmann, S.; Hallenbeck, P.; Ogilvie, L. M.; Hedley, D.; Friedlos, F.; Martin, J.; Scanlon, I.; Hay, C.; Hawkins, L. K.; Marais, R.; Springer, C. J. Systemic gene-directed enzyme prodrug therapy of hepatocellular carcinoma using a targeted adenovirus armed with carboxypeptidase G2. *Cancer Res.* 2005, 65, 5003-5008.
27. Niculescu-Duvaz, I.; Scanlon, I.; Niculescu-Duvaz, D.; Friedlos, F.; Martin, J.; Marais, R.; Springer, C. J. Significant differences in biological parameters between prodrugs cleavable by carboxypeptidase G2 that generate 3,5-difluoro-phenol and -aniline nitrogen mustards in gene-directed enzyme prodrug therapy systems. *J Med. Chem.* 2004, 47, 2651-2658.
28. Mayer, A.; Sharma, S. K.; Tolner, B.; Minton, N. P.; Purdy, D.; Amlot, P.; Tharakan, G.; Begent, R. H.; Chester, K. A. Modifying an immunogenic epitope on a therapeutic protein: a step towards an improved system for antibody-directed enzyme prodrug therapy (ADEPT). *Br J. Cancer.* 2004, 90, 2402-2410.
29. Niculescu-Duvaz, D.; Niculescu-Duvaz, I.; Friedlos, F.; Martin, J.; Lehouritis, P.; Marais, R.; Springer, C. J. Self-immolative nitrogen mustards prodrugs cleavable by carboxypeptidase G2 (CPG2) showing large cytotoxicity differentials in GDEPT. *J Med. Chem.* 2003, 46, 1690-1705.
30. Cowen, R. L.; Williams, J. C.; Emery, S.; Blakey, D.; Darling, J. L.; Lowenstein, P. R.; Castro, M. G. Adenovirus vector-mediated delivery of the prodrug-converting enzyme carboxypeptidase G2 in a secreted or GPI-anchored form: High-level expression of this active conditional cytotoxic enzyme at the plasma membrane. *Cancer Gene Ther.* 2002, 9, 897-907.
31. Friedlos, F.; Davies, L.; Scanlon, I.; Ogilvie, L. M.; Martin, J.; Stribblin, S. M.; Spooner, R. A.; Niculescu-Duvaz, I.; Marais, R.; Springer C. J. Three new prodrugs for suicide gene therapy using carboxypeptidase G2 elicit bystander efficacy in two xenograft models. *Cancer Res.* 2002, 62, 61724-1729.
32. Francis, R. J.; Sharma, S. K.; Springer, C.; Green, A. J.; Hope-Stone, L. D.; Sena, L.; Martin, J.; Adamson, K. L.; Robbins, A.; Gumbrell, L.; O'Malley, D.; Tsiompanou, E.; Shahbakhti, H.; Webley, S.; Hochhauser, D.; Hilson, A. J.; Blakey, D.; Begent, R. H. A phase I trial of antibody directed enzyme prodrug therapy (ADEPT) in patients with advanced colorectal carcinoma or other CEA producing tumours. *Br J Cancer,* 2002, 87, 600-607.
33. Chang, J.-Y.; Lin, C.-F.; Pan, W.-Y.; Bacherikov, V.; Chou, T.-C.; Chen, C.-H.; Dong, H.; Cheng, S.-Y.; Tsai, T.-J.; Lin, Y.-W.; Chen, K.-T.; Chen, L.-T. Su, T.-L. New analogues of AHMA as potential antitumor agents: Synthesis and biological activity. *Bioorg. Med. Chem.* 2003, 11, 4959-4969.
34. Bacherikov, V. A.; Lin, Y. W.; Chang, J.-Y, Chen; Pan, W.-Y.; Dong, H.; Lee, R.-Z.; Chou, T.-C.; Su, T.-L. Synthesis and Antitumor Activity of 5-(9-Acrydinylamino) anisidine Derivatives. *Bioorg. Med. Chem.* 2005, 13, 6513-6520.
35. Benn, M. H.; Creighton, A. M.; Owen, L. N.; White, G. R. Cytotoxic compounds. Part II. Some amides of the "Nitrogen mustard" type. J. Chem. Soc. 1961, 2365-2375.
36. Baraldi, P. G.; Cacciari, B.; Moro, S.; Romagnoli, R.; Ji, X.-D.; Jacobson, K. A.; Gessi, |S.; Borea, P. A.; Spalluto, G. Fluorosulfonyl- and bis(2-chloroethyl)-aminophenylamino functionalized pyrazolo[4,3-e]1,2,4-triazolo[1,5-c]pyrimidine derivatives: Irreversible antagonists at the human $A_3$ adenosine receptor and molecular modeling studies. *J. Med. Chem.* 2001, 44, 2735-2742.
37. Jordan, A. M.; Khan, T. H.; Osborn, H. M. I.; Photiou, A.; Riley, P. A. Melanocyte-directed enzyme prodrug therapy (MDEPT): development of a targeted treatment for malignant melanoma. *Bioorg. Med. Chem.* 1999, 7, 1775-1780.
38. Palmer, B. D.; Wilson, W. R.; Pullen, S. M.; Denny, W. A. Hypoxia-selective antitumor agents. 3. Relationships between structure and cytotoxicity against cultured tumor cells for substituted N,N-bis(2-chloroethyl)anilines. J. Med. Chem. 1990, 33, 112-121.
39. Jordan, A. M.; Khan, T. H.; Osborn, M. I. Melanocyte-directed enzyme prodrug therapy (MDEPT): development of a targeted treatment for malignant melanoma *Bioorg. Med. Chem.* 1999, 7, 1775-1780.
40. Caroline, J. S.; Robert, D.; Philip, J. B.; Elma, H.; Davies, D. H; David, C. B.; Roger, G. M.; Ion, N. Optimization of Alkylating Agent Prodrugs Derived from Phenol and Aniline Mustards: A New Clinical Candidate Prodrug (ZD2767) for Antibody-Directed Enzyme Prodrug Therapy. *J. Med. Chem.* 1995, 38, 5051-5065.
41. Robert, I. D.; Caroline, J. S.; David, H. D.; Elizabeth, M. H.; Philip, J. B.; Thomas, B. F.; Roger, G. M.; Thomas, A. C.; David, C. B.; Anthony, B. M. New Mustard Prodrugs for Antibody-Directed Enzyme Prodrug Therapy: Alternatives to the Amide Link. *J. Med. Chem.* 1996, 39, 1100-1105.
42. Paull, K. D.; Lin, C.-M.; Hamel, E.; Lee, K.-H. Synthesis and cytotoxicity of 1,6,7,8-substituted 2-(4'-substituted phenyl)-4-quinolones and related compounds: identification as antimitotic agents interacting with tubulin. *J. Med. Chem.* 1993, 36, 1146-1156.
43. Kuo, S.-C.; Lee, H.-Z.; Juang, J.-P.; Lin, Y.-T.' Wu, T.-S.; Chang, J.-J.; Lednicer, D.; Paull, K. D.; Lin, C. M.; Hamel, E.; Lee, K.-H. Synthesis and cytotoxicity of 1,6,7,8-substituted 2-(4-substituted phenyl)-4-quinolones and related compounds: Identification as antimitotic agents interacting with tubulin. *J. Med. Chem.* 1993, 36, 1146-1156.
44. Li, P.; Wang, H.-K.; Kuo, S.-C.; Wu, T.-S.; Mauger, A.; Lin, C. M.; Hamel, E.; Lee, K.-H. Antitumor agents. 155. Synthesis and biological evaluation of 3',6,7-substituted 2-phenyl-4-quinolones as antimicrotubulin agents. *J. Med. Chem.* 1994, 37, 3400-3407.
45. Pellerano, C.; Brizzi, V.; Savini, L. *Atti Accad. Fisiocrit. Siena*, 1971, 3, 253.
46. Thomas, J.; Berkoff, C. E.; Flagg, W. B.; Gallo, J. J.; Haff, R. F., Pinto, C. A., Pellerano, C.; Savini, L. Antiviral quinolinehydrazones. Modified Free-Wilson analysis. *J. Med. Chem.* 1975, 18, 245-250.
47. Gemma, S.; Kukreja, G.; Fattorusso, C.; Persico, M.; Romano, M. P.; Altarelli, M.; Savini, L.; Campiani, G.; Fattorusso, E.; Basilico, N.; Taramelli, D.; Yardleye, V.; and Butinia, S. Synthesis of N1-arylidene-N2-quinolyl- and N2-acrydinylhydrazones as potent antimalarial agents active against CQ-resistant *P. falciparum* strains. *Bioorganic & Medicinal Chemistry Letters*, 16 (2006) 5384-5388.
48. Savini, L.; Chiasserini, L.; Gaeta, A.; and Pellerano, C., Synthesis and anti-tubercular evaluation of 4-quinolylhydrazones, *Bioorganic & Medicinal Chemistry*, 2002, 10, 2193-2198.
49. Kubo, K.; Shimizu, T.; Ohyama, S.; Murooka, H.; Nishitoba, T.; Kato, S.; Kobayashi, Y.; Yagi, M.; Isoe, T.; Nakamura, K.; Osawa, T.; Izawa, T. A Novel Series of 4-Phenoxyquinolines: Potent and Highly Selective Inhibitors of PDGF Receptor Autophosphorylation. *Bioorg. Med. Chem. Lett.* 1997, 23, 2935-2940.
50. Kubo, K.; Ohyama, S.; Shimizu, T.; Takami, A.; Murooka, H.; Nishitoba, T.; Kato, S.; Yagi, M.; Kobayashi, Y.; Iinuma, N.; Isoe, T.; Nakamura, K.; Iijima, H.; Osawa, T.; Izawa, T. Synthesis and Structure-Activity Relationship for New Series of 4-Phenoxyquinoline Derivatives as Specific Inhibitors of Platelet-Derived Growth Factor Receptor Tyrosine Kinase. *Bioorg. Med. Chem.* 2003, 11, 5117-5133.
51. Kubo, K.; Shimizu, T.; Ohyama, S.; Murooka, H.; Iwai, A.; Nakamura, K.; Hasegawa, K.; Kobayashi, Y; Takahashi, N.; Takahashi, K.; Kato, S.; Izawa, T.; Isoe, T. Novel Potent Orally Active Selective VEGFR-2 Tyrosine Kinase Inhibitors: Synthesis, Structure-Activity Relationships, and Antitumor Activities of N-Phenyl-N¹-{4-(4-quinolyloxy)phenyl}ureas. *J. Med. Chem.* 2005, 48, 1359-1366
52. Acheson, R. M.; Nisbet, D. F. Addition reactions of heterocyclic compounds. Part XLW¹
53. new azepines from substituted 2-methylquinolines and dialkyl acetylene-dicarboxylates. *J. Chem. Soc. C*, 1971, 3291-3296.
54. Parrick, J.; and Wilcox, R. Convenient routes to pyrrolo [3,2-b]-, pyrrolo[3,2-c]-, and pyrrolo[2,3-c]-quinolines, and a study of the pyrolysis of 2-quinolylhydrazones. *J. Chem. Soc., Perkin Trans.* 1, 1976, 2121-2125.
55. Singh, S. P.; Tarar, L. S.; Vaid, R. K.; Elguero, J.; Martinez, A. Reaction of 4-hydrazinoquinolines with b-diketones. synthesis and spectroscopy ($^1$H, $^{13}$C NMR, MS) of some pyrazolylquinolines. *J. Heterocycl. Chem.* 1989, 26, 733-738.
56. Su, T-L.; Chen, C.-H.; Huang, L.-F.; Basu, M. K., Chou, T.-C. Synthesis and structure-activity relationship of potential anticancer agents: Alkylcarbamates of 3-(9-acridinylamino)-5-hydroxymethylaniline. *J. Med. Chem.* 1999, 42, 4741-4748.
57. Drewe, W. C.; Nanjunda, R.; Gunaratnam, M.; Beltran, M.; Parkinson, G. N.; Reszka, A. P.; Wilson, W. D.; Neidle, S. Rational Design of Substituted Diarylureas: A Scaffold for Binding to G-Quadruplex Motifs. *J. Med. Chem.* 2008, 51, 7751-7767.
58. Cuenca, F.; Moore, M. J. B.; Johnson, K.; Guyen, B.; Cian, A. D.; Neidle, S. Design, synthesis and evaluation of 4,5-di-substituted acridone ligands with high G-quadruplex affinity and selectivity, together with low toxicity to normal cells, *Bioorg. Med. Chem. Lett.* 2009, 19, 5109-5113.
59. Vohra, G. J. *Indian Chem. Soc.* 1946, 23, 9-10.
60. Moorhouse, A. D.; Santos, A. M.; Gunaratnam, M.; Moore, M.; Neidle, S.; Moses, J. E. Stabilization of G-Quadruplex DNA by Highly Selective Ligands via Click Chemistry, *J. Am. Chem. Soc.* 2006, 128, 15972-15973.
61. Lombardo, C. M.; Martinez, I. S.; Haider, S.; Gabelica, V.; Pauw, E. D.; Mosesc, J. E.; Neidle, S. Structure-based design of selective high-affinity telomeric quadruplex-binding ligands, *Chem. Commun*, 2010, 46, 9116-9118.
62. Scudiero, D. A.; Shoemaker, R. H.; Paull, K. D.; Monks, A.; Tierney, S.; Nofziger, T. H.; Currens, M. J.; Seniff, D.; Boyd, M. R. Evaluation of Soluble Tetrazolium/Formazan Assay for Cell Growth and Drug Sensitivity in Culture Using Human and Other Tumor Cell Lines. *Cancer Res.* 1988, 48, 4827-4833.
63. Skehan, P.; Storeng, R. H.; Scudiero, D.; Monks, A.; McMahon, J.; Vistica, D.; Warren, J. T.; Bokesch,; Kenny, S.; Boyd, M. R. New Colorimetric Cytotoxicity Assay for Anticancer-Drug Screening. *J. Natl. Cancer Inst.* 1990, 82, 1107-1112.
64. Chou, T.-C.; O'Connor, O. A.; Tong, W. P.; Guan, Y.-B.; Zhang, X.-G.; Stachel, S. J.; Lee, S.; Danishefsky, S. J. The Synthesis, Discovery and Development of a Highly Promising Class of Microtubule Stabilization Agents: Curative Effects of Desoxyepothilones B and F against Human Tumor Xenografts in Nude Mice. *Proc. Natl. Acad. Sci. USA* 2001, 98, 8113-8118.
65. Chou, T.-C. and Martin, N. CompuSyn for Drug Combinations: PC Software and User's Guide: A Computer Program for Quantitation of Synergism and Antagonism in Drug Combinations, and the Determination of $IC_{50}$ and $ED_{50}$ and $LD_{50}$ Values. ComboSyn, Inc., Paramus, N.J. 2005.
66. Chou, T.-C.; Talalay, P. Quantitative Analysis of Dose-Effect Relationships: the Combined Effects of Multiple Drugs or Enzyme Inhibitors. *Adv. Enzyme Regul.* 1984, 22, 27-55.
67. Chou, T.-C. Theoretical basis, experimental design and computerized simulation of synergism and antagonism in drug combination studies. *Pharmacol. Rev.* 2006, 58, 621-681.

The invention claimed is:
1. The compound selected from the group consisting of
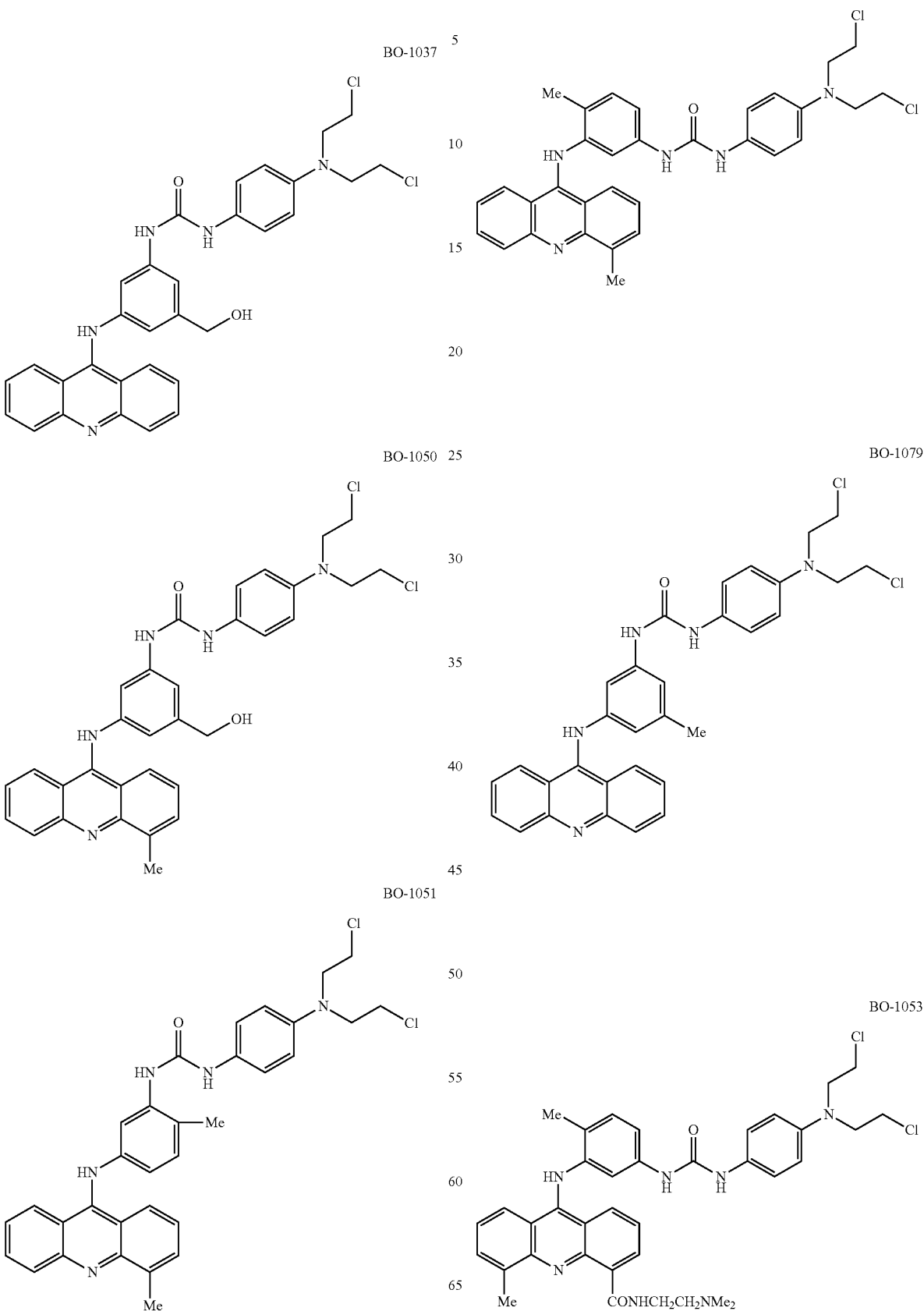

-continued
BO-1063
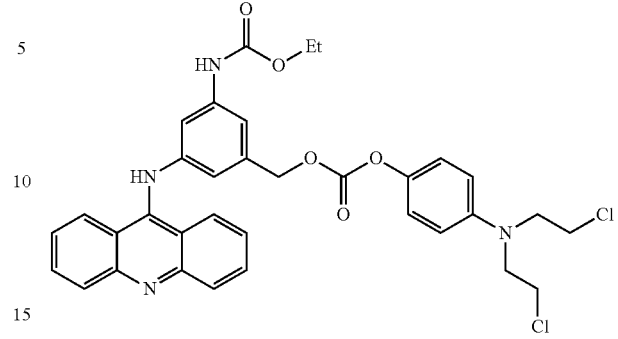
BO-1065
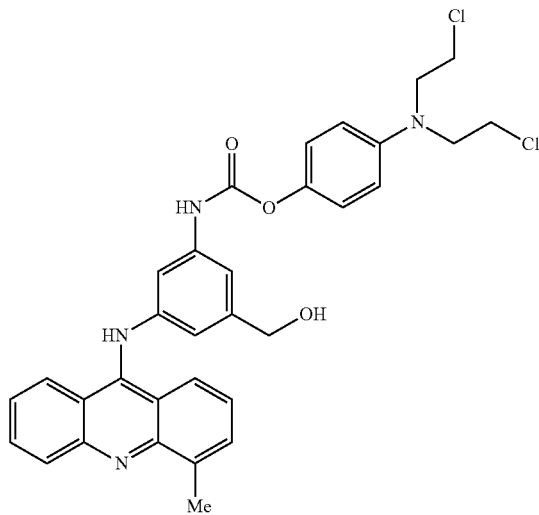
BO-1062
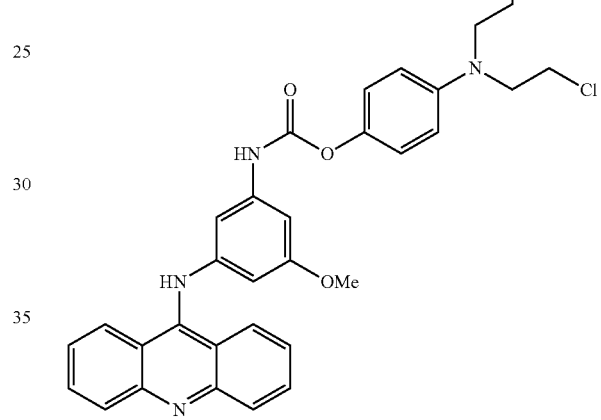
BO-1066
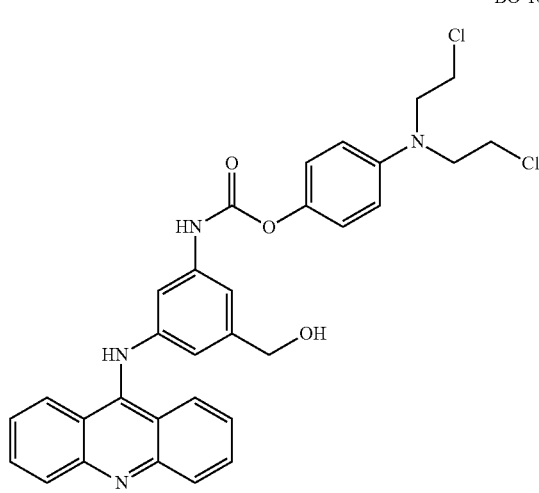
BO-1064
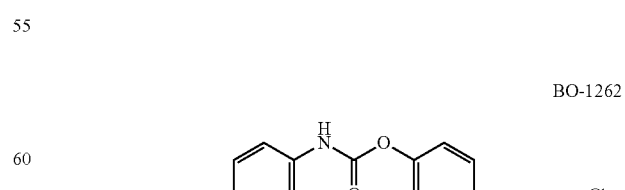
BO-1263
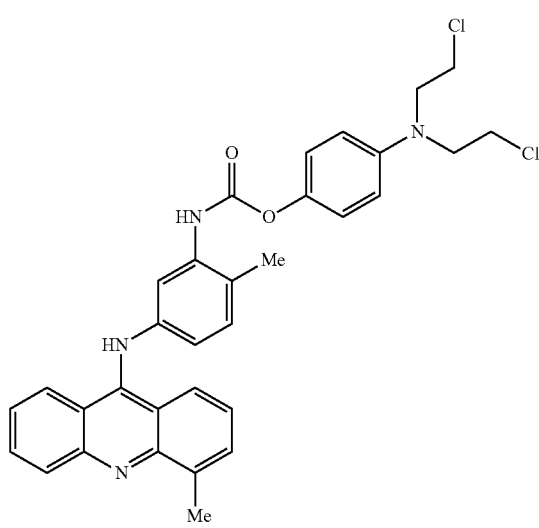
BO-1262
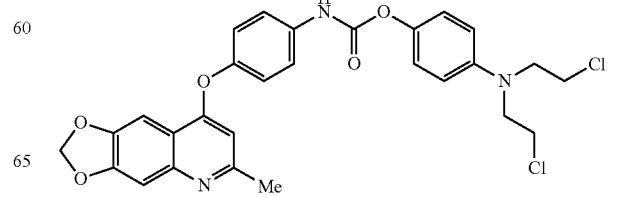

-continued

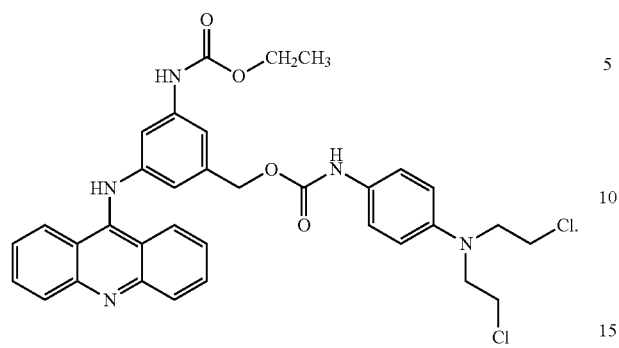
BO-1054

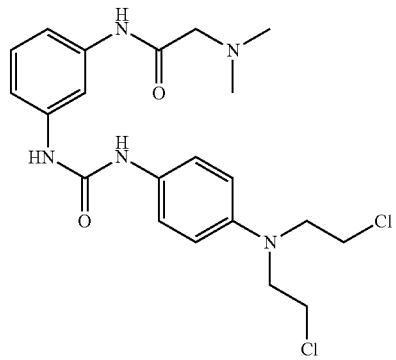
BO-2189

2. The compound of Formula (I-C):

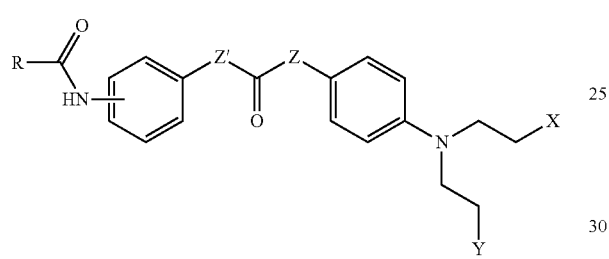
(I-C)

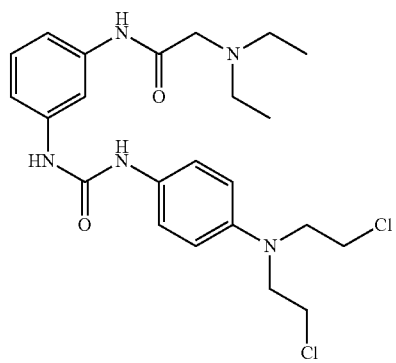
BO-2183 or a salt thereof;
wherein:
X and Y are independently selected from the group consisting of Cl, Br, I, and OSO$_2$Me;
Z is —NH or —O—;
Z' is —NH, —NHNH, —OCH$_2$—, or —O—;
—NHC(O)R is at the meta or para position corresponding to Z';
R is selected from optionally substituted C$_1$-C$_6$ alkyl, optionally substituted alkenyl, optionally substituted alkynyl, optionally substituted heterocyclyl and optionally substituted aryl.

3. The compound of claim 2, wherein X and Y are the same.

4. The compound of claim 3, wherein X and Y are Cl.

5. The compound of claim 2, wherein Z is —NH.

6. The compound of claim 2, wherein Z' is —NH.

7. The compound of claim 2, wherein R is —(CH$_2$)nNR$^1$R$^2$, and n is 1 to 6.

8. The compound of claim 7, wherein R$^1$ and R$^2$ are the same or independently C$_1$-C$_6$ alkyl.

9. The compound of claim 7, wherein NR$^1$R$^2$ is a cyclic amine.

10. The compound of claim 9, wherein NR$^1$R$^2$ is selected from the group consisting of morpholine, pyrrolidine, piperidine, 1-methylpiperazine and 4-piperidinopiperidine.

11. The compound of claim 2, wherein the compound is selected from the group consisting of

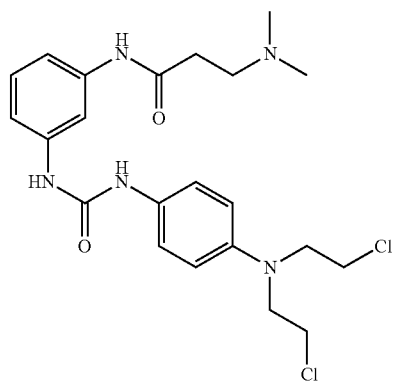
BO-2091

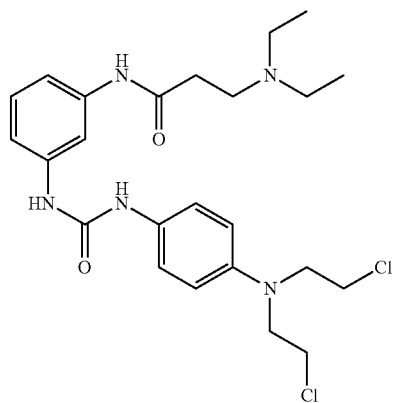
BO-2120

93
-continued
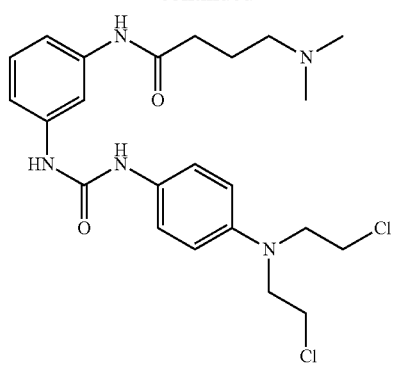
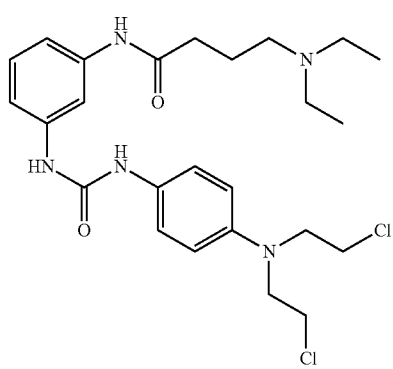
BO-2151
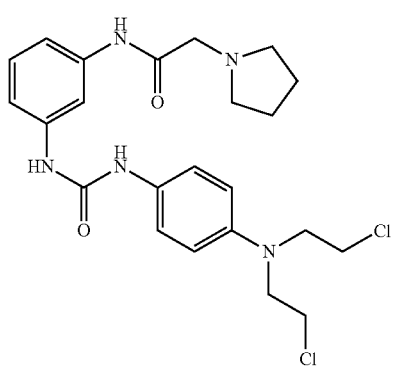
BO-2121
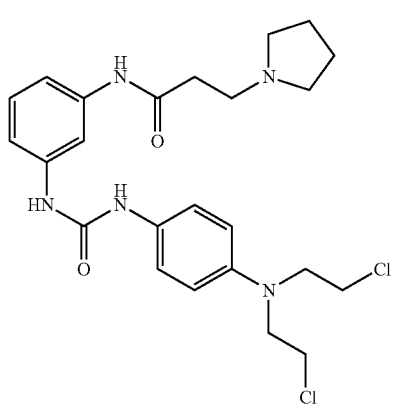
94
-continued
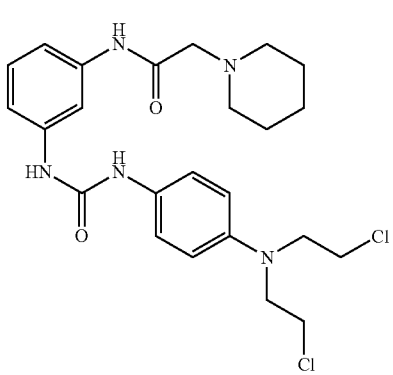
BO-2184
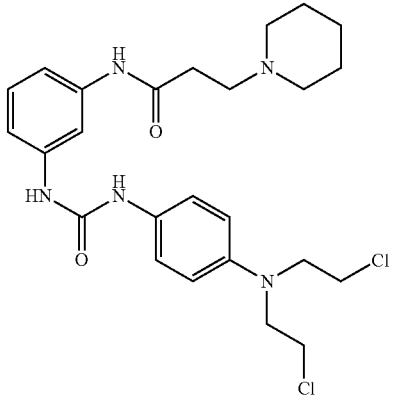
BO-2147
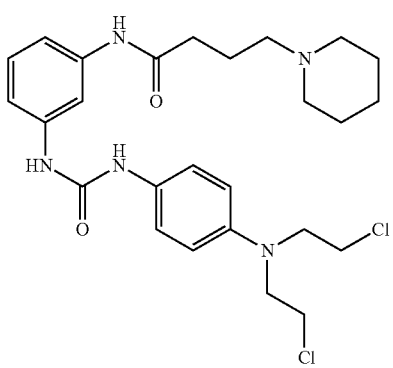

95
-continued
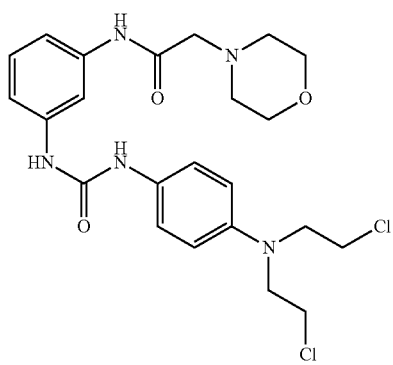
BO-2182
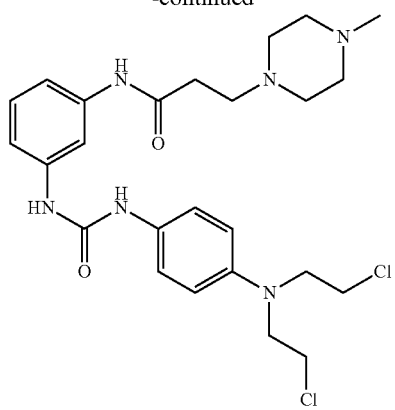
BO-2148
96
-continued
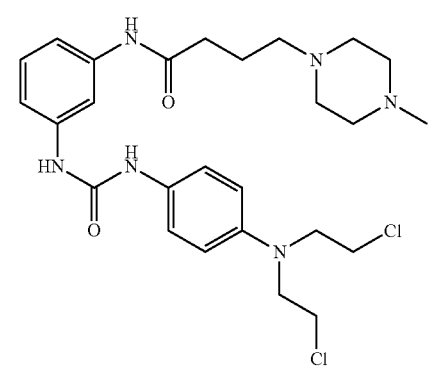
BO-2188
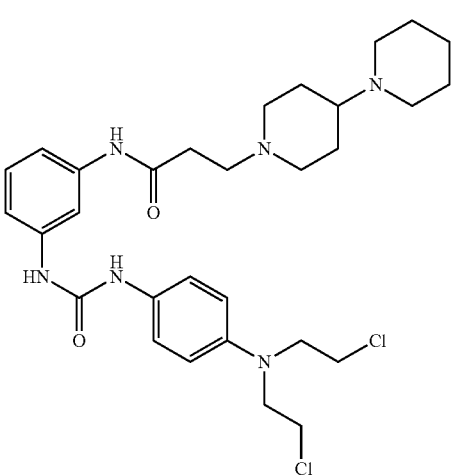
BO-2191

97
-continued
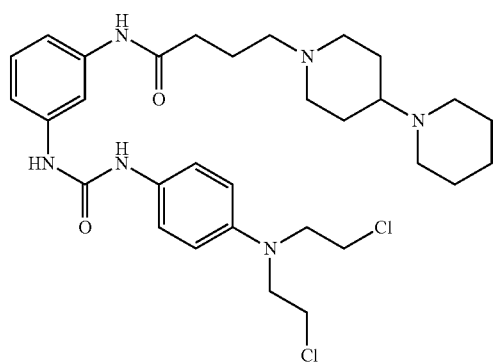
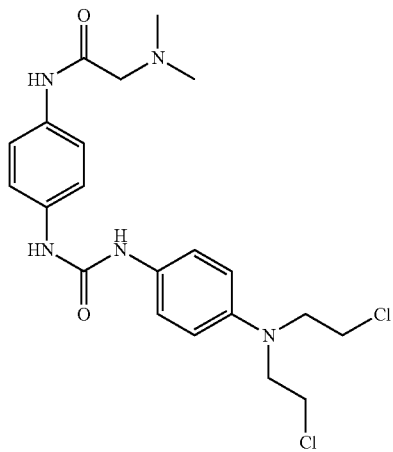
BO-2095
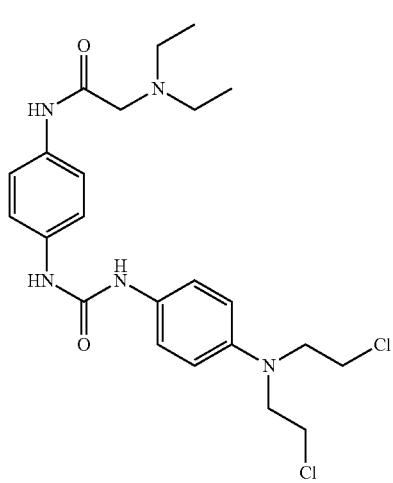
BO-2094
98
-continued
BO-2060
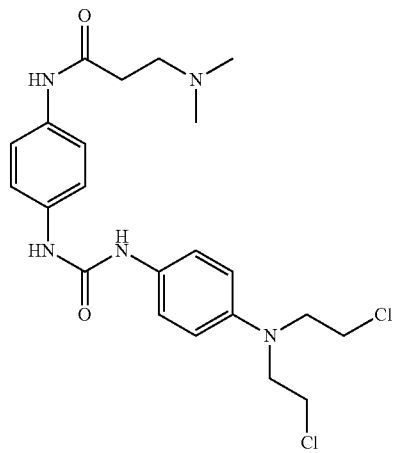
BO-2073
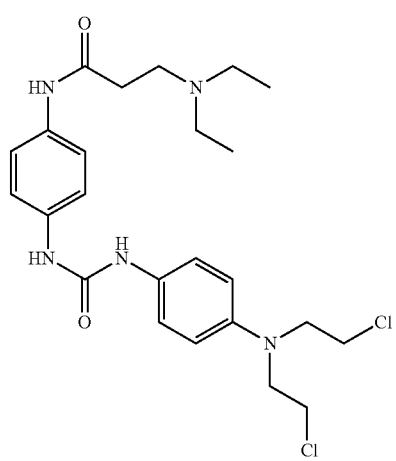
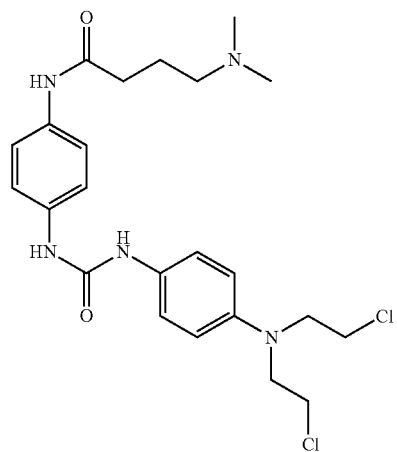

| 99 | 100 |
|---|---|
| -continued | -continued |
| 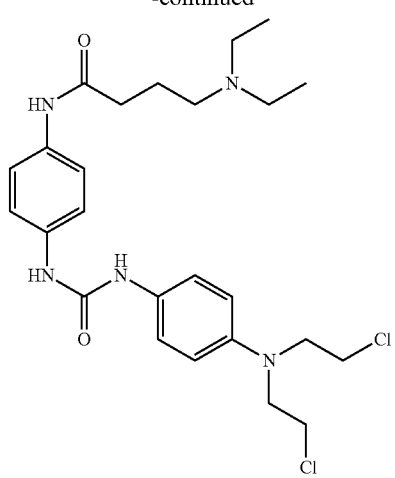 | 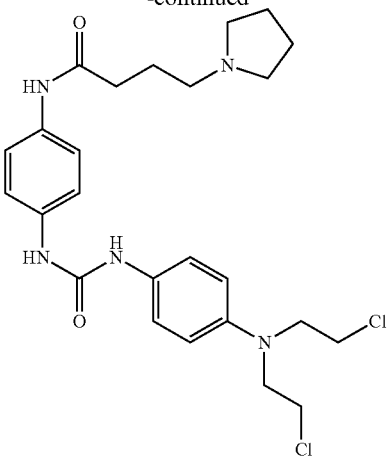 |
| 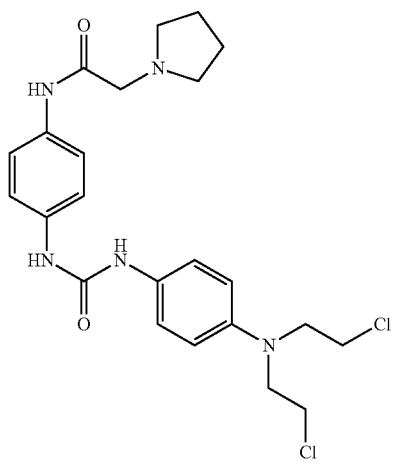
BO-2093 | 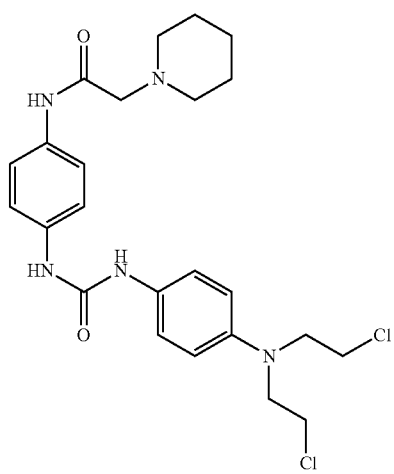
BO-2092 |
| 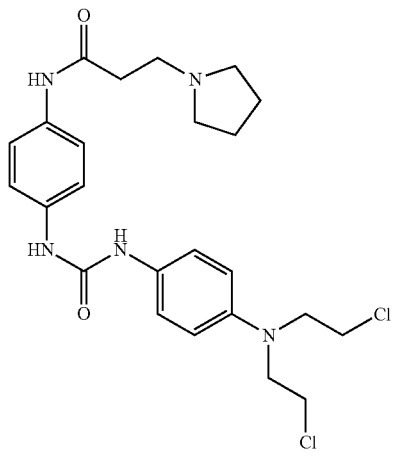
BO-2075 | 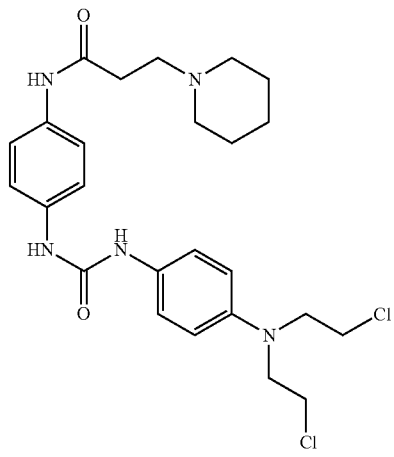
BO-2057 |

| 101 | 102 |
|---|---|
| -continued | -continued |
| 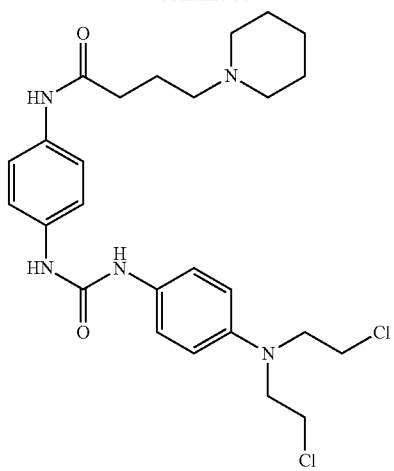 | 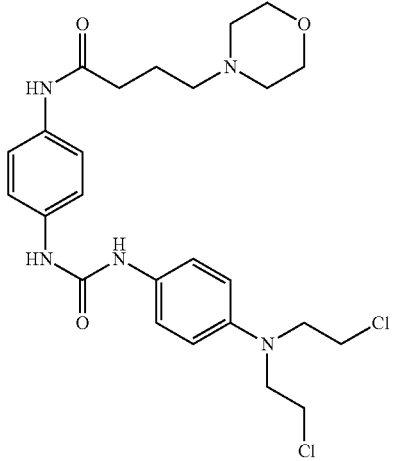 |
| 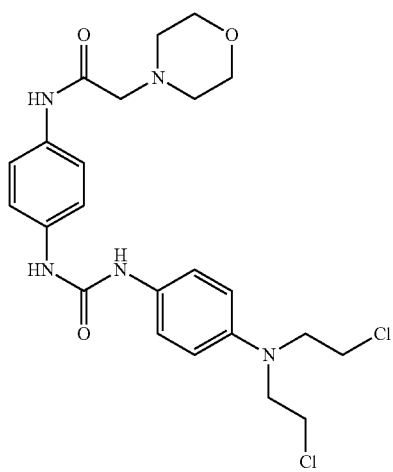  BO-2096 | |
| 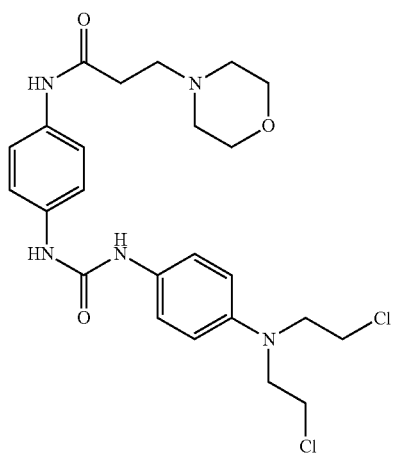  BO-2074 | 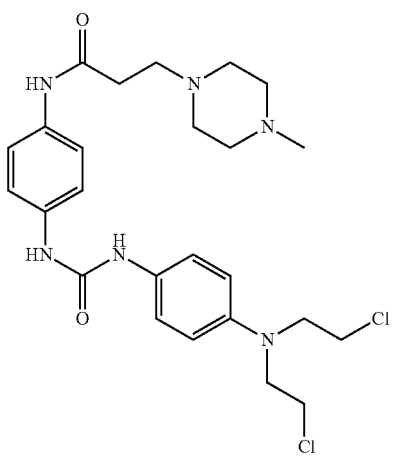 |

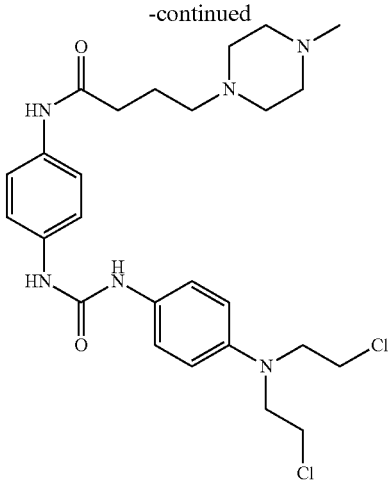
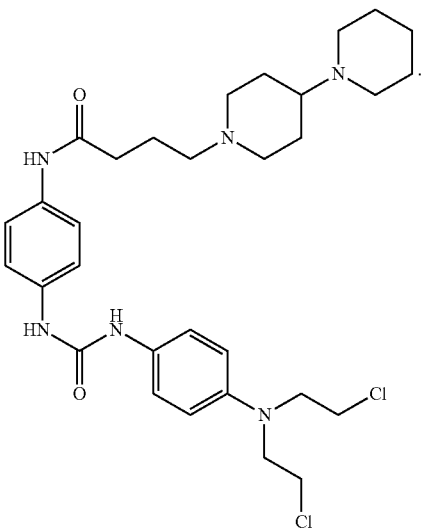
BO-2117
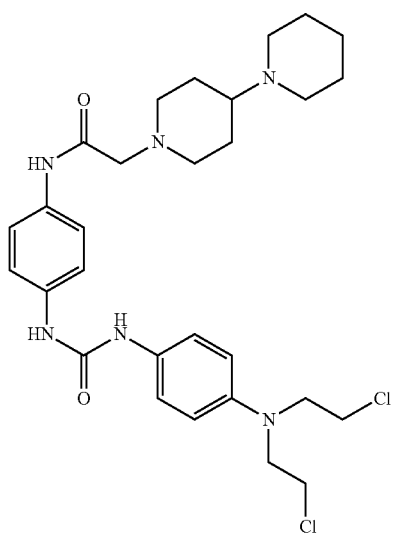
12. The compound having the formula:
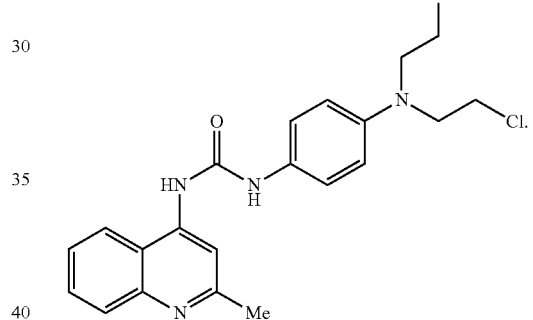
BO-1038
13. The compound of claim 2, wherein the compound is
BO-2118
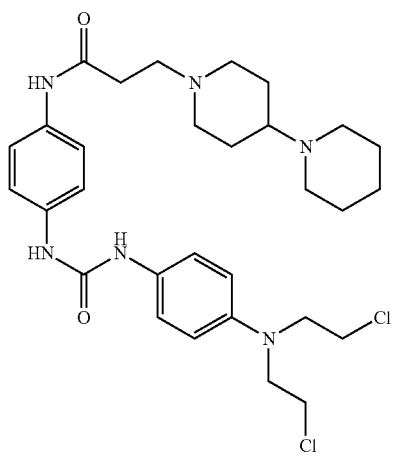
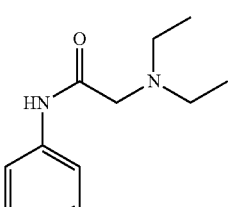
BO-2094
* * * * *